(12) United States Patent
Haufe et al.

(10) Patent No.: US 9,345,791 B2
(45) Date of Patent: May 24, 2016

(54) LIGANDS FOR TARGETING OF S1P RECEPTORS FOR IN VIVO IMAGING AND TREATMENT OF DISEASES

(75) Inventors: Guenter Haufe, Muenster (DE); Bodo Levkau, Muenster (DE); Michael Schaefers, Muenster (DE); Stefani Silke Schilson, Muenster (DE); Petra Keul, Duesseldorf (DE)

(73) Assignee: Westfaelische Wilhelms-Universitaet Muenster, Muenster (DE)

( * ) Notice: Subject to any disclaimer, the term of this patent is extended or adjusted under 35 U.S.C. 154(b) by 0 days.

(21) Appl. No.: 14/237,572

(22) PCT Filed: Aug. 16, 2012

(86) PCT No.: PCT/EP2012/066009
§ 371 (c)(1),
(2), (4) Date: Feb. 7, 2014

(87) PCT Pub. No.: WO2013/026765
PCT Pub. Date: Feb. 28, 2013

(65) Prior Publication Data
US 2014/0170067 A1     Jun. 19, 2014

(30) Foreign Application Priority Data
Aug. 19, 2011 (EP) .................... 11178071

(51) Int. Cl.
*A61K 51/04* (2006.01)
*C07C 311/41* (2006.01)
*C07C 215/10* (2006.01)
*C07C 233/18* (2006.01)
*C07D 401/14* (2006.01)

(52) U.S. Cl.
CPC .............. *A61K 51/04* (2013.01); *C07C 215/10* (2013.01); *C07C 233/18* (2013.01); *C07C 311/41* (2013.01); *C07D 401/14* (2013.01)

(58) Field of Classification Search
CPC .... A61K 51/00; C07C 311/41; C07C 215/10; C07C 711/10
See application file for complete search history.

(56) References Cited

U.S. PATENT DOCUMENTS 5,719,176 A * 2/1998 Fujita et al. .................... 514/440

FOREIGN PATENT DOCUMENTS

WO   WO-2005/014603 A1   2/2005

OTHER PUBLICATIONS

Ming-Rong Zhang et al. [18F]Fluoroalkyl Agents: Synthesis, Reactivity and Application for Development of PET Ligands in Molecular Imaging. Current Topics in Medicinal Chemsitry, 2007, 7, 1817-1828.*

Mandala et al., Alteration of Lymphocyte Trafficking by Sphingosine-1-Phosphate Receptor Agonists, Science, 296(5566): 346-349 (2002).

International Search Report of PCT/EP2012/066009, 3 pages (mailed Oct. 23, 2012).

Barter, P.J. et al., Antiinflammatory properties of HDL, Circulation Research, 95(8):764-772 (2004).

Bera, R. et al., Pd/C-catalyzed alkynylation of beta-chloroacroleins, Tetrahedron, 63(52):13018-13023 (2007).

Chuit, P. and Hausser, J., Reduction of dimethyl ethers of polymethylene dicarboxylic acids of 15 to 21 carbon atoms with sodium and alcohol, Helvetica Chimica Acta, 12(1):850-859 (1929). French.

Cohen, J.A. and Chun, J., Mechanisms of fingolimod's efficacy and adverse effects in multiple sclerosis, American Neurological Association, 69(5):759-777 (2011).

Durand, P. et al., A new efficient synthesis of the immunosuppressive agent FTY-720, Synthesis, 4:505-506 (2000).

Fujita, T. et al., Potent immunosuppressants, 2-alkyl-2-aminopropane-1,3-diols1, Journal of Medicinal Chemistry, 39(22):4451-4459 (1996).

Ghosh, T.N. and Dutta, S., Isoquinoline derivatives. Part 1, Journal of Indian Chemical Society, 32(1):17-22 (1955).

Girianda-Junges, C. et al., Effect of cyclohexonic long chain fatty alcohols on neurite outgrowth. Study on structure-activity relationship, Tetrahedron, 54(27):7735-7748 (1998).

Hannun, Y.A. and Obeid, L.M., Principles of bioactive lipid signalling: lessons from sphingolipids, Nature Reviews. Molecular Cell Biology, 9(2):139-150 (2008).

Hla, T. and Volker, B., Sphingosine 1-phosphate (S1P) Physiology and the effects of S1P receptor modulation, Neurology, 76(8):53-58 (2011).

Karliner, J.S., Sphingosine kinase and sphingosine 1-phosphate in cardioprotection, Journal of cardiovascular pharmacology, 53(3):189-197 (2009).

Keul, P. et al., The sphingosine-1-phosphate analogue FTY720 reduces atherosclerosis in apolipoprotein E-deficient mice, Arteriosclerosis, Thrombosis, and Vascular Biology, 27(3):607-613 (2007).

Kim, S. et al., Efficient synthesis of the immunosuppressive agent FTY720, Synthesis 5:753-755 (2006).

(Continued)

*Primary Examiner* — Michael G Hartley
*Assistant Examiner* — Jagadishwar Samala
(74) *Attorney, Agent, or Firm* — Choate, Hall & Stewart, LLP; Brenda Herschbach Jarrell; Xiaodong Li

(57) ABSTRACT

The present invention relates to novel compounds of formulae (I) and (II) which are useful in the prevention, treatment and diagnosis, in vivo diagnosis of diseases or disorders related to S1P receptors, in particular, in diseases which are connected to the regulatory function of sphingosine-1-phosphate (S1P) and its analogs, such as inflammation, pain, autoimmune diseases and cardiovascular diseases.

10 Claims, No Drawings

(56) References Cited

OTHER PUBLICATIONS

Kimura, T. et al., High-density lipoprotein stimulates endothelial cell migration and survival through sphingosine 1-phosphate and its receptors, Arteriosclerosis, Thrombosis, and Vascular Biology, 23(7):1283-1288 (2003).

Kontush, A. et al., Preferential sphingosine-1-phosphate enrichment and sphingomyelin depletion are key features of small dense HDL3 particles, Arteriosclerosis, Thrombosis, and Vascular Biology, 27(8):1843-1849 (2007).

Luke, M.M. et al., Gene variants associated with ischemic stroke, Stroke, 40(2):363-368 (2009).

Mangaleswaran, S. and Argade, N.P., A facile synthesis of naturally occurring aminopeptidase inhibitor tyromycin A\, Journal of Organic Chemistry, 66(15):5259-5261 (2001).

Murata, N. et al., Interaction of sphingosine 1-phosphate with plasma components, including lipoproteins, regulates the lipid receptor-mediated actions, The Biochemical Journal, 352(3):809-815 (2000).

Niessen, F. et al., Dendritic cell PAR1-S1P3 signalling couples coagulation and inflammation, Nature, 452(7187):654-658 (2008).

Nikolova, G. S., Enantioselective synthesis of natural product analogues 4-fluoroceramide and its phase behavior at the air/water interface. Inaugural-Dissertation, Munster University, (2005). German.

Nofer, J. et al., FTY720, a synthetic sphingosine 1 phosphate analogue inhibits development of atherosclerosis in low-density lipoprotein receptor-deficient mice, Circulation, 115(4):501-508 (2007).

Nofer, J. et al., HDL induces NO-dependent vasorelaxation via the lysophospholipid receptor S1P3, The Journal of Clinical Investigation, 133(4):569-581 (2004).

Nofer, J. et al., Suppression of endothelial cell apoptosis by high density lipoproteins (HDL) and HDL-associated lysosphingolipids, Journal of Biological Chemistry, 276(37):34480-34485 (2001).

Olivera, A. and Rivera, J., An emerging role for the lipid mediator sphingosine-1-phosphate in mast cell effector function and allergic disease, Ancances in Experimental Medicine and Biology, 716:123-142 (2011.).

Ooi, H. et al., A concise route to (+)-lacatacystin, Journal of Organic Chemistry, 69(22):7765-7768 (2004).

Pappu, R. et al., Promotion of lymphocyte egress into blood and lymph by distinct sources of sphingosine-1-phosphate, Science, 316(5822):295-298 (2007).

Rivera, R. and Chun, J., Biological effects of lysophospholipids, Reviews of Physiology, Biochemistry, and Pharmacology, 160:25-46 (2008).

Rosen, H. et al., Egress: a receptor-regulated step in lymphocyte trafficking, Immunological Reviews, 195:160-177 (2003).

Sattler, K. and Levkau, B., Sphingosine-1-phosphate as a mediator of high-density lipoprotein effects in cardiovascular protection, Cardiovascular Research, 82(2):201-211 (2009).

Sattler, K. et al., Sphingosine 1-phosphate levels in plasma and HDL are altered in coronary artery disease, Basic Research in Cardiology, 105(6):821-832 (2010).

Schneider, H. et al., Synthesis of modified partial structures of the bacterial cell wall, 1. Lipopeptides containing nonproteinogenic amino acids, Journal of Organic Chemistry, 58(3):683-689 (1993).

Schultz, W.E. et al., Synthesis of 1-14C-17-iodoheptadecanoic acid, Journal of Radioanalytical and Nuclear Chemistry, 135(3):199-205 (1989).

Schwab, S.R. and Oyster, J.G., Finding a way out: lymphocyte egress from lymphoid organs, Nature Immunology, 8(12):1295-1301 (2007).

Seitz, T. et al., Organocatalyzed route to enantioenriched pipecolic esters: decarboxylation of an aminomalonate hemiester, Tetrahedron, 62:6155-6165 (2006).

Shiffman, D. et al., Association of gene variants with incident myocardial infarction in the cardiovascular health study, Arteriosclerosis, Thrombosis, and Vascular Biology, 28(1):173179 (2008).

Skoura, A. and Hla, T., Regulation of vascular physiology and pathology by the S1P2 receptor subtype, Cardiovascular Research, 82(2):221-228 (2009).

Spiegel, S. and Milstien, S., Sphingosine-1-phosphate: an enigmatic signalling lipid, Nature Reviews. Molecular Cell Biology, 4(5):397-407 (2003).

Spiegel, S. et al., Endogenous modulators and pharmacological inhibitors of histone deacetylases in cancer therapy, Oncogene, 31(5):537-551 (2012).

Stevenson, C.E. et al., Targeting sphingosine-1-phosphate in hematologic malignancies, Anti-cancer Agents in Medicinal Chemistry, 11(9):794-798 (2011).

Takanashi, S. et al., Synthesis of elenic acid, an inhibitor of topoisomerase II from the sponge *Plakinastrella* sp., Journal of the Chemical Society, Perkin Transactions 1, 10:1603-1606 (1998).

Theilmeier, G. et al., High-density lipoproteins and their constituent, sphingosine-1-phosphate, directly protect the heart against ischemia/reperfusion injury in vivo the S1P3 lysophopholipid receptor, Circulation, 114(13):1403-1409 (2006).

Thenappan, A. and Burton, D.J., Alkylation of (Fluorocarbethoxymethylene)tri-n-butylphosphorane: A facile entry to alpha-Fluoralkanoates, Journal of Organic Chemistry, 55(8):2311-2317 (1990).

Tolle, M. et al., HDL-Associated lysophingolipids inhibit NAD(P)H oxidase-dependent monocyte chemoattractant protein-1 production, Arteriosclerosis, Thrombosis, and Vascular Biology 28(8):1542-1548 (2008).

Vachal, P. et al., Highly selective and potent agonists of sphingosine-1-phosphate 1 (S1P1) receptor, Bioorganic& Medicinal Chemistry Letters, 16:3684-3687 (2006).

Venkataraman, K. et al., Vascular endothelium as a contributor of plasma sphingosine 1-phophate, Circulation Research, 102(6):669-676 (2008).

Waeber, C. et al., Vascular sphingosine-1-phosphate S1P1 and S1P3 receptors, Drug News and Perspectives, 17(6):365-382 (2004).

Watters, R.J. et al., Targeting sphingosine-1-phosphate receptors in cancer, Anti-cancer Agents in Medicinal Chemistry, 11(9):810-817 (2011).

Xu, Z. et al., Unsaturated acyclic analogues of 2'-deoxyadenosine and thymidine containing fluorine: Synthesis and biological activity, Journal of Medicinal Chemistry, 38(6):875-882 (1995).

Yin, J. et al., Direct and convenient conversion of alcohols to flourides, Organic Letters, 6(9):1465-1468 (2004).

Zhu, J. et al., Synthetic communications: An international journal for rapid communication of synthetic organic chemistry, An International Journal for Rapid Communication of Synthetic Organic Chemistry, 25(2):215-218 (1995).

\* cited by examiner

LIGANDS FOR TARGETING OF S1P RECEPTORS FOR IN VIVO IMAGING AND TREATMENT OF DISEASES

1. FIELD OF THE INVENTION

The present invention relates to novel compounds, in particular, novel radioactive and fluorescent compounds, their preparation, and the use of such novel radioactive or fluorescent compounds as radiotracers/markers for imaging techniques and diagnostic tools in the field of diseases or disorders related to S1P receptors in particular in diseases which are connected to the regulatory function of sphingosine-1-phosphate (S1P) and its analogues, such as inflammation, pain, autoimmune diseases and cardiovascular diseases.

2. BACKGROUND

S1P and its Receptors in Biology, Medicine and Disease

Sphingosine-1-phosphate (S1P) is a biologically active sphingolipid (Hannun 2008). It controls fundamental physiological processes such as immunity, inflammation, cardiovascular function and many others (Spiegel 2003). S1P is synthesized intracellularly from sphingomyelin via phosphorylation of sphingosine by sphingosine kinases 1 and 2. While the major source of S1P in plasma are hematopoietic cells (mainly erythrocytes, platelets and leukocytes), vascular and lymphatic endothelial cells have also been shown to synthesise and release S1P (Pappu 2007, Venkataraman 2008). From inside the cell, S1P is transported to the extracellular environment in a process that involves specific ABC-type transporters in some cells. Once in plasma, S1P binds to albumin and lipoproteins (Murata 2000). The bulk of plasma S1P (~70%) is associated with high-density lipoproteins (HDL) (Nofer 2001, Kontush 2007). Such HDL-bound S1P is biologically active and is responsible for several of the beneficial effects of HDL at least in part (Nofer 2004; Kimura 2003; Barter 2004, Nofer 2001, Tolle 2008, Theilmeier 2007).

S1P plays an important role in the homeostasis of the immune system as the only molecule known to orchestrate lymphocyte exit from thymus and secondary lymphoid organs (Schwab 2007). To exit the lymph node, lymphocytes actively migrate along a S1P concentration gradient that exists between lymph node (<pM), lymph (pM) and plasma (μM). Ablation of this gradient by genetic or pharmacological manipulation leads to a complete loss of lymphocytes from the peripheral circulation by trapping them in the secondary lymphoid organs (Rosen 2003). S1P also couples coagulation with inflammation in several systemic inflammatory response syndromes such as bacterial sepsis and viral haemorrhagic fevers (Niessen 2008). S1P causally influences the efficiency and duration of the immune response and has a large impact on the regulation of the inflammatory response (Hannun 2008). S1P and its receptors play major roles in a number of other physiological and pathological settings such as multiple sclerosis, stroke, inflammation, pain, lung injury, anaphylaxis, allergy, asthma, tumorigenesis, retinopathy, vasculopathy, angiogenesis, haematologic malignancies and stem cell biology (Hla, 2009, Spiegel 2011, Olivera 2011, Stevenson 2011, Watters 2011, Cohen 2011, Hla 2011). S1P protects the heart against ischemia/reperfusion in experimental myocardial infarction and is an important mediator of preconditioning (Sattler 2009, Karliner 2009). S1P analogues have been shown to protect against atherosclerosis (Keul 2007, Nofer 2007). S1P, gene polymorphisms have been associated with coronary artery disease and stroke (Luke 2009, Shiffman, 2008). Plasma S1P levels are increased in coronary artery disease (CAD) and myocardial infarction thus constituting a novel biomarker (Sattler 2010).

S1P specifically binds to and activates five cognate G-protein-coupled cell surface receptors (S1PR) designated $S1P_{1-5}$ with a $K_d$ of 8-20 nM (Rivera 2008). The molecular details on the S1P binding to S1PR as well as the mechanism of S1PR activation are complex. Individual S1PR couple to one or more specific G-protein subunits, with considerable overlap for some but not all receptors: $S1P_1$ is coupled to $G_{i/o}$ proteins, preferentially $G_{i\alpha 1}$ and $G_{i\alpha 3}$; $S1P_2$ is associated to $G_{i/o}$, $G_{12/13}$ and $G_q$; $S1P_3$ activates either $G_{i/o}$, $G_q$ or $G_{12/13}$ proteins, and $S1P_4$ and $S1P_5$ signal through $G_{i/o}$ or $G_{12/13}$ and $G_{i/o}$ or $G_{12}$ subunits, respectively (Spiegel 2003, Waeber 2004). The complexity of S1P coupling to G-proteins drives the multiplicity of downstream signalling pathways, eliciting an intricate pattern of cellular responses depending on the relative expression levels of each S1P receptor in the cell (Spiegel 2003). Genetic deletion of the $S1P_1$ on lymphocytes and administration of $S1P_1$ agonists and antagonists, respectively, have revealed a $S1P_1$-dependent mechanism of blockade of lymphocyte egress. Remarkably, only $S1P_1$ receptor agonists, but not antagonists were able to induce lymphopenia in rodents, indicating that initial activation with subsequent downregulation and not inhibition of $S1P_1$ impedes thymocyte and lymphocyte egress (Rosen 2003, Schwab 2007). This has made the pharmacological development of synthetic S1PR agonists a novel approach to immunomodulatory therapy.

The US Food and Drug Administration (FDA) and recently, the European Commission, have approved FTY720 (fingolimod, Gilenya®) for relapsing forms of multiple sclerosis a compound which upon phosphorylation becomes a non-selective S1P receptor modulator. Thus elucidating the role of S1P is relevant for many clinical reasons.

The goal of the invention is therefore the development of subtype-specific S1P receptor ligands for treatment of diseases and to label highly affine ligands for application in PET, SPECT and fluorescent imaging that will allow imaging of S1PR expression, function and signaling in vivo and serve as novel markers of various diseases.

3. SUMMARY OF THE INVENTION

A series of substituted and unsubstituted, linear or branched, long-chain 2-alkyl-2-aminopropane-1,3-diols have been synthesized in order to investigate their affinity to S1P receptors, to quantify their pharmacokinetics and organ distribution in small animal models and to finally study their therapeutic action in patients. The diols themselves do not bind to S1P receptors, but they are phosphorylated in cells to form the active moiety in vivo.

S1P receptors are expressed in different organ systems such as the lymphatic and arterial vascular system and are regulated in various diseases. Thus, imaging agents of different nature such as radioligands and fluorescent probes based on parent 2-amino-2-(hydroxymethyl)alkan-1-ols allow imaging on a molecular level and the study of diseases in addition to pharmacokinetics and metabolism.

Surprisingly, using binding studies it has been found that the compounds of the invention functionalized in omega or in a position closed to the omega position exhibited a high affinity to the receptor compared to the corresponding parent (non-omega substituted) hydrocarbon compounds Thus, labelling of these positions would be most welcome for application such as for Positron-Emission-Tomography (PET). Surprisingly, it has been found out that even more sterically demanding terminal substituents such as tert-butyl- or adamantyl groups and electron withdrawing substituents like $SF_5$ do increase the affinity with respect to the corresponding (non-omega substituted) compounds.

Even more surprising, also the compounds of the invention when bearing a fluorescent neutral dye like the dansyl derivative or anionic dyes like Cy3, Cy5, Cy 5.5, and Cy 7 in the omega position or in a position closed to the omega position do bind to S1P receptors. Also kationic dyes are highly affine. Thus, also fluorescence imaging is possible with the claimed compounds.

When this is considered e.g. for imaging applications, the compounds of the invention when labelled or when bearing a dyes have a clear advantage, as they can be applied in a lower dose for diagnostic purposes that will not interfere with any simultaneous treatments with drugs targeting the same receptors. It is possible to administrate the compounds of the invention for imaging to patients treated simultaneously with such drugs as only trace amounts of the compound of the invention will be necessary. The compound of the invention will not compete for biological activity with such drugs and hence will not need any adjustment of the therapy with such drugs.

The omega or proximal to omega functionalized compounds of the invention are therefore useful in the prevention and treatment of human diseases in all settings where S1P and its receptors play a role.

The compounds of the invention functionalized with radiomarkers or dye in omega or in a position proximal to omega are therefore useful in the diagnosis of human diseases in all settings where S1P and its receptors play a role.

Furthermore, pharmaceutically acceptable salts, esters or amides are applicable as prodrugs.

4. DETAILED DESCRIPTION OF THE INVENTION

In a first aspect, the present invention relates to compounds of formula (I)

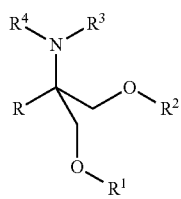

wherein:
R=—$(CH_2)_nCH_2$—X, —$(CH_2)_n$—Y—$(CH_2)_m$—X, —$(CH_2)_n$—$(CF_2)_p$—$(CH_2)_m$—X, —$(CH_2)_n$—CXH—$CH_3$, —$(CH_2)_n$—CXH—$CH_2$—$CH_3$, $(CH_2)_q$(CHOH)$(CH_2)_r$—$C_6H_4$—$(CH_2)_s$—X;
X=F, I, $CF_2SF_5$, $SF_5$, O-Aryl, —N(Alkyl)$_2$, —CHO, —CH(OAlkyl)$_2$, —$CONH_2$, CON(Alkyl)$_2$, t-butyl, adamantyl, CH=$CH_2$ and C≡CH;
Y=O, S, SO, $SO_2$, C(O), CH(OH), CH(OAlkyl), CH(O-Aryl), CH(OHeteroaryl), C(OAlkyl)$_2$, epoxide, vic-diol, vic-acetal, CH=CH and C≡C;
n=8, 9, 10, 11, 12, 13, 14, 15, 16, 17, 18, 19, and 20, preferably 14, 15 or 16
m=2, 3, 4, 5, 6, 7, 8, 9, 10;
p=1, 2, 3, 4, and 5;
q=1, 2, 3, 4, and 5;
r=0, 1, 2, 3, 4, and 5;
s=6, 7, 8, 9 and 10;
$R^1$, $R^2$ are independently H, C(O)Alkyl, C(O)Aryl, C(O)Heteroaryl, —$PO_3^{2-}$, and —P(OH)(O)$_2^-$;
$R^3$, $R^4$ are independently H, C(O)Alkyl, C(O)Aryl and C(O)Heteroaryl;
with the proviso that
when R is —$(CH_2)_n$—$(CF_2)_p$—$(CH_2)_m$—X, wherein X is as defined above, the sum n+m+p is 12-24;
when R is —$(CH_2)_n$—Y—$(CH_2)_m$—X, wherein X and Y are defined as above, the sum n+m is 12-24; and
when R is —$(CH_2)_nCH_2$—X and X is F then n is 15-16.

In a second aspect, the present invention relates to compounds of formula (I)

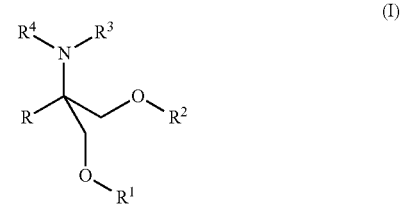

and pharmaceutical salts thereof
wherein
R=—$(CH_2)_nCH_2$—X, —$(CH_2)_n$—Y—$(CH_2)_m$—X, —$(CH_2)_n$—$(CF_2)_p$—$(CH_2)_m$—X, —$(CH_2)_n$—CXH—$CH_3$, —$(CH_2)_n$—CXH—$CH_2$—$CH_3$;
X=F, I, $CF_2SF_5$, $SF_5$, —OAryl, —N(Alkyl)$_2$, —CHO, —CH(OAlkyl)$_2$, —$CONH_2$, CON(Alkyl)$_2$, t-butyl, adamantyl, CH=$CH_2$, and C≡CH;
Y=O, S, SO, $SO_2$, C(O), CH(OH), CH(OAlkyl), CH(OAryl), CH(OHeteroaryl), C(OAlkyl)$_2$, epoxide, vic-diol, vic-acetal, CH=CH and C≡C;
n=8, 9, 10, 11, 12, 13, 14, 15, 16, 17, 18, 19, and 20, preferably 14, 15 or 16;
m=2, 3, 4, 5, 6, 7, 8, 9 and 10;
p=1, 2, 3, 4, and 5;
$R^1$, $R^2$ are independently H, C(O)Alkyl, C(O)Aryl, C(O)Heteroaryl, —$PO_3^{2-}$, and —P(OH)(O)$_2^-$;
$R^3$, $R^4$ are independently H, C(O)Alkyl, C(O)Aryl, C(O)Heteroaryl;
with the proviso that
when R is —$(CH_2)_n$—$(CF_2)_p$—$(CH_2)_m$—X, wherein X is as defined above, the sum n+m+p is 12-24;
when R is —$(CH_2)_n$—Y—$(CH_2)_m$—X, wherein Y is defined as above, the sum n+m is 12-24;
and
when R is —$(CH_2)_nCH_2$—X and X is F then n is 15-16.

In a third aspect the invention related to compounds of formula (I) wherein:
R=—$(CH_2)_nCH_2$—X, —$(CH_2)_n$—Y—$(CH_2)_m$—X, —$(CH_2)_n$—$(CF_2)_p$—$(CH_2)_m$—X, —$(CH_2)_n$—CXH—$CH_3$, —$(CH_2)_n$—CXH—$CH_2$—$CH_3$, $(CH_2)_q$(CHOH)$(CH_2)_r$—$C_6H_4$—$(CH_2)_s$—X;
X=F, I, $CF_2SF_5$, $SF_5$, —N(Alkyl)$_2$, —CHO, —CH(OAlkyl)$_2$, —$CONH_2$, CON(Alkyl)$_2$, t-butyl, adamantyl, CH=$CH_2$ and C≡CH;
Y=O, S, SO, $SO_2$, C(O), CH(OH), CH(OAlkyl), CH(OAryl), CH(OHeteroaryl), C(OAlkyl)$_2$, epoxide, vic-diol, vic-acetal, CH=CH and C≡C;

n=8, 9, 10, 11, 12, 13, 14, 15, 16, 17, 18, 19, and 20, preferably 14, 15 or 16;

M=2, 3, 4, 5, 6, 7, 8, 9, 10;

p=1, 2, 3, 4, and 5;

q=1, 2, 3, 4, and 5;

r=0, 1, 2, 3, 4, and 5;

s=6, 7, 8, 9, 10;

$R^1$, $R^2$ are independently H, C(O)Alkyl, C(O)Aryl, C(O)Heteroaryl, —$PO_3^{2-}$, and —P(OH)(O)$_2^-$;

$R^3$, $R^4$ are independently H, C(O)Alkyl, C(O)Aryl and C(O)Heteroaryl; with the proviso that when R is —(CH$_2$)$_n$—(CF$_2$)$_p$—(CH$_2$)$_m$—X, wherein X is as defined above, the sum n+m+p is 12-24;

when R is —(CH$_2$)$_n$—Y—(CH$_2$)$_m$—X, wherein X and Y are defined as above, the sum n+m is 12-24; and when R is —(CH$_2$)$_n$CH$_2$—X and X is F then n is 15-16.

In another embodiment, R is —(CH$_2$)$_n$CH$_2$—X, X is as defined above, n is 15 and $R^1$, $R^2$, $R^3$, $R^4$ are as defined above. More preferably, $R^1$, $R^2$, $R^3$, $R^4$ are H.

In another embodiment, R is —(CH$_2$)$_n$CH$_2$—X, X is F, SF$_5$, CF$_2$SF$_5$, n is 15 and $R^1$, $R^2$, $R^3$, $R^4$ are as defined above. More preferably, $R^1$, $R^2$, $R^3$, $R^4$ are H.

In another embodiment, R is —(CH$_2$)$_n$CH$_2$—X, X is F and n is 15 and $R^1$, $R^2$, $R^3$, $R^4$ are as defined above. More preferably, $R^1$, $R^2$, $R^3$, $R^4$ are H.

In another embodiment, R is —(CH$_2$)$_n$—(CF$_2$)$_p$—(CH$_2$)$_m$—X, X is F and the sum n+m+p is 14-16.

In yet another embodiment, R is —(CH$_2$)$_{15}$CH$_2$—F, $R^1$ and $R^2$ are independently H, C(O)Alkyl, C(O)Aryl, C(O)Heteroaryl, —$PO_3^{2-}$, —P(OH)(O)$_2^-$, and $R^3$ and $R^4$ are independently H, C(O)Alkyl, C(O)Aryl, C(O)Heteroaryl. More preferably $R^1$, $R^2$, $R^3$, $R^4$ are H.

In another embodiment, R is —(CH$_2$)$_n$—CXH—CH3, X is F and $R^1$, $R^2$, $R^3$, $R^4$ are as defined above. More preferably, $R^1$, $R^2$, $R^3$, $R^4$ are H. More preferably, n is 14, 15 and 16.

In another embodiment, R is —(CH$_2$)$_n$—CXH—CH$_2$—CH3, X is F and $R^1$, $R^2$, $R^3$, $R^4$ are as defined above. More preferably, $R^1$, $R^2$, $R^3$, $R^4$ are H. More preferably, n is 14, 15 and 16.

In another embodiment, R is (CH$_2$)$_q$(CHOH)(CH$_2$)$_r$—C$_6$H$_4$—(CH$_2$)$_s$—X, q is 1, r is 0, s is 8 and X is F.

In another embodiment, X is F.

In another embodiment preferably n is 14, 15, 16, 17, more preferably 15 and 16.

In an embodiment, the preferred compounds are

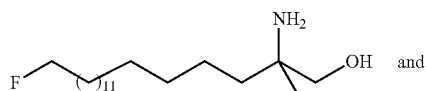
and
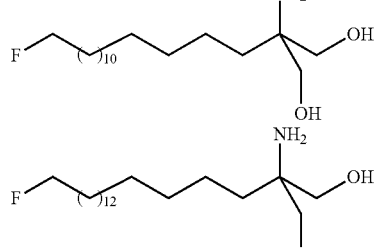

The compounds of the invention are for use in the prevention and the treatment of human diseases in all settings where S1P and its receptors play a role. Diseases wherein S1P and its receptors play a role are diseases selected from pain, immunological, inflammatory, neurological, cardiovascular, rheumatic, autoimmune, allergic, infectious, haematological, degenerative, oncological, ophthalmological, metabolic diseases.

The compounds of formula (I) may also be used as intermediates in the preparation of the compounds of formula (II) as defined below.

In a forth aspect, the invention is directed to compounds of formula (II)

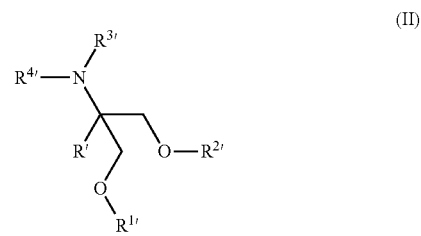

and pharmaceutical salts thereof

R'=—(CH$_2$)$_n$CH$_2$—X, —(CH$_2$)$_n$—Y—(CH$_2$)$_m$—X, —(CH$_2$)$_n$—(CF$_2$)$_p$—(CH$_2$)$_m$—X, —(CH$_2$)$_n$—CXH—CH$_3$, —(CH$_2$)$_n$—CXH—CH$_2$—CH$_3$, (CH$_2$)$_q$(CHOH)$_r$(CH$_2$)$_r$—C$_6$H$_4$—(CH$_2$)$_s$—X;

X'=$^{18}$F, $^{123}$I, $^{124}$I, $^{131}$I, O—Z', S—Z', NH—Z', —NZ'Alkyl, CO—Z', CH(OAlkyl)$_2$, CO$_2$—Z', CONH—Z', CONZ'Alkyl, CH═CH—Z' and C≡C—Z';

Z' is dansyl, NH-Cy3, Cy5, Cy5.5, Cy7 or Z' is

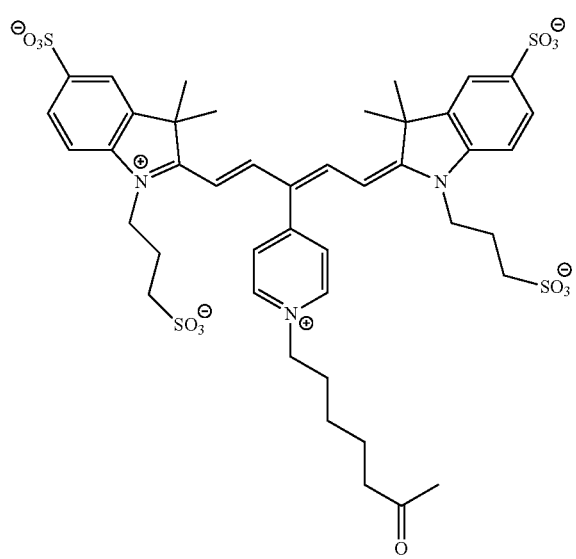

Y'=O, S, SO, SO$_2$, C(O), CH(OH), CH(OAlkyl), CH(OAryl), CH(OHeteroaryl), C(OAlkyl)$_2$, epoxide, vic-diol, vic-acetal, CH═CH and C≡C;

n'=8, 9, 10, 11, 12, 13, 14, 15, 16, 17, 18, 19, and 20, preferably 14, 15 or 16;

m'=2, 3, 4, 5, 6, 7, 8, 9 and 10;

p'=1, 2, 3, 4, and 5;

q'=1, 2, 3, 4, and 5;

r'=0, 1, 2, 3, 4, and 5;

s'=6, 7, 8, 9, and 10;
t'=0 and 1;
$R^{1'}$, $R^{2'}$ are independently H, C(O)Alkyl, C(O)Aryl, C(O)Heteroaryl —$PO_3^{2-}$, and —$P(OH)(O)_2^-$;
$R^{3'}$, $R^{4'}$ are independently H, C(O)Alkyl, C(O)Aryl, C(O)Heteroaryl;
with the proviso that
when
R' is —$(CH_2)_{n'}$—$(CP_2)_{p'}$—$(CH_2)_{m'}$—X' wherein X' is as defined above the sum n'+m'+p' is 12-24 and
when
R' is —$(CH_2)_{n'}$—Y'—$(CH_2)_{m'}$—X' wherein Y' and X' are as defined above the sum n'+m' is 12-24.

In a fifth aspect, the invention is directed to a compound of formula (II) wherein
R'=—$(CH_2)_n CH_2$—X', —$(CH_2)_{m'}$—Y'—$(CH_2)_{m'}$—X', —$(CH_2)_{m'}$—$(CF_2)_{p'}$—$(CH_2)_{m'}$—X', —$(CH_2)_{m'}$—CX'H—$CH_3$, —$(CH_2)_{n'}$—CX'H—$CH_2$—$CH_3$;
X'=$^{18}$F, $^{123}$I, $^{124}$I, $^{131}$I, O—Z', S—Z', NH—Z', —NZ'Alkyl, CO—Z', CH(OAlkyl)$_2$, $CO_2$—Z', CONH—Z'CONZ'Alkyl, CH═CH—Z' and C≡C—Z';
Z' is a dye in particular dansyl, Cy3, Cy5, Cy5.5 and Cy7
Y'═O, S, SO, $SO_2$, C(O), CH(OH), CH(OAlkyl), CH(OAryl), CH(OHeteroaryl), C(OAlkyl)$_2$, epoxide, vic-diol, vic-acetal, CH═CH, C≡C;
n'=8, 9, 10, 11, 12, 13, 14, 15, 16, 17, 18, 19, and 20, preferably 14, 15 or 16;
m'=2, 3, 4, 5, 6, 7, 8, 9 and 10;
p'=1, 2, 3, 4, and 5;
$R^{1'}$, $R^{2'}$ are independently H, C(O)Alkyl, C(O)Aryl, C(O)Heteroaryl —$PO_3^{2-}$, and —$P(OH)(O)_2^-$;
$R^{3'}$, $R^{4'}$ are independently H, C(O)Alkyl, C(O)Aryl and C(O)Heteroaryl; with the proviso that when
R' is —$(CH_2)_{n'}$—$(CF_2)_{p'}$—$(CH_2)_{m'}$—X' wherein X' is as defined above, the sum n'+m'+p' is 12-24 and when
R' is —$(CH_2)_{n'}$—Y'—$(CH_2)_{m'}$—X' wherein Y' and X' are as defined above the sum n'+m' is 12-24.

In another embodiment, R' is —$(CH_2)_n CH_2$—X', X' is as defined above and n is 15 and $R^{1'}$, $R^{2'}$, $R^{3'}$, $R^{4'}$ are as defined above. More preferably, $R^{1'}$, $R^{2'}$, $R^{3'}$, $R^{4'}$ are H.

In a specific embodiment of formula (II), R' is —$(CH_2)_n CH_2$—X' and X' is $^{18}$F, $^{123}$I, $^{124}$I, or $^{131}$I and n' is 14-16, more preferably n' is 15.

In another embodiment, R' is —$(CH_2)_n CH_2$—X', X' is $^{18}$F, n' is 15 and $R^{1'}$, $R^{2'}$, $R^{3'}$, $R^{4'}$ are as defined above. More preferably, $R^{1'}$, $R^{2'}$, $R^{3'}$, $R^{4'}$ are H.

In another embodiment of formula (II), R' is —$(CH_2)_{n'}$—$(CF_2)_{p'}$—$(CH_2)_{m'}$—X', X' is $^{18}$F and the sum n'+m'+p'=14-16.

In a further embodiment, of formula (II), R' is —$(CH_2)_{15}CH_2$—$^{18}$F, $R^{1'}$, $R^{2'}$ are independently H, C(O)Alkyl, C(O)Aryl, C(O)Heteroaryl, —$PO_3^{2-}$, —$P(OH)(O)_2^-$ and $R^{3'}$, $R^{4'}$ are independently H, C(O)Alkyl, C(O)Aryl, C(O)Heteroaryl.

In another embodiment, R' is —$(CH_2)_n CH_2$—X', X' is as defined above and n' is 15 and $R^{1'}$, $R^{2'}$, $R^{3'}$, $R^{4'}$ are as defined above. More preferably, $R^{1'}$, $R^{2'}$, $R^{3'}$, $R^{4'}$ are H.

In yet another embodiment, R' is —$(CH_2)_{15}CH_2$—$^{18}$F, $R^{1'}$ and $R^{2'}$ are independently H, C(O)Alkyl, C(O)Aryl, C(O)Heteroaryl, —$PO_3^{2-}$, —$P(OH)(O)_2^-$, and $R^{3'}$ and $R^{4'}$ are independently H, C(O)Alkyl, C(O)Aryl, C(O)Heteroaryl. More preferably, $R^{1'}$, $R^{2'}$, $R^{3'}$, $R^{4'}$ are H.

In another embodiment, R' is —$(CH_2)_{n'}$—CX'H—$CH_3$, X' is $^{18}$F and $R^{1'}$, $R^{2'}$, $R^{3'}$, $R^{4'}$ are as defined above. More preferably, $R^{1'}$, $R^{2'}$, $R^{3'}$, $R^{4'}$ are H. More preferably, n' is 14, 15 and 16.

In another embodiment, R' is, —$(CH_2)_{n'}$—CX'H—$CH_2$—$CH_3$, X' is $^{18}$F and $R^{1'}$, $R^{2'}$, $R^{3'}$, $R^{4'}$ are as defined above. More preferably, $R^{1'}$, $R^{2'}$, $R^{3'}$, $R^{4'}$ are H. More preferably, n' is 14, 15 and 16.

In another embodiment, R is $(CH_2)_q (CHOH)(CH_2)_{r'}$—$C_6H_4$—$(CH_2)_{s'}$—X, q is 1, r is 0, s is 8 and X is F. Preferably, the substituent —$(CH_2)_{s'}$—X is in para position.

In another embodiment, X' is $^{18}$F.

In an embodiment, the preferred compounds are

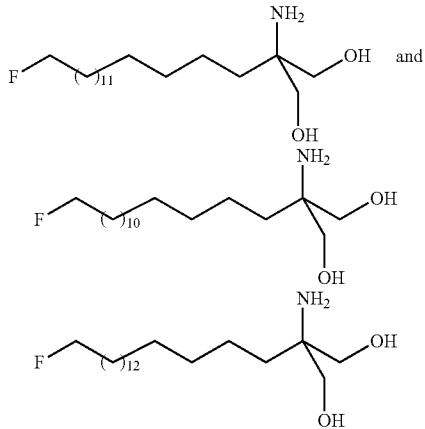

wherein F is $^{18}$F.

The compounds of formula (II) are for use in the diagnosis of human diseases in all settings where S1P and its receptors play a role. These diseases are selected from pain, immunological, inflammatory, neurological, cardiovascular, rheumatic, autoimmune, allergic, infectious, haematological, degenerative, oncological, ophthalmological, metabolic diseases.

The compounds of formula (II) can be used as tracer of S1P receptor in vivo or in vitro imaging using the appropriate imaging instrument. "Imaging instrument" refers to an instrument that can detect the radiations emitted from radiotracers administered to living subjects and may reconstruct the information obtained to provide planar and tomographic images. Such images may reveal the distribution and/or concentration of the radiotracer as a function of time. Preferably, the "imaging instrument" of the present invention refers, but is not limited to, positron emission tomography (PET) or single photon emission computed tomography (SPECT).

Hence, the compounds of formula (II) are used in in vivo imaging in positron emission tomography (PET), single photon emission computed tomography (SPECT) or in fluorescence imaging for the diagnosis of human diseases in all settings where S1P and its receptors play a role wherein said disease are selected from pain, immunological, inflammatory, neurological, cardiovascular, rheumatic, auto-immune, allergic, infectious, haematological, degenerative, oncological, ophthalmological, metabolic diseases.

The compounds of formula (II) are used as in vitro diagnostic agent of human diseases in all settings where S1P and its receptors play a role wherein said diseases are selected from pain, immunological, inflammatory, neurological, cardiovascular, rheumatic, autoimmune, allergic, infectious, haematological, degenerative, oncological, ophthalmological, metabolic diseases.

The present invention, in a further aspect, is directed to a process for preparing the compound of formula (II). The compounds of formula (II) may be prepared by using the compounds of formula (I)'

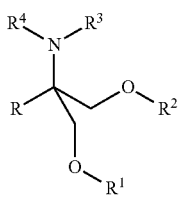

formula (I)′ wherein R, R¹, R², R³ and R⁴ n, m, p and m+n+p n+m are as defined in formula (I), and X is CH=CH₂, C≡CH, N₃, OH, OTs, OMs, OTf, SH, SO, SO₂, NH₂.

For example, the compounds of formula (I) may be reacted with a suitable reagent to form the compounds of formula (II).

For example, the compounds of formula (I') may be reacted with a suitable reagent to form the compounds of formula (II). Hence, the compounds of formula (I') are intermediates in the synthesis of the compounds of formula (II).

When the compounds of formula (I) or (II) have one or more asymmetric centers in the molecule, the present invention is to be understood as embracing the various optical isomers, as well as racemates, diastereoisomers and mixtures thereof. Compounds of formula (I) or (II), when the carbon atom bearing the amino group ($NR^3R^4$ or $NR^{3'}R^{4'}$) is asymmetric, have preferably the S-configuration at this carbon atom.

The compounds of formula (I) or (II) may exist in free or salt form. Examples of pharmaceutically acceptable salts of the compounds of the formula (I) or (II) include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the present invention encompass hydrate and solvate forms.

5. DEFINITIONS

As herein defined, "autoimmune diseases" include, but are not limited to, multiple sclerosis, systemic lupus erythematosus (SLE), arthritis, rheumatoid arthritis, diabetes, (e.g. type I diabetes mellitus, type II adult onset diabetes mellitus), uveitis.

As herein defined, "cardiovascular diseases" include, but are not limited to, hypertension, heart rate dysregulation.

As herein defined, the term "alkyl" includes $C_1$-$C_8$ alkyl, in particular $C_1$-$C_4$ alkyl, such as methyl, ethyl, n-propyl, isopropyl, butyl, iso-butyl, t-butyl, pentyl, hexyl, etc. Alkyl maybe optionally substituted with a group selected from halo, preferably F, OH, amino, $C_1$-$C_6$ alkylamino.

As herein defined, the term "aryl" includes mono or polycyclic rings having an aromatic character such as phenyl, naphthyl, indenyl, biphenyl. "Aryl" may be optionally substituted aryl. Preferably, the substituents are selected from halogen, preferably F, $C_1$-$C_8$ alkyl, OH, $C_1$-$C_8$ alkoxy, amino, $C_1$-$C_8$ alkylamino.

As herein defined the term "hetero-aryl" is a 5- or 6-membered heteroaryl having, in the ring, 1 to 4 heteroatoms selected from N, O, S and includes for example furanyl or pyrrolyl, imidazolyl, pyrazolyl, triazolyl, tetrazolyl, oxazolyl, pyridyl, pyrazinyl, pyrimidinyl. Hetero-aryl may be optionally substituted aryl. Preferably, the substituents are selected from halogen, preferably F, $C_1$-$C_8$ alkyl, OH, $C_1$-$C_8$ alkoxy amino, $C_1$-$C_8$ alkylamino.

As herein defined, the term "vic-diol" refers to "vicinal diol" which is a diol with two hydroxyl groups in vicinal positions that is attached to adjacent atoms.

As herein defined, the term "vic-acetal" refers to "vicinal acetal" which is an acetal formed from two hydroxyl groups in vicinal positions, that are attached to an adjacent atom coming from the carbonyl group of an aldehyde or a ketone forming a 1,3-dioxolane.

6. EXAMPLES

1. Synthesis of 2-Amino-2-hexadecylpropane-1,3-diol (SSS BHI 1091)

1.1 Diethyl 2-acetamidomalonate

Diethyl 12-aminomalonate hydrochloride (1.69 g, 8.0 mmol) and triethylamine (3.4 mL, 24 mmol, 3.0 eq.) were dissolved in dichloromethane (120 mL) at 0° C. Then acetylchloride (0.57 mL, 8.0 mmol, 1.0 eq.) was added under stirring and stirring was continued overnight while the mixture was allowed to warm up to r.t. The mixture was diluted with dichloromethane (100 mL) and washed with 1 M HCl (3×60 mL). The aqueous phase was extracted with dichloromethane (2×60 mL) and the combined organic layer was dried over MgSO₄. After evaporation of the solvent in vacuo the product was isolated as a pure white solid. Yield: 1.68 g (96%).

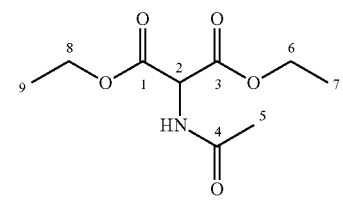

M.p.: 96° C. (lit. 97° C.)
¹H NMR (300 MHz, CDCl₃): δ [ppm]: 1.30 (t, $^3J_{H,H}$=7.1 Hz, 6H, 7-CH₃, 9-CH₃), 2.08 (s, 3H, 5-CH₃), 4.27 (m, 4H, 6-CH₂, 8-CH₂), 5.18 (d, $^3J_{H,H}$=7.1 Hz, 1H, 2-CH), 6.67 (d, $^3J_{H,H}$=5.7 Hz, 1H, 2-NH).
¹³C-NMR (75 MHz, CDCl₃) δ [ppm]: 14.0 (q, C-7, C-9), 22.8 (q, C-5), 56.5 (d, C-2), 62.6 (t, C-6, C-8), 166.5 (s, C-1, C-3), 169.9 (s, C-4).
Exact mass (ESI⁺): C₉H₁₅NO₅+Na⁺: calcd. 240.0842. found 240.0824.
Alternatively, diethyl 2-aminomalonate hydrochloride (21.4 g, 100 mmol) and triethylamine (56 mL, 400 mmol, 4.0 eq.) were dissolved in dichloromethane (500 mL) and stirred with acetic anhydride (9.5 mL, 100 mmol, 1.0 eq.) at 0° C. and overnight at r.t. The mixture was washed with brine (2×200 mL) and dried over MgSO₄. The organic phase was filtered through a short silica gel column I (6×6 cm, dichloromethane). The product 1 was isolated as a white crystalline solid. Yield: 22.08 g (100%); 99% purity (GC).
Refs.: Synthesis according to T. Seitz, J. Baudoux, H. Bekolo, D. Cahard, J.-C. Plaquevent, M.-C. Lasne, J. Rouden, *Tetrahedron* 2006, 62, 6155-6165.
M.p. T. N. Ghosh, *J. Indian Chem. Soc.* 1955, 32, 17-22.

1.2 Diethyl 2-(tert-butoxycarbonyl)amidomalonate

Diethyl 2-aminomalonate hydrochloride (2.535 g, 12.0 mmol) was dissolved in a mixture of 1 M NaOH (12 mL) and 1,4-dioxane (10 mL) and a solution of Boc-anhydride (2.54 g, 12.0 mmol, 1.0 eq.) in 1,4-dioxane (5 mL) was added dropwise at 5° C. Subsequently, the mixture was stirred at r.t. for 24 h. Dioxane was removed in vacuo and the residue was dissolved in ethyl acetate. After phase separation, the organic layer was washed with 1 M HCl (3×50 mL) and dried over $Na_2SO_4$. The solvent was removed in vacuo and the crude product was purified by column chromatography with silica gel (cyclohexane/ethyl acetate, 6:1). The product was isolated as a colourless oil. Yield: 3.009 g (91%).

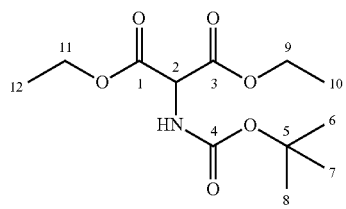

2

$^1$H NMR (300 MHz, CDCl$_3$): δ [ppm]: 1.30 (t, $^3J_{H,H}$=7.2 Hz, 6H, 10-CH$_3$, 12-CH$_3$), 1.45 (s, 9H, 6-CH$_3$, 7-CH$_3$, 8-CH$_3$), 4.27 (m, 4H, 9-CH$_2$, 11-CH$_2$), 4.94 (d, $^3J_{H,H}$=7.7 Hz, 1H, 2-CH), 5.63 (d, $^3J_{H,H}$=7.8 Hz, 1H, 2-NH).

$^{13}$C-NMR (101 MHz, CDCl$_3$) δ [ppm]: 14.0 (q, C-10, C-12), 28.2 (q, C-6, C-7, C-8), 57.5 (d, C-2), 62.4 (t, C-9, C-11), 80.5 (s, C-5), 154.8 (s, C-4), 166.6 (s, C-1, C-3).

Exact mass (ESI$^+$): $C_{12}H_{21}NO_6+Na^+$: calcd. 298.1261. found 298.1244.

Ref.: $^1$H NMR: H. Schneider, G. Sigmund, B. Schricker, K. Thirring, H. Berner, *J. Org. Chem.* 1993, 58, 683-689.

1.3 Diethyl 2-acetamido-2-hexadecylmalonate

Diethyl 2-acetamidomalonate 1 (0.666 g, 3.07 mmol), caesiumcarbonate (1.981 g, 6.1 mmol, 2.0 eq.) and iodohexadecane (2.114 g, 6.0 mmol, 2.0 eq.) were suspended in acetonitrile (45 mL) and refluxed with microwave irradiation (100 W) for 1 h (4×15 min). After cooling to r.t. the solid was filtered and the solvent was removed in vacuo. After column chromatography with silica gel (20×6 cm, cyclohexane/ethyl acetate, 4:1 to 3:1) the product was isolated as a white solid. Yield: 1.106 g (78%), purity 94% (GC).

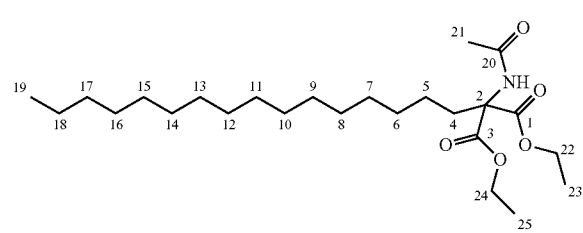

3

M.p.: 67° C. (lit. 65-67° C.).

$^1$H NMR (300 MHz, CDCl$_3$): δ [ppm]: 0.88 (m, 3H, 19-CH$_3$), 1.23-1.33 (m, 34H, 5-CH$_2$ to 18-CH$_2$, 23-CH$_3$, 25-CH$_3$), 2.04 (s, 3H, 21-CH$_3$), 2.30 (m, 2H, 4-CH$_2$), 4.24 (q, $^3J_{H,H}$=7.1 Hz, 4H, 22-CH$_2$, 24-CH$_2$), 6.79 (s, 1H, 2-NH).

$^{13}$C NMR (75 MHz, CDCl$_3$) δ [ppm]: 14.1 (q, C-23, C-25), 14.2 (q, C-19), 22.8 (q, C-21), 23.2 (t, C-18), 23.7 (t, C-5), 29.4, 29.5, 29.6, 29.7, 29.8 (t, C-6 to C-16), 32.0 (t, C-17), 32.2 (t, C-4), 62.5 (t, C-22, C-24), 66.7 (s, C-2), 168.4 (s, C-1, C-3), 169.0 (s, C-20).

Exact mass (ESI$^+$): $C_{25}H_{47}NO_5+Na^+$: calcd. 464.3346. found 464.3356.

Refs.: $^1$H NMR C J. Zhu, H. Galons, P. Pigeon, A. Loupy, *Synth. Commun.* 1995, 25, 215-218.

1.4 Diethyl 2-(tert-butoxycarbonyl)amido-2-hexadecylmalonate

Diethyl N-Boc-2-amidomalonate 2 (10.953 g, 39.79 mmol), caesiumcarbonate (16.852 g, 51.72 g, 1.3 eq.) and iodohexadecane (16.3 mL, 18.224 g, 51.72 mmol, 1.3 eq.) were suspended in acetonitrile (160 mL) and refluxed for 5 h. After cooling to r.t. the reaction mixture was adsorbed at silica gel and purified by column chromatography with silica gel (25×6 cm, cyclohexane/ethyl acetate, 20:1). The product 4 was isolated as a white solid.

Yield: 15.614 g (79%).

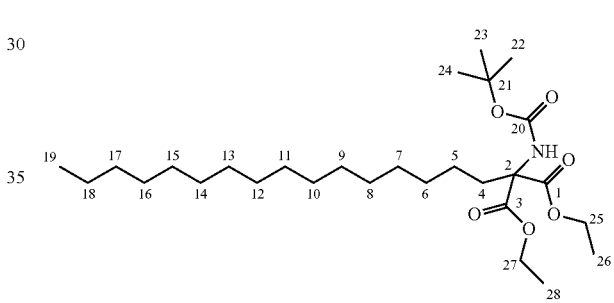

4

M.p.: 50° C.

$^1$H-NMR (400 MHz, CDCl$_3$) δ [ppm]: 0.88 (t, $^3J_{H,H}$=6.7 Hz, 3H, 19-CH$_3$), 1.23-1.28 (m, 34H, 5-CH$_2$ to 18-CH$_2$, 26-CH$_3$, 28-CH$_3$), 1.43 (s, 9H, 22-CH$_3$, 23-CH$_3$, 24-CH$_3$), 2.26 (m, 2H, 4-CH$_2$), 4.23 (m, 4H, 25-CH$_2$, 27-CH$_2$), 5.93 (s, 1H, 2-NH).

$^{13}$C-NMR (101 MHz, CDCl$_3$) δ [ppm]: 14.1 (q, C-19), 14.2 (q, C-26, C-28), 22.8 (t, C-18), 23.4 (t, C-5), 28.3 (q, C-22, C-23, C-24), 29.3, 29.4, 29.5, 29.6, 29.7, 29.8 (t, C-6 to C-16), 32.0 (t, C-17), 32.6 (t, C-4), 62.3 (t, C-25, C-27), 66.6 (s, C-2), 80.1 (s, C-21), 153.9 (s, C-20), 168.5 (s, C-1, C-3).

Exact mass (ESI$^+$): $C_{28}H_{53}NO_6+Na^+$: calcd. 522.3765. found 522.3758.

1.5 N-[1,1-bis(hydroxymethyl)heptadecyl]acetamide

The diester 3 (0.256 g, 0.58 mmol) was dissolved in THF (5 mL) and reacted with lithium chloride (0.115 g, 2.7 mmol, 4.7 eq.) and sodium borohydride (0.102 g, 2.7 mmol, 4.7 eq.). The mixture was cooled to 0° C. and treated with ethanol (10 mL). After stirring for one more hour at 0° C. the mixture was stirred at r.t. overnight. After cooling to 0° C. 10% citric acid was added to adjust pH 4. THF was removed and the residue was dissolved in water (10 mL). The aqueous phase was extracted with dichloromethane (4×20 mL). The organic layer was washed with water and dried over $Na_2SO_4$. The solvent was removed and the residue was purified by column chromatography (silica gel, 8×4 cm, cyclohexane/ethyl acetate, 1:4). The product was isolated as a white solid. Yield: 0.155 g (75%).

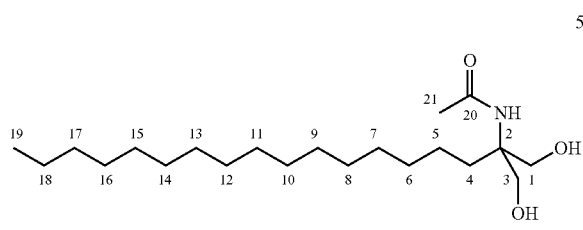 [SMILES: CCCCCCCCCCCCCCCCC(CO)(CO)NC(C)=O]

M.p.: 92° C.

$^1$H-NMR (300 MHz, CDCl$_3$, CD$_3$OD) δ [ppm]: 0.88 (t, $^3J_{H,H}$=6.4 Hz, 3H, 19-CH$_3$), 1.23-1.28 (m, 28H, 5-CH$_2$ to 18-CH$_2$), 1.65 (m, 2H, 4-CH$_2$), 2.03 (s, 3H, 21-CH$_3$), 3.59 (d, $^2J_{H,H}$=11.6 Hz, 2H, 1-CH$_2$, 3-CH$_2$), 3.69 (d, $^2J_{H,H}$=11.5 Hz, 2H, 1-CH$_2$, 3-CH$_2$).

$^{13}$C-NMR (75 MHz, CDCl$_3$, CD$_3$OD) δ [ppm]: 13.8 (q, C-19), 22.5 (q, C-21), 23.0 (t, C-18), 23.1 (t, C-5), 29.2, 29.5 (t, C-7 to C-16), 30.0 (t, C-6), 31.7 (t, C-17), 32.1 (t, C-4), 61.3 (s, C-2), 64.6 (t, C-1, C-3), 172.5 (s, C-20).

Exact mass (ESI$^+$): C$_{21}$H$_{43}$NO$_3$+H$^+$: calcd. 358.3316. found 358.3322. C$_{21}$H$_{43}$NO$_3$+Na$^+$: calcd. 380.3135. found 380.3141.

1.6 N-[1,1-bis(hydroxymethyl)heptadecyl]-tert-butylcarbamate

The diester 4 (15.019 g, 30.07 mmol) was dissolved in THF (100 mL) and reacted with lithium chloride (6.376 g, 150.4 mmol, 5.0 eq.) and sodium borohydride (5.688 g, 150.4 mmol, 5.0 eq.). The mixture was cooled to 0° C. and treated with ethanol (200 mL). After stirring for one more hour at 0° C. the mixture was stirred at r.t. overnight. After cooling to 0° C. 10% citric acid was added to adjust pH 4. THF was removed and the residue was dissolved in water (100 mL). The aqueous phase was extracted with dichloromethane (4×100 mL). The organic layer was washed with water and dried over Na$_2$SO$_4$. The solvent was removed and the residue was purified by column chromatography (silica gel, 26×6 cm, cyclohexane/ethyl acetate, 10:1 to pure ethyl acetate). The product was isolated as a white solid. Yield: 12.282 g (98%).

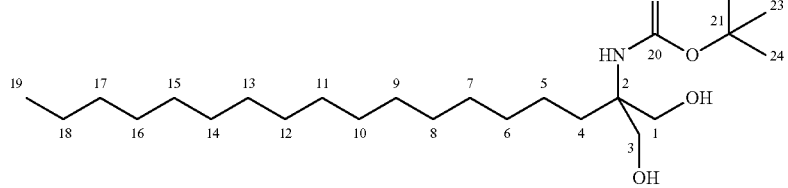

M.p.: 79° C.

$^1$H-NMR (400 MHz, CDCl$_3$) δ [ppm]: 0.87 (m, 3H, 19-CH$_3$), 1.25-1.31 (m, 28H, 5-CH$_2$ to 18-CH$_2$), 1.44 (s, 9H, 22-CH$_3$, 23-CH$_3$, 24-CH$_3$), 1.54 (m, 2H, 4-CH$_2$), 3.58 (d, $^2J_{H,H}$=11.5 Hz, 2H, 1-CH$_2$, 3-CH$_2$), 3.81 (d, $^2J_{H,H}$=11.5 Hz, 2H, 1-CH$_2$, 3-CH$_2$), 3.88 (s, 2H, 1-OH, 3-OH), 5.01 (s, 1H, 2-NH).

$^{13}$C-NMR (101 MHz, CDCl$_3$) δ [ppm]: 14.2 (q, C-19), 22.8 (t, C-18), 23.1 (t, C-5), 28.4 (q, C-22, C-23, C-24), 29.5, 29.7, 29.8 (t, C-6 to C-16), 30.2 (t, C-17), 32.0 (t, C-4), 59.4 (s, C-2), 66.5 (t, C-1, C-3), 80.2 (s, C-21), 156.7 (s, C-20).

Exact mass (ESI$^+$): C$_{24}$H$_{49}$NO$_4$+Na$^+$: calcd. 438.3554. found 438.3550. (C$_{24}$H$_{49}$NO$_4$)$_2$+Na$^+$: calcd. 853.7215. found 853.7197.

1.7 2-Amino-2-hexadecylpropane-1,3-diol (SSS BHI 1091)

The amide 5 (0.155 g, 0.43 mmol) was dissolved in methanol (8 mL) and treated with 1 M NaOH (0.8 mL 0.8 mmol, 1.8 eq.). The reaction mixture was refluxed for 5 h. After cooling to r.t. the mixture was extracted with dichloromethane (4×10 mL). The organic layer was washed with water and dried over Na$_2$SO$_4$ and the solvent was evaporated. The residue was recrystallized from ethyl acetate to give a white solid. Yield: 0.132 g (97%).

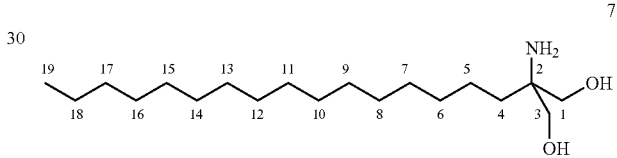

M.p.: 91-93° C.

$^1$H-NMR (300 MHz, CD$_3$OD) δ [ppm]: 0.90 (m, 3H, 19-CH$_3$), 1.25-1.35 (m, 30H, 4-CH$_2$ to 18-CH$_2$), 3.38 (d, $^2J_{H,H}$=10.8 Hz, 2H, 1-CH$_2$, 3-CH$_2$), 3.43 (d, $^2J_{H,H}$=10.8 Hz, 2H, 1-CH$_2$, 3-CH$_2$).

$^{13}$C-NMR (75 MHz, CD$_3$OD) δ [ppm]: 14.5 (q, C-19), 23.8 (t, C-18), 23.9 (t, C-5), 30.5, 30.8 (t, C-7 to C-16), 31.7 (t, C-6), 33.1 (t, C-17), 35.3 (t, C-4), 56.6 (s, C-2), 66.5 (t, C-1, C-3).

Exact mass (ESI$^+$): C$_{19}$H$_{41}$NO$_2$+H$^+$: calcd. 316.3210. found 316.3205. C$_{19}$H$_{41}$NO$_2$+Na$^+$: calcd. 338.3030. found 338.3026.

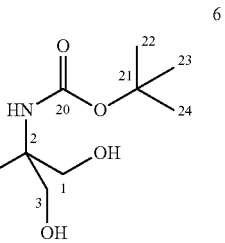

Alternatively, the Boc-protected aminodiol 6 (3.474 g, 8.36 mmol) was dissolved in dichloromethane (75 mL), cooled down to 0° C. and treated with trifluoroacetic acid (TFA) (84 mL). The mixture was stirred at r.t. overnight. All volatile components were removed in vacuo. Then methanol (10 mL) was added and evaporated again. In order to remove traces of TFA this procedure was repeated two more times. The residue was dissolved in methanol (10 mL) and 1 M NaOH (100 mL). The aqueous phase was extracted with dichloromethane (3×100 mL). The combined organic layer was washed with water and dried over $Na_2SO_4$, the solvent was removed and the crude product was recrystallized from ethyl acetate to give the product as a white solid. Yield: 2.441 g (93%).

Ref.: The NMR spectrum is similar to that of the corresponding hydrochloride in T. Fujita, R. Hirose, M. Yoneta, S. Sasaki, K. Inoue, M. Kiuchi, S. Hirase, K. Chiba, H. Sakamoto, M. Arita, *J. Med. Chem.* 1996, 39, 4451-4459.

2. Synthesis of the 2-Fluoromethyl Substituted Compound

2.1 2-Amino-2-(fluoromethyl)octadecan-1-ol (SSS 535)

The aminodiol 7 (0.316 g, 1.0 mmol) obtained as in example 1.7 above was suspended in dichloromethane (15 mL) and cooled down to −78° C. To this suspension diethylaminosulfur trifluoride (DAST) (0.13 mL, 1.0 mmol, 1.0 eq.) was dropped slowly with stirring at −78° C. The mixture was allowed to warm up to −10° C. overnight and neutralized with saturated sodium bicarbonate solution (30 mL). The phases were separated and the aqueous phase was extracted with dichloromethane (4×25 mL). The combined organic phases were dried over $Na_2SO_4$ and the solvent was removed in vacuo. The residue was purified by column chromatography (silica gel, 10×4 cm, dichloromethane/methanol, gradient 30:1 to 6:1) and the product was isolated as yellowish solid. Yield: 0.036 g (0.11 mmol, 11%).

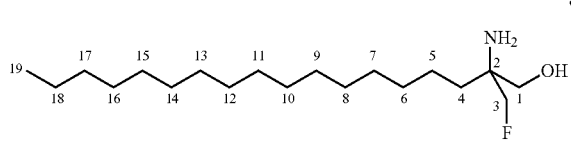

M.p.: 52° C.

$^1$H-NMR (300 MHz, $CDCl_3$) δ [ppm]: 0.87 (t, $^3J_{H,H}$=6.6 Hz, 3H, 19-$CH_3$), 1.21-1.34 (m, 28H, 5-$CH_2$ to 18-$CH_2$), 1.46 (m, 2H, 4-$CH_2$), 3.49 (m, 2H, 1-$CH_2$), 4.32 (d, $^2J_{H,F}$=47.5 Hz, 2H, 3-$CH_2$).

$^{13}$C-NMR (75 MHz, $CDCl_3$) δ [ppm]: 14.2 (t, C-18), 22.8 (q, C-19), 29.5, 29.7, 29.8 (t, C-5 to C-16), 30.4 (t, C-4), 32.1 (t, C-17), 56.2 (d, $^2J_{C,F}$=16.6 Hz, C-2), 65.2 (t, C-1), 86.3 (dt, $^1J_{C,F}$=174.3 Hz, C-3).

$^{19}$F-NMR (282 MHz, $CDCl_3$) δ [ppm]: −230.4 (t, $^2J_{H,F}$=47.3 Hz, 1F, 3-$CH_2F$).

Exact mass (ESI$^+$): $C_{19}H_{40}FNO+H^+$: calcd. 318.3167. found 318.3167. $C_{19}H_{40}FNO+Na^+$: calcd. 340.2986. found 340.2991.

3. Synthesis of the 4-Fluoro Compounds

3.1 2-Fluoro-1-iodohexadecane

Hexadec-1-ene (6.23 mL, 4.879 g, 20.0 mmol, 92% purity) and triethylamine trishydrofluoride (10 mL, 50.0 mmol, 2.5 eq.) were dissolved in dichloromethane (40 mL) and N-iodosuccinimide (NIS) (4.950 g, 22.0 mmol, 1.1 eq.) in dichloromethane (40 mL) was added under stirring at 0° C. The mixture was stirred at r.t. overnight. Then the mixture was poured into ice water (40 mL) and treated with conc. ammonia solution until alkaline pH was reached. The phases were separated and the aqueous phase was extracted with dichloromethane (3×50 mL). The combined organic layer was washed with 2 M HCl (80 mL), 5% sodium bicarbonate solution and water. After drying over $MgSO_4$ and evaporation of the solvent, the crude product was purified by column chromatography (silica gel, 3×6 cm, cyclohexane) and recrystallized from ethyl acetate. The iodofluoride 9 was isolated as a white, crystalline solid. Yield: 5.766 g (15.6 mmol, 78%).

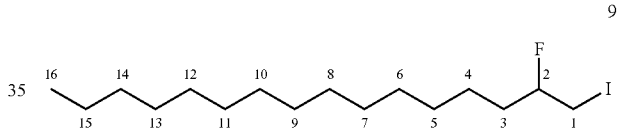

M.p.: 50-52° C.

$^1$H-NMR (400 MHz, $CDCl_3$) δ [ppm]: 0.87 (m, 3H, 16-$CH_3$), 1.18-1.46 (m, 24H, 4-$CH_2$ to 15-$CH_2$), 1.71 (m, 2H, 3-$CH_2$), 3.31 (m, 2H, 1-$CH_2$), 4.44 (m, 1H, 2-CH).

$^{13}$C-NMR (101 MHz, $CDCl_3$) δ [ppm]: 7.2 (dt, $^2J_{C,F}$=24.6 Hz, C-1), 14.3 (q, C-16), 22.8 (t, C-15), 24.9 (dt, $^3J_{C,F}$=4.2 Hz, C-4), 29.4, 29.5, 29.6, 29.7, 29.8 (t, C-5 to C-13), 32.1 (t, C-14), 35.0 (dt, $^2J_{C,F}$=20.5 Hz, C-3), 92.3 (dd, $^1J_{C,F}$=174.6 Hz, C-2).

$^{19}$F-NMR (282 MHz, $CDCl_3$) δ [ppm]: −171.3 (m, 1F, 2-CHF).

3.2 Diethyl 2-acetamido-2-(2-fluorohexadecyl)malonate

The iodofluoride 9 (0.370 g, 1.0 mmol), the 2-amidomalonate 1 (0.220 g, 1.0 mmol, 1.0 eq.) (obtained following the procedure of example 1.1 above) and caesium carbonate (1.095 g, 3.4 mmol, 3.4 eq.) were suspended in acetonitrile (20 mL) and refluxed for 5 h. After cooling to r.t. and partial removal of the solvent, the residue was adsorbed at silica gel (2 g) and purified by column chromatography (silica gel, 11×4 cm, cyclohexane/ethyl acetate, 4:1) to give the product as a white solid. Yield: 0.214 g (47%).

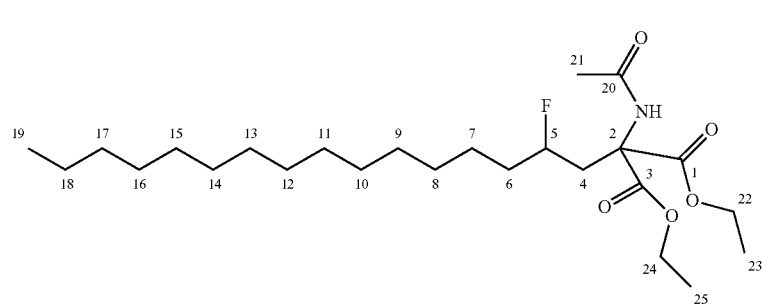

M.p.: 71-73° C.

$^1$H-NMR (300 MHz, CDCl$_3$) δ [ppm]: 0.88 (m, 3H, 19-CH$_3$), 1.21-1.45 (m, 32H, 6-CH$_2$ to 18-CH$_2$, 23-CH$_3$, 25-CH$_3$), 2.06 (s, 3H, 21-CH$_3$), 2.68 (m, 2H, 4-CH$_2$), 4.23 (m, 4H, 22-CH$_2$, 24-CH$_2$), 4.56 (m, 1H, 5-CH), 7.07 (s, 1H, 2-NH).

$^{13}$C-NMR (75 MHz, CDCl$_3$) δ [ppm]: 13.8 (q, C-19), 14.0 (q, C-23 or C-25), 14.1 (q, C-23 or C-25), 22.7 (t, C-18), 23.0 (q, C-21), 24.9 (dt, $^3J_{C,F}$=4.5 Hz, C-7), 29.4, 29.5, 29.6, 29.7 (t, C-8 to C-16), 31.9 (t, C-17), 35.2 (dt, $^2J_{C,F}$=20.2 Hz, C-6), 38.0 (dt, $^2J_{C,F}$=19.1 Hz, C-4), 62.3 (t, C-22 or C-24), 62.9 (t, C-22 or C-24), 64.3 (s, C-2), 90.6 (dt, $^1J_{C,F}$=166.4 Hz, C-5), 167.4 (s, C-1 or C-3), 168.5 (s, C-1 or C-3), 169.4 (s, C-20).

$^{19}$F-NMR (282 MHz, CDCl$_3$) δ [ppm]: −181.2 (m, 1F, 5-CHF).

Exact mass (ESI$^+$): C$_{25}$H$_{46}$FNO$_5$+Na$^+$: calcd. 482.3252. found 482.3255. (C$_{25}$H$_{46}$FNO$_5$)$_2$+Na$^+$: calcd. 941.6612. found 941.6611.

3.3 N-(4-Fluoro-1-hydroxy-2-(hydroxymethyl)octadecan-2-yl)acetamide

The diester 10 (1.336 g, 2.90 mmol) was dissolved in THF (15 mL) and reacted with lithium chloride (0.615 g, 14.5 mmol, 5.0 eq.) and sodium borohydride (0.549 g, 14.5 mmol, 5.0 eq.). The mixture was cooled to 0° C. and treated with ethanol (30 mL). After stirring for one more hour at 0° C. the mixture was stirred at r.t. overnight. After cooling to 0° C. 10% citric acid was added to adjust pH 4. THF was removed and the residue was dissolved in water (50 mL). The aqueous phase was extracted with dichloromethane (4×30 mL). The organic layer was washed with water and dried over Na$_2$SO$_4$. The solvent was removed and the residue was purified by column chromatography (silica gel, 18×4 cm, cyclohexane/ethyl acetate, 1:3). The product was isolated as a white solid. Yield: 0.840 g (77%).

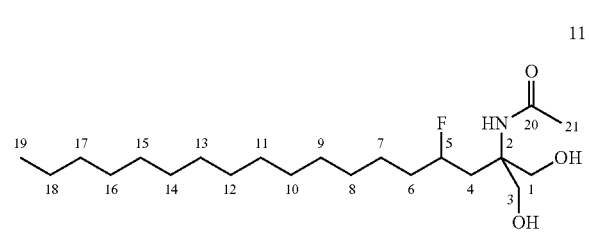 [SMILES: CCCCCCCCCCCCCCC(F)CC(CO)(CO)NC(C)=O]

M.p.: 95-96° C.

$^1$H-NMR (300 MHz, CDCl$_3$) δ [ppm]: 0.88 (m, 3H, 19-CH$_3$), 1.22-1.50 (m, 24H, 7-CH$_2$ to 18-CH$_2$), 1.73 (m, 2H, 6-CH$_2$), 2.03 (s, 3H, 21-CH$_3$), 2.21 (m, 2H, 4-CH$_2$), 3.68 (m, 4H, 1-CH$_2$, 3-CH$_2$), 4.74 (m, 1H, 5-CH), 6.50 (s, 1H, 2-NH).

$^{13}$C-NMR (75 MHz, CDCl$_3$) δ [ppm]: 14.2 (q, C-19), 22.8 (q, C-21), 24.1 (t, C-18), 25.0 (dt, $^3J_{C,F}$=4.8 Hz, C-7), 29.5, 29.6, 29.7, 29.8 (t, C-8 to C-16), 32.0 (t, C-17), 36.2 (dt, $^2J_{C,F}$=21.1 Hz, C-6), 37.5 (dt, $^2J_{C,F}$=19.1 Hz, C-4), 60.9 (d, $^3J_{C,F}$=1.7 Hz, C-2), 65.0 (dt, $^4J_{C,F}$=1.7 Hz, C-1 or C-3), 66.2 (t, C-1 or C-3), 92.6 (dt, $^1J_{C,F}$=162.9 Hz, C-5), 172.0 (s, C-20).

$^{19}$F-NMR (282 MHz, CDCl$_3$) δ [ppm]: −176.67 (m, 1F, 5-CHF).

Exact mass (ESI$^+$): C$_{21}$H$_{42}$FNO$_3$+H$^+$: calcd. 376.3221. found 376.3220. C$_{21}$H$_{42}$FNO$_3$+Na$^+$: calcd. 398.3041. found 398.3040.

3.4 2-Amino-2-(2-fluorohexadecyl)propan-1,3-diol (SSS 517)

The amidodiol 11 (0.400 g, 1.06 mmol) was dissolved in methanol (15 mL) and treated with 1 M NaOH (19 mL 1.90 mmol, 1.8 eq.). The reaction mixture was refluxed for 5 h. After cooling to r.t. the mixture was extracted with dichloromethane (4×15 mL). The organic layer was washed with water and dried over Na$_2$SO$_4$ and the solvent was evaporated. The residue was recrystallized from ethyl acetate to give a white solid. Yield: 0.206 g (58%).

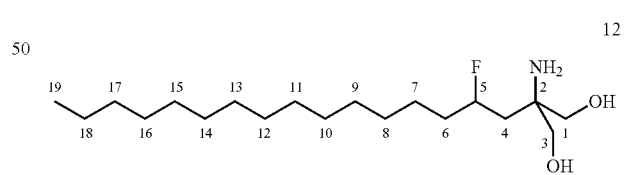

M.p.: 96-98° C.

$^1$H-NMR (300 MHz, CDCl$_3$, CD$_3$OD) δ [ppm]: 0.88 (t, $^3J_{H,H}$=6.4 Hz, 3H, 19-CH$_3$), 1.21-1.79 (m, 28H, 4-CH$_2$, 6-CH$_2$ to 18-CH$_2$), 3.50 (m, 4H, 1-CH$_2$, 3-CH$_2$), 4.79 (m, 1H, 5-CH).

$^{13}$C-NMR (75 MHz, CDCl$_3$, CD$_3$OD) δ [ppm]: 13.4 (q, C-19), 22.3 (t, C-18), 24.6 (dt, $^3J_{C,F}$=4.6 Hz, C-7), 29.0, 29.1, 29.2 (t, C-8 to C-16), 31.5 (t, C-17), 36.0 (dt, $^2J_{C,F}$=20.8 Hz, C-6), 38.7 (dt, $^2J_{C,F}$=19.8 Hz, C-4), 55.1 (s, C-2), 65.2 (t, C-1 or C-3), 65.6 (t, C-1 or C-3), 91.4 (dt, $^1J_{C,F}$=165.1 Hz, C-5).

$^{19}$F-NMR (282 MHz, CDCl$_3$, CD$_3$OD) δ [ppm]: −178.3 (m, 1F, 5-CHF).

Exact mass (ESI$^+$): C$_{19}$H$_{40}$FNO$_2$+H$^+$: calcd. 334.3116. found 334.3110. C$_{19}$H$_{40}$FNO$_2$+Na$^+$: calcd. 356.2935. found 356.2936.

3.5 2-Amino-2-(2-fluorohexadecyl)propan-1,3-diol hydrochloride (SSS 564)

The aminodiol 12 (50 mg, 0.15 mmol) was dissolved in methanol (13 mL) and treated with 4 M HCl (24 mL) until no more solid was precipitated. After standing overnight the precipitate was filtrated, washed with water (5 mL) and n-hexane/ethyl acetate (v/v, 1/1, 5 mL) and dried in high vacuo. Yield: 37 mg (67%)

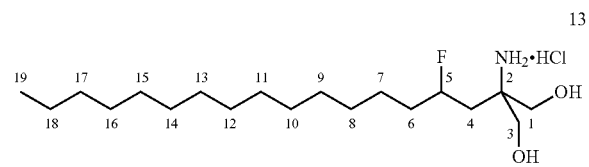

13

M.p.: 108-110° C.
$^1$H-NMR (300 MHz, CD$_3$OD) δ [ppm]: 0.90 (m, 3H, 19-CH$_3$), 1.29-2.02 (m, 28H, 4-CH$_2$, 6-CH$_2$ to 18-CH$_2$), 3.69 (m, 4H, 1-CH$_2$, 3-CH$_2$), 4.76 (m, 1H, 5-CH).
$^{19}$F-NMR (282 MHz, CD$_3$OD) δ [ppm]: −178.1 (m, 1F, 5-CHF).

Exact mass (ESI$^+$): C$_{19}$H$_{41}$FNO$_2$$^+$: calcd. 334.3116. found 334.3118.

4. Synthesis of the ω-Fluoro Substituted Compounds of the Invention

4.1 Hexadecane-1,16-diol

Under an argon atmosphere, 16-Hexadecanolide (4.860 g, 18.5 mmol) in THF (80 mL) was added with stirring to a suspension of lithium aluminium hydride (1.280 g, 33.7 mmol, 1.8 eq.) in THF (160 mL) at 0° C. Stirring was continued at this temperature for 1 h and for 3 more hours at r.t. Potassium sodium tartrate solution was carefully dropped to this mixture with stirring. The phases were separated and the aqueous phase was extracted with diethyl ether (3×100 mL). The combined organic layer was dried over MgSO$_4$. After evaporation of the solvent, the product was isolated as a white solid, which was used for the next step without purification. Yield: 4.598 g (96%).

14

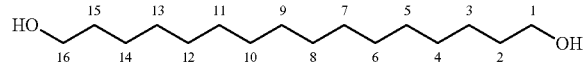

M.p.: 93° C.
$^1$H-NMR (300 MHz, CD$_3$OD, CDCl$_3$) δ [ppm]: 1.28-1.37 (m, 24H, 3-CH$_2$ to 14-CH$_2$), 1.53 (m, 4H, 2-CH$_2$, 15-CH$_2$), 3.56 (t, $^3J_{H,H}$=6.8 Hz, 4H, 1-CH$_2$, 16-CH$_2$).

$^{13}$C-NMR (75 MHz, CD$_3$OD, CDCl$_3$) δ [ppm]: 26.3 (t, C-3, C-14), 30.0, 30.1, 30.2 (t, C-4 to C-13), 33.0 (t, C-2, C-15), 62.7 (t, C-1, C-16).

Refs.: Synthesis according to C. Girlanda-Junges, F. Keyling-Bilger, G. Schmitt, B. Luu, *Tetrahedron* 1998, 54, 7735-7748.

$^1$H-NMR spectroscopic data agree with those given by: S. Mangaleswaran, N. P. Argade, *J. Org. Chem.* 2001, 66, 5259-5261.

4.2 16-Bromohexadecan-1-ol

The diol 14 (1.047 g, 4.05 mmol) was dissolved in cyclohexane (30 mL) and vigorously stirred with 48% HBr (0.5 mL, 4.46 mmol, 1.1 eq.). The mixture was refluxed for 6 h, diluted with water (50 mL) and the phases were separated. The aqueous phase was extracted with a mixture of dichloromethane and methanol (v/v, 4:1 3×20 mL). The combined organic layer was dried over MgSO$_4$. The product was purified by column chromatography with silica gel (6×6 cm, cyclohexane/ethyl acetate, 8:1) and isolated as a white solid. Yield: 4.598 g (96%). Traces of 1,16-dibromohexadecane were also found.

15

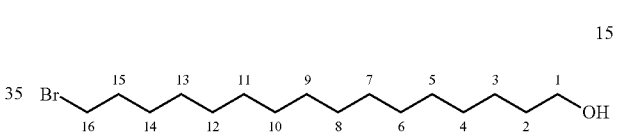

M.p.: 65° C. (lit. 53-54° C.)
$^1$H-NMR (300 MHz, CDCl$_3$) δ [ppm]: 1.26-1.47 (m, 23H, 4-CH$_2$ to 14-CH$_2$, 1-OH), 1.51-1.62 (m, 4H, 2-CH$_2$, 3-CH$_2$), 1.85 (m, 2H, 15-CH$_2$), 3.41 (t, $^3J_{H,H}$=6.9 Hz, 2H, 16-CH$_2$), 3.64 (t, $^3J_{H,H}$=6.6 Hz, 2H, 1-CH$_2$).

$^{13}$C-NMR (75 MHz, CDCl$_3$) δ [ppm]: 25.9 (t, C-3), 28.3, 28.9, 29.6, 29.7, 29.8 (t, C-4 to C-14), 33.0 (t, C-2, C-15), 34.3 (t, C-16), 63.3 (t, C-1).

Refs.: M.p. P. Chuit, J. Hausser, *Helv. Chim. Acta* 1929, 12, 850-859.

$^1$H-NMR spectroscopic data agree with those given by: S. Takanashi, M. Takagi, H. Takikawa; K. Mori, *J. Chem. Soc., Perkin Trans.* 1 1998, 1603-1606.

4.3 Diethyl 2-acetamido-2-(16-hydroxyhexadecyl)malonate

The bromide 15 (0.967 g, 2.70 mmol), diethyl 2-acetamidomalonate 1 (0.640 g, 2.8 mmol, 1.0 eq.) (obtained as in example 1.1 above) and caesium carbonate (1.680 g, 5.17 mmol, 1.9 eq.) were suspended in acetonitrile (20 mL) and refluxed for 5 h. The mixture was adsorbed at silica gel (1-2 g) and purified by column chromatography (silica gel, 16.5×4 cm, cyclohexane/ethyl acetate, 4:1) to give a yellowish solid. Yield: 0.912 g (74%).

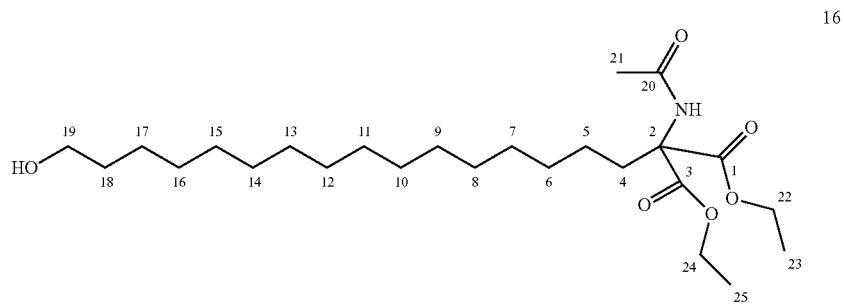 [SMILES: CCOC(=O)C(CCCCCCCCCCCCCCCCO)(NC(C)=O)C(=O)OCC]

16

M.p.: 48° C.

$^1$H-NMR (300 MHz, CDCl$_3$) δ [ppm]: 1.23-1.63 (m, 34H, 5-CH$_2$ to 18-CH$_2$, 23-CH$_3$, 25-CH$_3$), 2.04 (m, 4H, 21-CH$_3$, 19-OH), 2.30 (m, 2H, 4-CH$_2$), 3.63 (t, $^3J_{H,H}$=6.6 Hz, 2H, 19-CH$_2$), 4.20 (m, 4H, 22-CH$_2$, 24-CH$_2$), 6.84 (s, 1H, 2-NH).

$^{13}$C-NMR (75 MHz, CDCl$_3$) δ [ppm]: 14.0 (q, C-23, C-25), 23.1 (q, C-21), 23.6 (t, C-5), 25.8 (t, C-17), 28.4, 29.3, 29.7 (t, C-6 to C-16), 32.1 (t, C-18), 32.8 (t, C-4), 62.5 (t, C-22, C-24), 63.0 (t, C-19), 66.6 (s, C-2), 168.3 (s, C-1, C-3), 169.0 (s, C-20).

Exact mass (ESI$^+$): C$_{25}$H$_{47}$NO$_6$+Na$^+$: calcd. 480.3296. found 480.3300. (C$_{25}$H$_{47}$NO$_6$)$_2$+Na$^+$: calcd. 937.6699. found 937.6713.

4.4 Diethyl 2-amino-2-(16-hydroxyhexadecyl)malonate

Diethyl 2-aminomalonate hydrochloride (0.571 g, 2.64 mmol) and caesiumcarbonate (2.639 g, 8.10 mmol, 3.1 eq.) were suspended in acetonitrile (20 mL) and stirred at r.t. for 15 min. Then the bromide 15 (0.878 g, 2.68 mmol, 98% GC) was added and the mixture was refluxed for 6 h. After cooling to r.t. and partial evaporation of the solvent, the residue was purified by column chromatography (silica gel, 13.5×4 cm, cyclohexane/ethyl acetate, 2:1).

Yield: 0.315 g (29%).

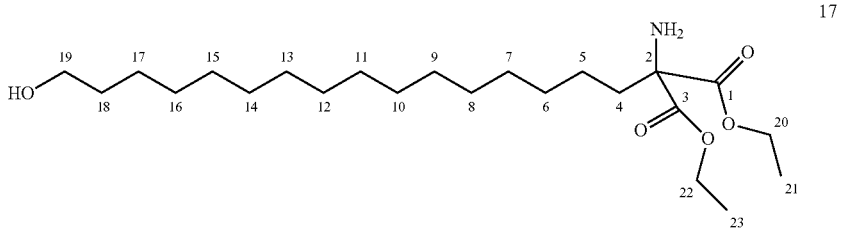 [SMILES: CCOC(=O)C(N)(CCCCCCCCCCCCCCCCO)C(=O)OCC]

17

M.p.: 51-52° C.

$^1$H-NMR (300 MHz, CDCl$_3$, CD$_3$OD) δ [ppm]: 1.26-1.72 (m, 36H, 4-CH$_2$ to 18-CH$_2$, 21-CH$_3$, 23-CH$_3$), 3.57 (t, $^3J_{H,H}$=6.8 Hz, 2H, 19-CH$_2$), 4.24 (d, $^3J_{H,H}$=7.2 Hz, 4H, 20-CH$_2$, 22-CH$_2$).

$^{13}$C-NMR (75 MHz, CDCl$_3$, CD$_3$OD) δ [ppm]: 14.2 (q, C-21, C-23), 23.7 (t, C-5), 26.1 (t, C-17), 29.6, 29.8, 30.0 (t, C-6 to C-16), 32.8 (t, C-18), 35.6 (t, C-4), 62.4 (t, C-20, C-22), 62.6 (t, C-19), 65.9 (s, C-2), 171.7 (s, C-1, C-3).

Exact mass (ESI$^+$): C$_{23}$H$_{45}$NO$_5$+H$^+$: calcd. 416.3371. found 416.3372. C$_{23}$H$_{45}$NO$_5$+Na$^+$: calcd. 438.3190. found 438.3188. (C$_{23}$H$_{45}$NO$_5$)$_2$+Na$^+$: calcd. 853.6488. found 853.6491.

4.5 Diethyl 2-acetamido-2-(16-fluorohexadecyl)malonate

Under argon the alcohol 16 (1.636 g, 3.6 mmol) was dissolved in dichloromethane (25 mL) in a PTFE-vessel and cooled down to −78° C. The reaction mixture was treated carefully with DAST (1.0 mL, 7.2 mmol, 2.0 eq.) and stirred for one more hour at −78° C. Then the mixture was allowed to warm up to r.t. under stirring overnight. The reaction was quenched with sodium bicarbonate solution (50 mL) at −10° C. The phases were separated and the aqueous phase was extracted with dichloromethane (3×30 mL). The combined organic layer was washed with water (30 mL) and dried over MgSO$_4$. The solvent was removed and the product was purified by column chromatography (silica gel, 10.5×4 cm, cyclohexane/ethyl acetate 4:1). Yield: 0.208 g (13%)

4.6 Diethyl 2-amino-2-(16-fluorohexadecyl)malonate

A solution of the alcohol 17 (0.211 g, 0.51 mmol) in dry dichloromethane (10 mL) was cooled down to −78° C. and carefully treated with DAST (0.11 mL, 0.82 mmol, 1.6 eq.). After stirring at this temperature for 1 h the mixture was allowed to warm up to −10° C. and quenched with sodium bicarbonate solution (10 mL). The phases were separated and

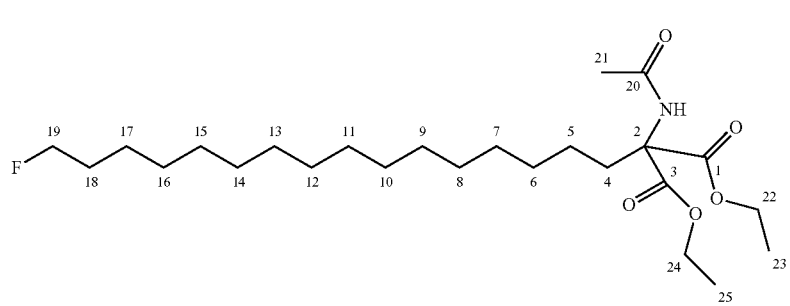

M.p.: 56° C.

$^1$H-NMR (300 MHz, CDCl$_3$) δ [ppm]: 1.20-1.46, 1.60-1.80 (m, 34H, 5-CH$_2$ to 18-CH$_2$, 23-CH$_3$, 25-CH$_3$), 2.04 (s, 3H, 21-CH$_3$), 2.30 (m, 2H, 4-CH$_2$), 4.24 (q, $^3J_{H,H}$=7.1 Hz, 4H, 22-CH$_2$, 24-CH$_2$), 4.44 (dt, $^3J_{H,H}$=6.2 Hz, $^2J_{H,F}$=47.4 Hz, 2H, 19-CH$_2$), 6.80 (s, 1H, 2-NH).

the aqueous phase was extracted with dichloromethane (3×15 mL). The combined organic phases were washed with water and dried over MgSO$_4$. The solvent was evaporated in vacuo and the residue was purified by column chromatography (silica gel, 10×3 cm, cyclohexane/ethyl acetate, 4:1) to give the product as a yellowish oil. Yield: 0.054 g (25%).

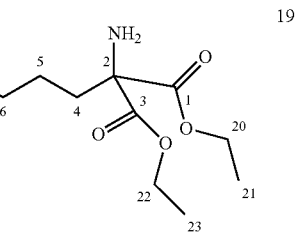

$^{13}$C-NMR (75 MHz, CDCl$_3$) δ [ppm]: 14.1 (q, C-23, C-25), 23.2 (q, C-21), 23.7 (t, C-5), 25.2 (dt, $^3J_{C,F}$=5.5 Hz, C-17), 29.3, 29.5, 29.6, 29.7 (t, C-6 to C-16), 30.5 (dt, $^2J_{C,F}$=19.4 Hz, C-18), 32.2 (t, C-4), 62.5 (t, C-22, C-24), 66.7 (s, C-2), 84.3 (dt, $^1J_{C,F}$=163.9 Hz, C-19), 168.4 (s, C-1, C-3), 169.0 (s, C-20).

$^{19}$F-NMR (282 MHz, CDCl$_3$) δ [ppm]: −218.5 (tt, $^3J_{H,F}$=24.8 Hz, $^2J_{H,F}$=47.3 Hz, 1F, 19-CH$_2$F).

Exact mass (ESI$^+$): C$_{25}$H$_{46}$FNO$_5$+H$^+$: calcd. 460.3433. found 460.3444. C$_{25}$H$_{46}$FNO$_5$+Na$^+$: calcd. 482.3252. found 482.3260. (C$_{25}$H$_{46}$FNO$_5$)$_2$+Na$^+$: calcd. 941.6612. found 941.6634.

$^1$H-NMR (300 MHz, CDCl$_3$) δ [ppm]: 1.21-1.39 (m, 36H, 4-CH$_2$ to 17-CH$_2$, 21-CH$_3$, 23-CH$_3$, 2-NH$_2$), 1.69 (m, 2H, 18-CH$_2$), 4.22 (q, $^3J_{H,H}$=7.1 Hz, 4H, 20-CH$_2$, 22-CH$_2$), 4.44 (dt, $^3J_{H,H}$=6.2 Hz, $^2J_{H,F}$=47.4 Hz, 2H, 19-CH$_2$).

$^{13}$C-NMR (75 MHz, CDCl$_3$) δ [ppm]: 14.2 (q, C-21, C-23), 23.6 (t, C-5), 25.3 (dt, $^3J_{C,F}$=5.6 Hz, C-17), 29.4, 29.5, 29.7, 29.8 (t, C-6 to C-16), 30.6 (dt, $^2J_{C,F}$=19.3 Hz, C-18), 35.5 (t, C-4), 62.0 (t, C-20, C-22), 65.9 (s, C-2), 84.4 (dt, $^1J_{C,F}$=164.0 Hz, C-19), 171.5 (s, C-1, C-3).

$^{19}$F-NMR (282 MHz, CDCl$_3$) δ [ppm]: −218.5 (tt, $^3J_{H,F}$=24.8 Hz, $^2J_{H,F}$=47.3 Hz, 1F, 19-CH$_2$F).

Exact mass (ESI$^+$): C$_{23}$H$_{45}$FNO$_4$+H$^+$: calcd. 418.3327. found 418.3317.

4.7 N-[17-Fluoro-1,1-bis(hydroxymethyl)heptadecyl]acetamide

The diester 18 (0.098 g, 0.21 mmol) was dissolved in THF (5 mL) and reacted with lithium chloride (0.047 g, 1.1 mmol, 5.0 eq.) and sodium borohydride (0.042 g, 1.1 mmol, 5.0 eq.). The mixture was cooled to 0° C. and treated with ethanol (10 mL). After stirring for one more hour at 0° C. the mixture was stirred at r.t. overnight. After cooling to 0° C. 10% citric acid was added to adjust pH 4. THF was removed and the residue was dissolved in water (10 mL). The aqueous phase was extracted with dichloromethane (4×10 mL). The organic layer was washed with water and dried over $Na_2SO_4$. The solvent was removed and the residue was purified by column chromatography (silica gel, 16×3 cm, cyclohexane/ethyl acetate, 1:2). The product was isolated as a white solid. Yield: 0.017 g (24%).

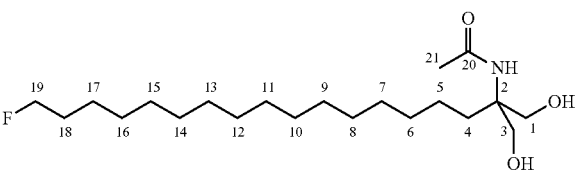

M.p.: 93° C.

$^1$H-NMR (300 MHz, $CDCl_3$, $CD_3OD$) δ [ppm]: 1.19-1.33 (m, 26H, 5-$CH_2$ to 17-$CH_2$), 1.55-1.75 (m, 4H, 4-$CH_2$, 18-$CH_2$), 2.03 (m, 3H, 21-$CH_3$), 3.67 (m, 4H, 1-$CH_2$, 3-$CH_2$), 4.44 (dt, $^3J_{H,H}$=6.2 Hz, $^2J_{H,F}$=47.5 Hz, 2H, 19-$CH_2$).

$^{13}$C-NMR (101 MHz, $CDCl_3$) δ [ppm]: 23.1 (q, C-21), 23.4 (t, C-5), 25.1 (dt, $^3J_{C,F}$=5.5 Hz, C-17), 29.2, 29.5, 29.6, 30.1 (t, C-6 to C-16), 30.4 (dt, $^2J_{C,F}$=18.9 Hz, C-18), 32.4 (t, C-4), 61.3 (s, C-2), 65.1 (t, C-1, C-3), 84.3 (dt, $^1J_{C,F}$=163.5 Hz, C-19), 171.8 (s, C-20).

$^{19}$F-NMR (282 MHz, $CDCl_3$, $CD_3OD$) δ [ppm]: −218.4 (tt, $^3J_{H,F}$=24.9 Hz, $^2J_{H,F}$=47.3 Hz, 1F, 19-$CH_2F$).

Exact mass (ESI$^+$): $C_{21}H_{42}FNO_3$+H$^+$: calcd. 376.3221. found 376.3214. $C_{21}H_{42}FNO_3$+Na$^+$: calcd. 398.3041. found 398.3040.

4.8 2-Amino-2-(16-fluorohexadecyl)propan-1,3-diol (SSS 558)

The diester 19 (0.054 g, 0.13 mmol) was dissolved in THF (5 mL) and reacted with lithium chloride (0.027 g, 0.65 mmol, 5.0 eq.) and sodium borohydride (0.024 g, 0.65 mmol, 5.0 eq.). The mixture was cooled to 0° C. and treated with ethanol (10 mL). After stirring for one more hour at 0° C. the mixture was stirred at r.t. overnight. After cooling to 0° C. 10% citric acid was added to adjust pH 4. THF was removed and the residue was dissolved in water (10 mL). The aqueous phase was extracted with dichloromethane (4×10 mL). The organic layer was washed with water and dried over $Na_2SO_4$. The solvent was removed and the residue was purified by column chromatography (silica gel, 16×3 cm, cyclohexane/ethyl acetate, 1:2). The product was recrystallized from ethyl acetate and isolated as a white solid. Yield: 0.017 g (39%).

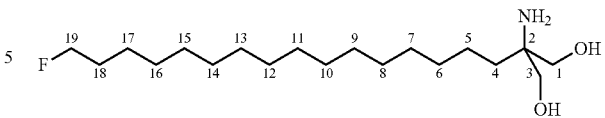

M.p.: 77° C.

$^1$H-NMR (600 MHz, $CD_3OD$) δ [ppm]: 1.29-1.41 (m, 28H, 4-$CH_2$ to 17-$CH_2$), 1.66 (m, 2H, 18-$CH_2$), 3.39 (d, $^2J_{H,H}$=10.8 Hz, 2H, 1-$CH_2$, 3-$CH_2$), 3.45 (d, $^2J_{H,H}$=10.9 Hz, 2H, 1-$CH_2$, 3-$CH_2$), 4.40 (dt, $^3J_{H,H}$=6.1 Hz, $^2J_{H,F}$=47.6 Hz, 2H, 19-$CH_2$).

$^{13}$C-NMR (151 MHz, $CD_3OD$) δ [ppm]: 23.9 (t, C-5), 26.3 (dt, $^3J_{C,F}$=5.2 Hz, C-17), 30.4, 30.7, 30.8 (t, C-7 to C-16), 31.6 (dt, $^2J_{C,F}$=19.6 Hz, C-18), 31.6 (t, C-6), 35.1 (t, C-4), 56.9 (s, C-2), 66.4 (t, C-1, C-3), 84.9 (dt, $^1J_{C,F}$=163.7 Hz, C-19).

$^{19}$F-NMR (282 MHz, $CD_3OD$) δ [ppm]: −218.2 (m, 1F).

Exact mass (ESI$^+$): $C_{19}H_{40}FNO_2$+H$^+$: calcd. 334.3116. found 334.3123. $C_{19}H_{40}FNO_2$+Na$^+$: calcd. 356.2935. found 356.2945.

Alternatively the diol 20 (0.017 mg, 0.05 mmol) was dissolved in methanol (2 mL) and treated with 1 M NaOH (88 μL, 0.09 mmol, 1.8 eq.). With stirring the reaction mixture was heated at 120° C. in a pressure vessel for 6.5 h and was allowed to cool down to r.t. while stirring overnight. After dilution with water (5 mL) the aqueous phase was extracted with dichloromethane (4×10 mL). The combined organic layer was dried over $Na_2SO_4$ and the solvent was evaporated in vacuo. The product was crystallized from ethyl acetate and isolated as a white solid. Yield: 0.015 g (90%).

4.9 Pentadecane-1,15-diol

Lithium aluminium hydride (1.52 g, 40.0 mmol, 2.0 eq.) was suspended in dry THF (80 mL) under an argon atmosphere. A solution of 15-pentadecanolide (4.80 g, 20.0 mmol) in dry THF (200 mL) was added at 0° C. Stirring was continued at this temperature for 1 h and for 3 more hours at r.t. Potassium sodium tartrate solution (20%, 50 mL) was added dropwise to the stirred reaction mixture. The phases were separated and the aqueous phase was extracted with diethyl ether (3×100 ml). The combined organic layers were dried over $MgSO_4$. The solvent was removed in vacuo and the product was isolated as a white solid, which was used for the next step without purification. Yield: 4.68 g (96%).

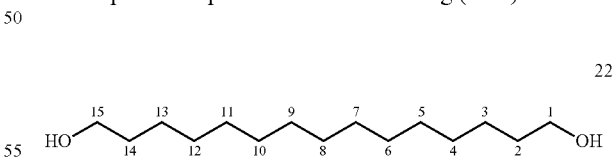

M.p.: 86-87° C. (lit. 87° C.)

$^1$H-NMR (300 MHz, $CDCl_3$) δ [ppm]: 1.28-1.33 (m, 24H, 3-$CH_2$ to 13-$CH_2$, 1-OH, 15-OH), 1.53 (m, 4H, 2-$CH_2$, 14-$CH_2$), 3.55 (t, $^3J_{H,H}$=6.8 Hz, 4H, 1-$CH_2$, 15-$CH_2$).

$^{13}$C-NMR (75 MHz, $CDCl_3$) δ [ppm]: 26.4 (t, C-3, C-13), 30.1, 30.3 (t, C-4 to C-12), 33.1 (t, C-2, C-14), 62.7 (t, C-1, C-15).

Refs.: Synthesis according to C. Girlanda-Junges, F. Keyling-Bilger, G. Schmitt, B. Luu, *Tetrahedron* 1998, 54, 7735-7748.

M.p. P. Chuit, J. Hausser, *Helv. Chim. Acta* 1929, 12, 850-859.

4.10 15-Bromopentadecane-1-ol

Diol 22 (4.70 g, 19.2 mmol) was dissolved in cyclohexane (50 mL) and 48% HBr (2.4 mL, 21.2 mmol, 1.1 eq.) was added under vigorous stirring. The mixture was refluxed overnight. After cooling to r.t., saturated sodium bicarbonate solution (100 mL) was added and the phases were separated. The aqueous phase was extracted with dichloromethane (3×50 mL). The combined organic layers were dried over MgSO$_4$. After evaporation of the solvent the product was purified by column chromatography (silica gel, 27×4 cm, cyclohexane/ethyl acetate, 4:1→100% ethyl acetate) and isolated as a white solid. Yield: 3.39 g (58%). Traces of 1,15-dibromopentadecane were also found.

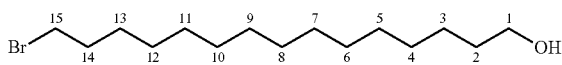

M.p.: 63-65° C.
$^1$H-NMR (300 MHz, CDCl$_3$) δ [ppm]: 1.26-1.44 (m, 23H, 3-CH$_2$ to 13-CH$_2$, 1-OH), 1.55 (m, 2H, 2-CH$_2$), 1.85 (m, 2H, 14-CH$_2$), 3.41 (t, $^3J_{H,H}$=6.9 Hz, 2H, 15-CH$_2$), 3.63 (t, $^3J_{H,H}$=6.6 Hz, 2H, 1-CH$_2$).
$^{13}$C-NMR (75 MHz, CDCl$_3$) δ [ppm]: 25.9 (t, C-3), 28.3, 28.9, 29.6, 29.7, 29.8 (t, C-4 to C-13), 32.9 (t, C-14), 33.0 (t, C-2), 34.2 (t, C-15), 63.1 (t, C-1).
Ref.: Synthesis according to C. Girlanda-Junges, F. Keyling-Bilger, G. Schmitt, B. Luu, *Tetrahedron* 1998, 54, 7735-7748.

4.11 Diethyl 2-acetamido-2-(15-hydroxypentadecyl)malonate

Bromide 23 (966 mg, 3.1 mmol), diethyl 2-acetamidomalonate 1 (673 mg, 3.1 mmol, 1.0 eq.) (obtained as in example 1.1 above) and caesium carbonate (1.06 g, 3.3 mmol, 1.1 eq.) were suspended in acetonitrile (20 mL) and the mixture was refluxed for 6 h. After cooling to r.t., the mixture was adsorbed on silica gel (1-2 g) and purified by column chromatography (silica gel, 8×4 cm, cyclohexane/ethyl acetate, 4:1→100% ethyl acetate). The product was obtained as a white solid. Yield: 1.11 g (80%).

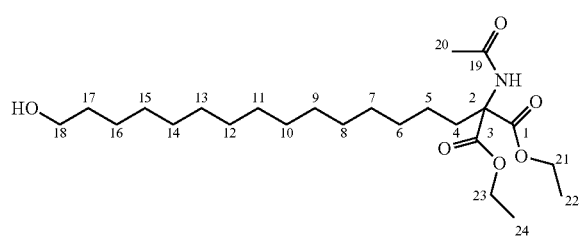

M.p.: 52° C.
$^1$H-NMR (300 MHz, CDCl$_3$) δ [ppm]: 1.19-1.37 (m, 30H, 5-CH$_2$ to 16-CH$_2$, 22-CH$_3$, 24-CH$_3$), 1.56 (m, 2H, 17-CH$_2$), 2.03 (s, 3H, 20-CH$_3$), 2.30 (m, 2H, 4-CH$_2$), 3.63 (t, $^3J_{H,H}$=6.6 Hz, 2H, 18-CH$_2$), 4.24 (q, $^3J_{H,H}$=7.2 Hz, 4H, 21-CH$_2$, 23-CH$_2$), 6.81 (s, 1H, 2-NH).
$^{13}$C-NMR (75 MHz, CDCl$_3$) δ [ppm]: 14.1 (q, C-22, C-24), 23.1 (q, C-20), 23.7 (t, C-5), 25.8 (t, C-16), 29.3, 29.4, 29.5, 29.7 (t, C-6 to C-15), 32.2 (t, C-17), 32.9 (t, C-4), 62.5 (t, C-21, C-23), 63.0 (t, C-18), 66.7 (s, C-2), 168.3 (s, C-1, C-3), 169.0 (s, C-19).
Exact mass (ESI$^+$): C$_{24}$H$_{45}$NO$_6$+Na$^+$: calcd. 466.3139. found 466.3138. (C$_{24}$H$_{45}$NO$_6$)$_2$+Na$^+$: calcd. 909.6386. found 909.6394.

4.12 Diethyl 2-acetamido-2-(15-fluoropentadecyl)malonate

Under argon the alcohol 24 (443 mg, 1.0 mmol) was dissolved in dry dichloromethane (8 mL), cooled down to −78° C. and carefully treated with DAST (0.18 mL, 1.3 mmol, 1.3 eq.). After stirring at −78° C. for 1 h, the mixture was allowed to warm up to r.t. overnight. The reaction was quenched with saturated sodium bicarbonate solution (20 mL) at −10° C. The phases were separated and the aqueous phase was extracted with dichloromethane (4×10 mL). The combined organic layers were dried over Na$_2$SO$_4$ and the solvent was removed in vacuo. The product was purified by silica gel column chromatography (11.5×3 cm, cyclohexane/ethyl acetate, 4:1) and was obtained as white and waxy solid.
Yield: 179 mg (40%).

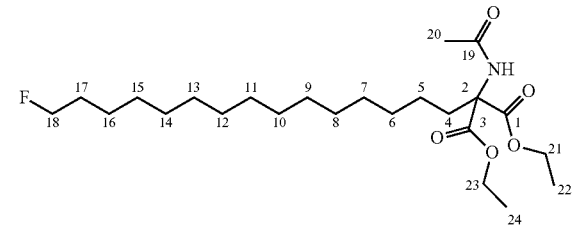

M.p.: 57° C.
$^1$H-NMR (300 MHz, CDCl$_3$) δ [ppm]: 1.18-1.44 (m, 30H, 5-CH$_2$ to 16-CH$_2$, 22-CH$_3$, 24-CH$_3$), 1.68 (m, 2H, 17-CH$_2$), 2.04 (s, 3H, 20-CH$_3$), 2.31 (m, 2H, 4-CH$_2$), 4.24 (q, $^3J_{H,H}$=7.1 Hz, 4H, 21-CH$_2$, 23-CH$_2$), 4.43 (dt, $^3J_{H,H}$=6.2 Hz, $^2J_{H,F}$=47.4 Hz, 2H, 18-CH$_2$), 6.83 (s, 1H, 2-NH).
$^{13}$C-NMR (75 MHz, CDCl$_3$) δ [ppm]: 14.0 (q, C-22, C-24), 23.0 (q, C-20), 23.6 (t, C-5), 25.2 (dt, $^3J_{C,F}$=5.5 Hz, C-16), 29.3, 29.4, 29.6, 29.7 (t, C-6 to C-15), 30.4 (dt, $^2J_{C,F}$=19.3 Hz, C-17), 32.1 (t, C-4), 62.4 (t, C-21, C-23), 66.6 (s, C-2), 84.2 (dt, $^1J_{C,F}$=163.9 Hz, C-18), 168.3 (s, C-1, C-3), 168.9 (s, C-19).
$^{19}$F-NMR (282 MHz, CDCl$_3$) δ [ppm]: −218.4 (tt, $^3J_{H,F}$=24.8 Hz, $^2J_{H,F}$=47.4 Hz, 1F, 18-CH$_2$F).
Exact mass (ESI$^+$): C$_{24}$H$_{44}$FNO$_5$+H$^+$: calcd. 446.3276. found 446.3274; C$_{24}$H$_{44}$FNO$_5$+Na$^+$: calcd. 468.3096. found 468.3093. (C$_{24}$H$_{44}$FNO$_5$)$_2$+Na$^+$: calcd. 913.6299. found 913.6286.

4.13 N-[16-Fluoro-1,1-bis(hydroxymethyl)hexadecyl]acetamide

Diester 25 (170 mg, 0.38 mmol) was dissolved in THF (6 mL). Lithium chloride (81 mg, 1.90 mmol, 5.0 eq.) and sodium borohydride (72 mg, 1.90 mmol, 5.0 eq.) were added.

The mixture was cooled to 0° C. and treated with ethanol (12 mL). After stirring for 35 min at 0° C., the mixture was allowed to warm up to r.t. and was stirred overnight. After cooling to 0° C. potassium sodium tartrate solution (20%, 5 mL) was added and THF was removed in vacuo. The residue was diluted with water (5 mL) and extracted with dichloromethane (4×15 mL). The organic layer was dried over $Na_2SO_4$ and the solvent was removed. The product was purified by column chromatography (silica gel, 9.5×3 cm, cyclohexane/ethyl acetate, 1:2) and was obtained as a white solid. Yield: 31 mg (23%)

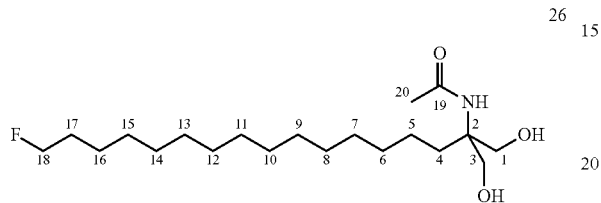

26

M.p.: 101° C.
$^1$H-NMR (300 MHz, $CDCl_3$, $CD_3OD$) δ [ppm]: 1.20-1.44 (m, 24H, 5-$CH_2$ to 16-$CH_2$), 1.59-1.78 (m, 4H, 4-$CH_2$, 17-$CH_2$), 2.01 (s, 3H, 20-$CH_3$), 3.62 (d, $^2J_{H,H}$=11.4 Hz, 2H, 1-$CH_2$, 3-$CH_2$), 3.69 (d, $^2J_{H,H}$=11.6 Hz, 2H, 1-$CH_2$, 3-$CH_2$), 4.43 (dt, $^3J_{H,H}$=6.2 Hz, $^2J_{H,F}$=47.4 Hz, 2H, 18-$CH_2$).
$^{13}$C-NMR (101 MHz, $CDCl_3$, $CD_3OD$) δ [ppm]: 23.5 (s, C-20), 23.6 (t, C-5), 25.7 (dt, $^3J_{C,F}$=5.3 Hz, C-16), 29.8, 30.1, 30.2, 30.7 (t, C-6 to C-15), 31.0 (dt, $^2J_{C,F}$=19.2 Hz, C-17), 32.5 (t, C-4), 62.1 (s, C-2), 64.9 (t, C-1, C-3), 84.6 (dt, $^1J_{C,F}$=163.6 Hz, C-18), 173.4 (s, C-19).
$^{19}$F-NMR (282 MHz, $CDCl_3$, $CD_3OD$) δ [ppm]: -218.3 (tt, $^3J_{H,F}$=23.8 Hz, $^2J_{H,F}$=47.5 Hz, 1F, 18-$CH_2F$).
Exact mass (ESI$^+$): $C_{20}H_{40}FNO_3$+H$^+$: calcd. 362.3065. found 362.3068. $C_{20}H_{40}FNO_3$+Na$^+$: calcd. 384.2884. found 384.2886.

4.14
2-Amino-2-(15-fluoropentadecyl)propane-1,3-diol (SSS 890)

Diol 26 (28 mg, 77 μmol) was dissolved in methanol (3 mL) and treated with 1 M NaOH (0.12 mL, 0.12 mmol, 1.6 eq.). The reaction mixture was heated to 120° C. for 6 h in a pressure vessel. After cooling to r.t. the mixture was diluted with 1 M NaOH (3 mL) and extracted with dichloromethane (5×10 mL). The combined organic layers were dried over $Na_2SO_4$ and the solvent was evaporated. The product was crystallized from ethyl acetate and was isolated as a white solid. Yield: 23 mg (90%).

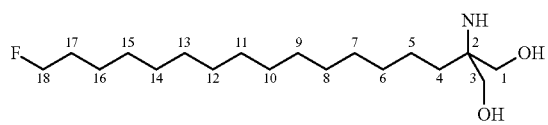

27

M.p.: 85° C.
$^1$H-NMR (300 MHz, $CD_3OD$, $CDCl_3$) δ [ppm]: 1.24-1.43 (m, 26H, 4-$CH_2$ to 16-$CH_2$), 1.67 (m, 2H, 17-$CH_2$), 3.41 (d, $^2J_{H,H}$=11.0 Hz, 2H, 1-$CH_2$, 3-$CH_2$), 3.49 (d, $^2J_{H,H}$=11.0 Hz, 2H, 1-$CH_2$, 3-$CH_2$), 4.43 (dt, $^3J_{H,H}$=6.1 Hz, $^2J_{H,F}$=47.5 Hz, 2H, 18-$CH_2$).
$^{13}$C-NMR (75 MHz, $CD_3OD$, $CDCl_3$) δ [ppm]: 23.5 (t, C-5), 25.7 (dt, $^3J_{C,F}$=5.4 Hz, C-16), 29.8, 30.1, 30.2 (t, C-7 to C-15), 31.0 (dt, $^2J_{C,F}$=19.4 Hz, C-17), 31.0 (t, C-6), 34.8 (t, C-4), 56.3 (s, C-2), 66.3 (t, C-1, C-3), 84.6 (dt, $^1J_{C,F}$=163.7 Hz, C-18).
$^{19}$F-NMR (282 MHz, $CD_3OD$, $CDCl_3$) δ [ppm]: -218.3 (tt, $^3J_{H,F}$=24.9 Hz, $^2J_{H,F}$=47.5 Hz, 1F, 18-$CH_2F$).
Exact mass (ESI$^+$): $C_{18}H_{38}FNO_2$+H$^+$: calcd. 320.2959. found 320.2961.

5. Synthesis of the Dansyl-Labelled Compound

5.1 1,16-Diiodohexadecane

Sodium iodide (12.04 g, 80.3 mmol, 4.0 eq.) was added in portions to phosphoric acid (27 mL, 85%) at 0° C. The diol 14 (5.190 g, 20.1 mmol) (obtained following the procedure of example 4.1 above) was added at r.t. and the mixture was heated at 120° C. for 3 h. After cooling to r.t. the mixture was poured into water (150 mL) and extracted with diethyl ether (3×50 mL). The combined organic layer was washed with sodium thiosulfate solution (2×25 mL), sodium bicarbonate solution (25 mL) and water (25 mL). The ethereal layer was dried over $Na_2SO_4$ and the solvent was evaporated. The product was purified by column filtration (silica gel, 9×5 cm, cyclohexane) to be isolated as a white solid. Yield: 8.860 g (92%), purity: 91% (GC).

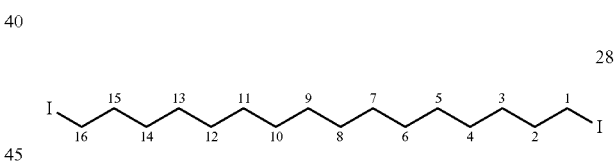

28

M.p.: 56° C. (lit. 55.5-56.5° C.)
$^1$H-NMR (300 MHz, $CDCl_3$) δ [ppm]: 1.23-1.42 (m, 24H, 3-$CH_2$ bis 14-$CH_2$), 1.82 (m, 4H, 2-$CH_2$, 15-$CH_2$), 3.19 (t, $^3J_{H,H}$=7.0 Hz, 4H, 1-$CH_2$, 16-$CH_2$).
$^{13}$C-NMR (75 MHz, $CDCl_3$) δ [ppm]: 7.5 (t, C-1, C-16), 28.7 (t, C-3, C-14), 29.6, 29.7, 29.8, 30.7 (t, C-4 bis C-13), 33.7 (t, C-2, C-15).
Ref.: M.p. and synthesis according to W. E. Schultz, H.-J. Machulla, L. E. Feinendegen, J. Radioanal. *Nucl. Chem. Letters* 1989, 135, 199-205.

5.2 Diethyl 2-amino-2-(16-iodohexadecyl)malonate

Diethyl 2-aminomalonate hydrochloride (2.116 g, 10.0 mmol) and caesiumcarbonate (7.100 g, 21.8 mmol, 2.2 eq.) were suspended in acetonitrile (50 mL) and stirred at r.t. for 15 min. Then diiodohexadecane 28 (5.017 g, 10.5 mmol, 1.1 eq.) was added and the mixture was refluxed for 6 h. After cooling to r.t. and partial evaporation of the solvent, the residue was purified by column chromatography (silica gel, 16×4 cm, cyclohexane/ethyl acetate, 2:1) to give the product as a yellowish oil. Yield: 3.097 g (56%).

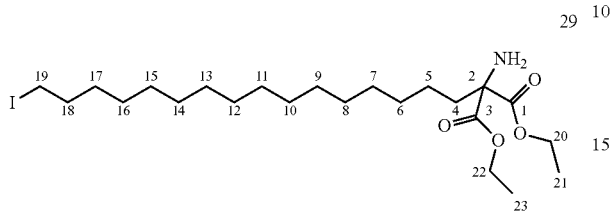

$^1$H-NMR (300 MHz, CDCl$_3$) δ [ppm]: 1.23-1.44 (m, 32H, 5-CH$_2$ to 17-CH$_2$, 21-CH$_3$, 23-CH$_3$), 1.82 (m, 2H, 18-CH$_2$), 1.97 (m, 2H, 4-CH$_2$), 3.19 (t, $^3J_{H,H}$=7.0 Hz, 2H, 19-CH$_2$), 4.22 (m, 4H, 20-CH$_2$, 22-CH$_2$).

$^{13}$C-NMR (75 MHz, CDCl$_3$) δ [ppm]: 7.4 (t, C-19), 14.2 (q, C-21, C-23), 23.6 (t, C-5), 28.6 (t, C-17), 29.5, 29.7 (t, C-7 to C-16), 30.6 (t, C-6), 33.7 (t, C-18), 35.6 (t, C-4), 61.9 (t, C-20, C-22), 65.8 (s, C-2), 171.7 (s, C-1, C-3).

Exact mass (ESI$^+$): C$_{23}$H$_{44}$INO$_4$+H$^+$: calcd. 526.2388. found 526.2389. C$_{23}$H$_{44}$INO$_4$+Na$^+$: calcd. 548.2207. found 548.2216.

5.3 Diethyl 2-amino-2-(16-azidohexadecyl)malonate

The iodide 29 (0.680 g, 1.29 mmol) in DMF (5 mL) was stirred with sodium azide (0.185 g, 2.84 mmol, 2.2 eq.) at r.t. overnight. Then water (10 mL) was added and the solution was extracted with ethyl acetate (3×10 mL). The combined organic layer was washed with water (10 mL) and dried over Na$_2$SO$_4$. After evaporation of the solvent, the crude product was purified by column chromatography (silica gel, 10.5×4 cm, cyclohexane/ethyl acetate, 2:1) to give a yellowish oil. Yield: 0.516 g (91%).

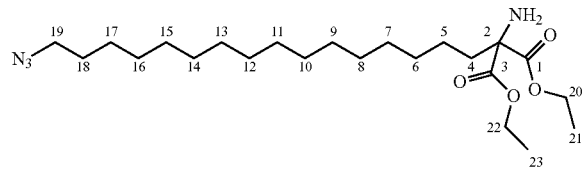

$^1$H-NMR (400 MHz, CDCl$_3$) δ [ppm]: 1.19-1.42 (m, 32H, 5-CH$_2$ to 17-CH$_2$, 21-CH$_3$, 23-CH$_3$), 1.59 (m, 2H, 18-CH$_2$), 1.95 (m, 2H, 4-CH$_2$), 3.25 (t, $^3J_{H,H}$=7.0 Hz, 2H, 19-CH$_2$), 4.22 (q, $^3J_{H,H}$=7.2 Hz, 4H, 20-CH$_2$, 22-CH$_2$).

$^{13}$C-NMR (101 MHz, CDCl$_3$) δ [ppm]: 14.1 (q, C-21, C-23), 23.6 (t, C-5), 26.8 (t, C-17), 28.9, 29.3, 29.6, 29.8 (t, C-6 to C-16), 32.9 (t, C-18), 35.6 (t, C-4), 51.6 (t, C-19), 61.9 (t, C-20, C-22), 65.9 (s, C-2), 171.5 (s, C-1, C-3).

Exact mass (ESI$^+$): C$_{23}$H$_{44}$N$_4$O$_4$+H$^+$: calcd. 441.3435. found 441.3437. C$_{23}$H$_{44}$N$_4$O$_3$+Na$^+$: calcd. 463.3255. found 463.3252.

5.4 2-Amino-2-(16-azidohexadecyl)propane-1,3-diol

The diester 30 (0.252 g, 0.57 mmol) was dissolved in THF (5 mL) and reacted with lithium chloride (0.097 g, 2.28 mmol, 4.0 eq.) and sodiumborohydride (0.086 g, 2.28 mmol, 4.0 eq.). The mixture was cooled to 0° C. and treated with ethanol (10 mL). After stirring for one more hour at 0° C. the mixture was stirred at r.t. for two days. Potassium sodium tartrate solution (5 mL) was troped to the reaction mixture and the aqueous phase was extracted with dichloromethane (4×10 mL). The combined organic layer was dried over Na$_2$SO$_4$. The solvent was removed and the residue was purified by column chromatography (silica gel, 9.5×2 cm, dichloromethane/methanol, 4:1). The product was isolated as a white solid. Yield: 0.063 g (32%).

M.p.: 53° C.

$^1$H-NMR (400 MHz, CD$_3$OD) δ [ppm]: 1.30 (m, 28H, 4-CH$_2$ to 17-CH$_2$), 1.58 (m, 2H, 18-CH$_2$), 3.27 (t, $^3J_{H,H}$=6.8 Hz, 2H, 19-CH$_2$), 3.38 (d, $^2J_{H,H}$=10.8 Hz, 2H, 1-CH$_2$, 3-CH$_2$), 3.44 (d, $^2J_{H,H}$=10.8 Hz, 2H, 1-CH$_2$, 3-CH$_2$).

$^{13}$C-NMR (101 MHz, CD$_3$OD) δ [ppm]: 23.9 (t, C-5), 27.8 (t, C-17), 29.9, 30.3, 30.7, 30.8 (t, C-6 to C-16), 31.6 (t, C-18), 35.2 (t, C-4), 52.5 (t, C-19), 56.9 (s, C-2), 66.4 (t, C-1, C-3).

Exact mass (ESI$^+$): C$_{19}$H$_{40}$N$_4$O$_2$+H$^+$: calcd. 357.3224. found 357.3226. C$_{19}$H$_{40}$N$_4$O$_2$+Na$^+$: calcd. 379.3043. found 379.3048.

5.5 N-(17-Amino-18-hydroxy-17-(hydroxymethyl) octadecyl)-5-(dimethylamino)naphthalene-1-sulfonamide (SSS 846)

In a 10 mL glass vial capped with a septum, the azide 31 (0.061 g, 0.17 mmol) and triphenylphosphine (0.051 g, 0.19 mmol, 1.1 eq.) were dissolved in a THF/water mixture (9:1, 2 mL). The mixture was heated at 80° C. in a microwave oven (150 W) for 30 min. Then dansylchloride (0.046 g, 0.17 mmol, 1.0 eq.) and triethylamine (23.8 µL, 0.17 mmol, 1.0 eq.) were added and the reaction mixture was heated again at 80° C. for 30 min. Subsequently the mixture was diluted with dichloromethane (30 mL) and dried over Na$_2$SO$_4$. The solvent was removed in vacuo and the crude product was purified by column chromatography (silica gel 13.5×2 cm, dichloromethane/methanol, 10:1). The pure product was isolated as a greenish fluorescent, waxy solid. Yield: 0.054 g (56%).

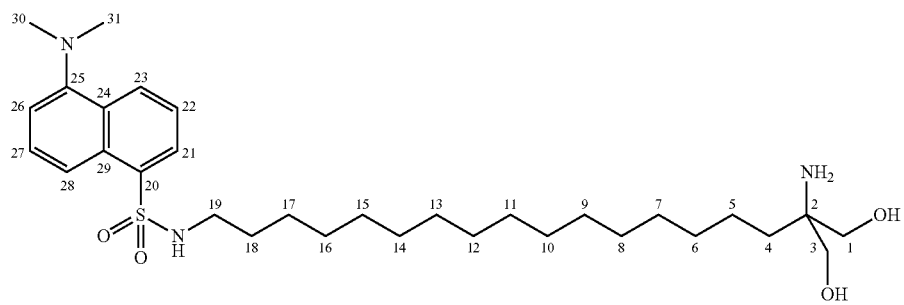

32

M.p.: 72-75° C.

$^1$H-NMR (400 MHz, CD$_2$Cl$_2$) δ [ppm]: 1.01-1.40 (m, 32H, 4-CH$_2$ to 17-CH$_2$, 1-OH, 3-OH, 2-NH$_2$), 1.66 (m, 2H, 18-CH$_2$), 2.86 (s, 6H, 30-CH$_3$, 31-CH$_3$), 3.06 (m, 2H, 19-CH$_2$), 3.73 (d, $^2J_{H,H}$=12.1 Hz, 2H, 1-CH$_2$, 3-CH$_2$), 3.79 (d, $^2J_{H,H}$=11.9 Hz, 2H, 1-CH$_2$, 3-CH$_2$), 5.12 (br s, 1H, 19-NH), 7.18 (d, $^3J_{H,H}$=7.5 Hz, 1H, 26-CH), 7.53 (m, 2H, 22-CH, 27-CH), 8.19 (dd, $^4J_{H,H}$=1.3 Hz, $^3J_{H,H}$=7.3 Hz, 1H, 21-CH), 8.26 (d, $^3J_{H,H}$=8.6 Hz, 1H, 28-CH), 8.53 (m, 1H, 23-CH).

$^{13}$C-NMR (75 MHz, CD$_2$Cl$_2$, CD$_3$OD) δ [ppm]: 23.3 (t, C-5), 27.0 (t, C-17), 29.5, 29.9, 30.0, 30.1, 30.2, 30.6 (t, C-7 to C-16), 31.1 (t, C-6), 32.1 (t, C-18), 43.7 (t, C-4), 45.7 (q, C-30, C-31), 46.7 (t, C-19), 61.7 (s, C-2), 62.6 (t, C-1, C-3), 115.7 (d, C-26), 119.3 (d, C-28), 123.7 (d, C-22), 128.7 (s, C-24), 129.9 (s, C-29), 130.2 (d, C-27), 130.4 (d, C-21), 130.8 (d, C-23), 135.6 (s, C-20), 152.6 (s, C-25).

Exact mass (ESI$^+$): C$_{31}$H$_{53}$N$_3$O$_4$S+H$^+$: calcd. 564.3830. found 564.3835. C$_{31}$H$_{53}$N$_3$O$_4$S+Na$^+$: calcd. 586.3649. found: 586.3654.

6. Synthesis of a Cyanine Dye-Labelled Compound

6.1 2-Amino-2-(16-aminohexadecyl)propane-1,3-diol

Ultrapure hydrogen gas was generated with a Nitrox UHP-40H hydrogen generator (DOMNICK HUNTER, England).

Azide 31 (33 mg, 0.09 mmol) obtained as in example 5.4 above was dissolved in methanol p.a. (3 mL) and the catalyst (10% palladium on activated carbon, 15 mg) was added. The flask was flushed with hydrogen and the mixture was stirred at r.t. overnight under a hydrogen pressure of 2 bar. The reaction was stopped by releasing the hydrogen gas and the catalyst was removed by filtration over a pad of glass wool which was washed with methanol (5 mL) afterwards. The solvent was removed under reduced pressure and the product was obtained as a white and waxy solid, which was used in the labelling experiment without purification. Yield: 25 mg (61%), purity: 75% (NMR).

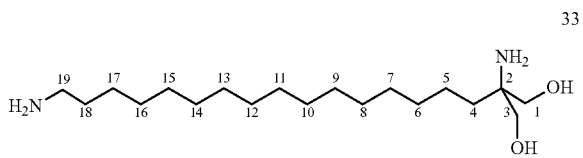 [SMILES: NCCCCCCCCCCCCCCCCC(N)(CO)CO]

33

M.p.: 89-91° C.

$^1$H-NMR (300 MHz, CD$_3$OD, CDCl$_3$) δ [ppm]: 1.23-1.41 (m, 26H, 5-CH$_2$ to 17-CH$_2$), 1.44-1.56 (m, 4H, 4-CH$_2$, 18-CH$_2$), 2.67 (m, 2H, 19-CH$_2$), 3.40 (d, $^2J_{H,H}$=10.9 Hz, 2H, 1-CH$_2$, 3-CH$_2$), 3.47 (d, $^2J_{H,H}$=10.9 Hz, 2H, 1-CH$_2$, 3-CH$_2$).

$^{13}$C-NMR (75 MHz, CD$_3$OD, CDCl$_3$) δ [ppm]: 23.7 (t, C-5), 27.6 (t, C-17), 30.2, 30.4 (t, C-7 to C-17), 31.2 (t, C-6), 33.0, 35.0 (t, C-4, C-18), 42.1 (t, C-19), 56.3 (s, C-2), 66.4 (t, C-1, C-3).

Exact mass (ESI$^+$): C$_{19}$H$_{42}$N$_2$O$_2$+2H$^+$: calcd. 166.1696. found 166.1703. C$_{19}$H$_{42}$N$_2$O$_2$+H$^+$: calcd. 331.3319. found 331.3319.

6.2 Fluorochrome Conjugation—Cy001-Labelled Aminodiol 34 (SSS 996)

Diamine 33 (3 mg, 6.8 μmol, 1.9 eq.) was suspended in 0.1 M triethyl amine in DMF (500 μL) and Cy001 NHS ester (4 mg, 3.6 μmol) was added. The reaction mixture was stirred in an incubator at 40° C. for 2 days in the dark. Cy001-labelled aminodiol 34 was purified by gradient HPLC using a Knauer system (RP-HPLC Nucleosil 100-5 C$_{18}$ column (250×10 mm), water/acetonitrile (0.1% TFA)). The appropriate fraction was collected, lyophilized, re-dissolved in 0.9% NaCl-solution and finally stored at −20° C. The average content of 34 was 85.08 nmol/mL (≈2%) as determined by fluorometer measurements with $\lambda_{abs}$=638 nm and $\epsilon_{638}$=220 000 M$^{-1}$ cm$^{-1}$. Further analyses by HPLC-MS measurements revealed that both regioisomers were obtained in a ratio of 1:4. An explicit assignment of the main product is not possible from the obtained data.

35
Exact mass (ESI⁺): [C₆₁H₈₉N₅O₁₅S₄+H+3Na]²⁺ calcd. 664.74992. found 664.75019.
36
Exact mass (ESI⁻): [C₆₁H₈₉N₅O₁₅S₄]²⁻ calcd. 629.76245. found 629.76496.
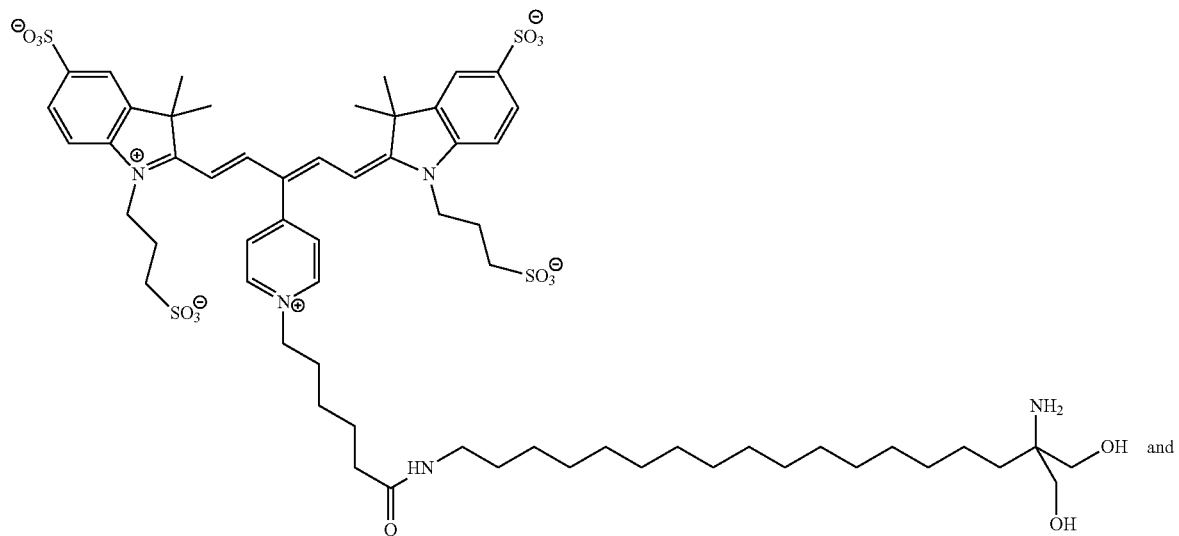
34
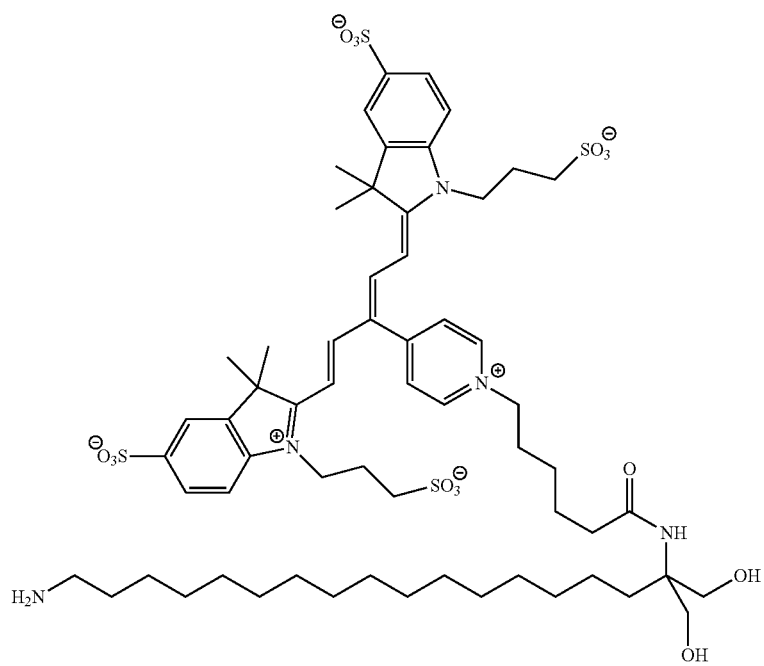
65
The Cy001 NHS ester 35 was synthesized in the Klinik and Poliklinik für Nuklearmedizin, WWU Münster.

37
Structure of Cy001 NHS ester

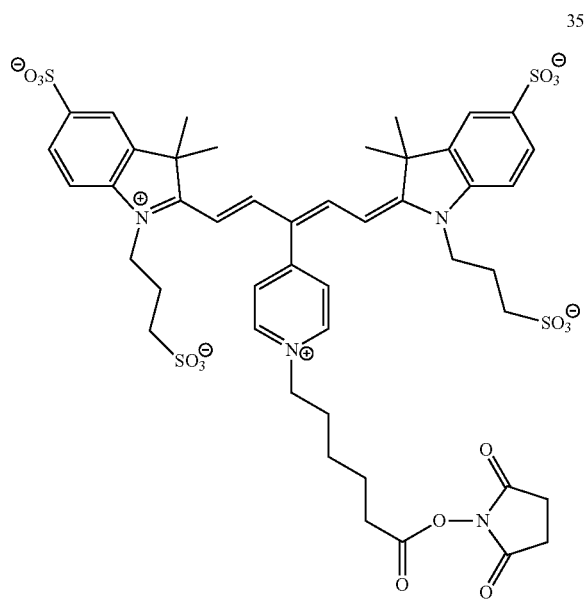

7. Synthesis of 2-Tetradecyl-2-aminopropane-1,3-diol (SSS 943)

7.1 tert-Butyl N-[5-(hydroxymethyl)-2,2-dimethyl-1,3-dioxan-5-yl]-carbamate

Tris(hydroxymethyl)aminomethane (2.50 g, 20.6 mmol) was suspended in DMF (50 mL) and Boc anhydride (5.00 g, 22.7 mmol, 1.1 eq.) was added. The reaction mixture was stirred for 2 h at r.t. Then dimethoxypropane (3.0 mL, 24.8 mmol, 1.2 eq.) and para-toluenesulfonic acid monohydrate (200 mg, 1.04 mmol, 0.1 eq.) were added and the resulting mixture was stirred overnight at r.t. The reaction was quenched by addition of diethyl ether (50 mL). The organic phase was washed with saturated sodium bicarbonate solution (1×30 mL) and brine (1×20 mL) and then dried over $Na_2SO_4$. The solvent was removed under reduced pressure. The product was obtained as white solid and was used without purification in the next step.

Yield: 5.38 g, (95%), purity: 91% (GC).

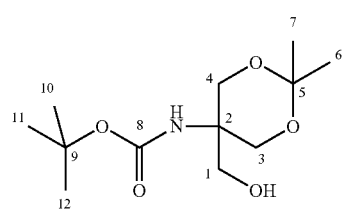

M.p.: 100° C. (lit. 100-102° C.)

$^1$H-NMR (300 MHz, $CDCl_3$) δ [ppm]: 1.38-1.52 (m, 15H, 6-$CH_3$, 7-$CH_3$, 10-$CH_3$ to 12-$CH_3$), 3.61-4.06 (m, 6H, 1-$CH_2$, 3-$CH_2$, 4-$CH_2$), 4.18 (s, 1H, 2-NH).

$^{13}$C-NMR (75 MHz, $CDCl_3$) δ [ppm]: 28.0 (q, C-10, C-11, C-12), 30.6 (q, C-6, C-7), 59.8 (s, C-2), 62.2 (t, C-3, C-4), 62.9 (t, C-1), 80.0 (s, C-9), 98.4 (s, C-5), 162.9 (s, C-8).

Exact mass (ESI$^+$): $C_{12}H_{23}NO_5$+H$^+$: calcd. 262.1649. found: 262.1650. $C_{12}H_{23}NO_5$+Na$^+$: calcd. 284.1468. found: 284.1468.

Ref.: Synthesis according to H. Ooi, N. Ishibashi, Y. Iwabuchi, J. Ishihara, S. Hatakeyama, J. Org. Chem. 2004, 69, 7765-7768.

Spectroscopic data agree with those given in the literature.

7.2 tert-Butyl N-(5-formyl-2,2-dimethyl-1,3-dioxan-5-yl)carbamate

A solution of oxalyl chloride (1.1 mL, 12.4 mmol, 2.0 eq.) in dry dichloromethane (20 mL) was cooled down to −78° C. and then treated with DMSO (1.3 mL, 18.6 mmol, 3.0 eq.). After 30 min a solution of alcohol 36 (1.89 g, 6.20 mmol) in dry dichloromethane (20 mL) was added and stirring was continued for additional 30 min. Triethylamine (5.2 mL, 37.2 mmol, 6.0 eq.) was dripped into the reaction mixture which was then allowed to warm up to r.t. The organic phase was washed with 1 M hydrochloric acid (1×8 mL) and brine (1×10 mL) and then dried over $Na_2SO_4$. The solvent was removed in vacuo and the crude product was purified via column chromatography (silica gel, 11×3 cm, cyclohexane/ethyl acetate, 2:1). The product was obtained as white solid. Yield: 1.63 g (91%), purity: 90% (GC).

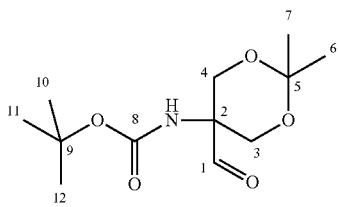

M.p.: 119° C. (lit. 116-119° C.)

$^1$H-NMR (300 MHz, $CDCl_3$) δ [ppm]: 1.43 (s, 6H, 6-$CH_3$, 7-$CH_3$), 1.47 (s, 9H, 10-$CH_3$, 11-$CH_3$, 12-$CH_3$), 3.96 (d, $^2J_{H,H}$=11.8 Hz, 2H, 3-$CH_2$, 4-$CH_2$), 4.07 (d, $^2J_{H,H}$=11.9 Hz, 2H, 3-$CH_2$, 4-$CH_2$), 5.63 (s, 1H, 2-NH), 9.63 (s, 1H, 1-CHO).

$^{13}$C-NMR (75 MHz, $CDCl_3$) δ [ppm]: 27.0 (q, C-6, C-7), 28.3 (q, C-10, C-11, C-12), 59.9 (s, C-2), 62.7 (t, C-3, C-4), 81.0 (s, C-9), 98.8 (s, C-5), 155.5 (s, C-8), 199.4 (d, C-1).

Exact mass (ESI$^+$): $C_{12}H_{21}NO_5$+H$^+$: calcd. 260.14925. found 260.14975. $C_{12}H_{13}NO_5$+Na$^+$: calcd. 282.13119. found 282.13171.

Ref.: Synthesis according to H. Ooi, N. Ishibashi, Y. Iwabuchi, J. Ishihara, S. Hatakeyama, J. Org. Chem. 2004, 69, 7765-7768.

Spectroscopic data agree with those given in the literature.

7.3 tert-Butyl N-(2,2-dimethyl-5-tetradecyl-1,3-dioxan-5-yl)carbamate

Aldehyde 37 (432 mg, 1.55 mmol) was dissolved in 1,4-dioxane (5 mL) and tridecane triphenylphosphonium bromide (895 mg, 1.71 mmol, 1.1 eq.) and potassium carbonate (450 mg, 3.26 mmol, 2.1 eq.) were added. The resulting mixture was heated to 110° C. for 24 h. After cooling to r.t. the mixture was adsorbed on silica gel (2 g) and triphenylphosphine oxide was removed by column filtration (3×2 cm, pentane). The formation of alkene 38 was verified by mass spectrometry and the crude product was directly used in the next reaction. Ultrapure hydrogen gas was generated with a Nitrox UHP-40H hydrogen generator (DOMNICK HUNTER, England).

Alkene 38 (334 mg, 0.78 mmol) was dissolved in THF (10 mL) and the catalyst (10% palladium on activated carbon, 98 mg, 29 wt %) was added. The vessel was flushed with hydrogen and the mixture was stirred 2 days at r.t. under a hydrogen pressure of 2 bar. The reaction was stopped by releasing the hydrogen gas and filtration of the catalyst over Celite®. The solvent was removed and the residue was analyzed by mass spectrometry. As there was still starting material remaining, half of the residue (172 mg) was dissolved in methanol (6 mL), and was hydrogenated again overnight (catalyst: 10% palladium on activated carbon 52 mg, 30 wt %; hydrogen pressure 2 bar). The reaction was worked up as described above and the product 39 was purified by column filtration (silica gel, 7.5×2 cm, ethyl acetate) to give a white solid. Yield: 172 mg (13% over two steps).

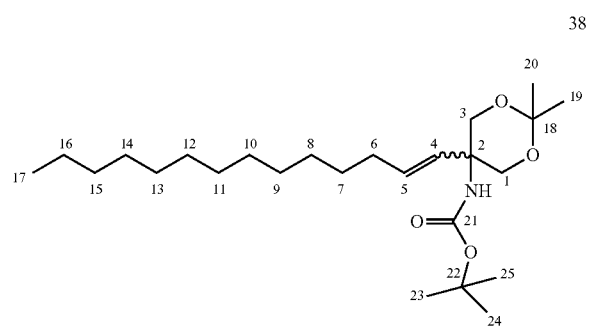 [SMILES: CCCCCCCCCCCCC=CC1(NC(=O)OC(C)(C)C)COC(C)(C)OC1]

Exact mass (ESI$^+$): C$_{25}$H$_{47}$NO$_4$+H$^+$: calcd. 426.3578. found 426.3569. C$_{25}$H$_{47}$NO$_4$+Na$^+$: calcd. 448.3397. found 448.3385. (C$_{25}$H$_{47}$NO$_4$)$_2$+Na$^+$: calcd. 873.6902. found 873.6890.

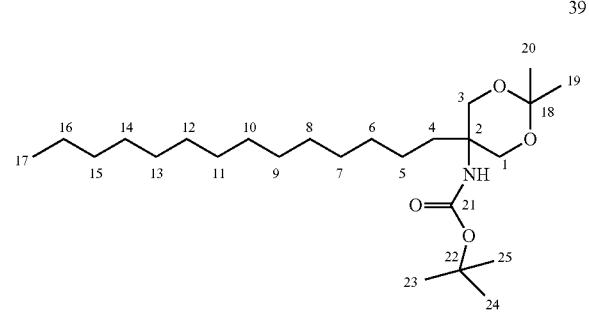 [SMILES: CCCCCCCCCCCCCCC1(NC(=O)OC(C)(C)C)COC(C)(C)OC1]

M.p.: 60° C.
$^1$H-NMR (300 MHz, CDCl$_3$) δ [ppm]: 0.87 (m, 3H, 17-CH$_3$), 1.21-1.30 (m, 24H, 5-CH$_2$ to 16-CH$_2$), 1.40-1.46 (m, 15H, 19-CH$_3$, 20-CH$_3$, 23-CH$_3$ to 25-CH$_3$), 1.65 (m, 2H, 4-CH$_2$), 3.64 (d, $^2J_{H,H}$=12.0 Hz, 2H, 1-CH$_2$, 3-CH$_2$), 3.90 (d, $^2J_{H,H}$=11.7 Hz, 2H, 1-CH$_2$, 3-CH$_2$), 4.87 (s, 1H, 2-NH).
$^{13}$C-NMR (75 MHz, CDCl$_3$) δ [ppm]: 14.3 (q, C-17), 22.5, 22.8 (t, C-5, C-16), 27.3 (q, C-19, C-20), 28.5 (q, C-23 to C-25), 29.5, 29.6, 29.7, 29.8, 30.0 (t, C-6 to C-15), 32.1 (t, C-4), 51.7 (s, C-2), 66.4 (t, C-1, C-3), 79.3 (s, C-22), 98.4 (s, C-18), 155.0 (s, C-21).
Exact mass (ESI$^+$): C$_{25}$H$_{49}$NO$_4$+H$^+$: calcd. 428.3734. found 428.3732. C$_{25}$H$_{49}$NO$_4$+Na$^+$: calcd. 450.3554. found 450.3549.

7.4 2-Amino-2-tetradecylpropane-1,3-diol (SSS 943)

Boc-protected aminodiol 39 (79 mg, 0.18 mmol) was dissolved in a mixture of dichloromethane, TFA and water (2:2:1, v/v, 2.5 mL) and stirred at r.t. overnight. The reaction was quenched with saturated bicarbonate solution (5 mL) and the aqueous phase was extracted with dichloromethane (4×8 mL). The combined organic phases were washed with brine (1×5 mL), dried over Na$_2$SO$_4$ and concentrated in vacuo. The residue was crystallized from ethyl acetate to give a white solid. Yield: 30 mg (58%).

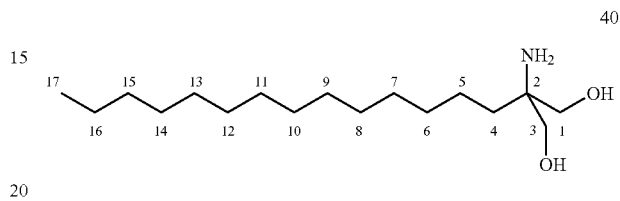

M.p.: 78-80° C.
$^1$H-NMR (400 MHz, CD$_3$OD, CDCl$_3$) δ [ppm]: 0.89 (t, $^3J_{H,H}$=6.7 Hz, 3H, 17-CH$_3$), 1.17-1.46 (m, 26H, 4-CH$_2$ to 16-CH$_2$), 3.41 (d, $^2J_{H,H}$=10.8 Hz, 2H, 1-CH$_2$, 3-CH$_2$), 3.47 (d, $^2J_{H,H}$=10.8 Hz, 2H, 1-CH$_2$, 3-CH$_2$).
$^{13}$C-NMR (101 MHz, CD$_3$OD, CDCl$_3$) δ [ppm]: 14.4 (q, C-17), 23.6 (t, C-16), 23.8 (t, C-5), 30.3, 30.6, 31.4 (t, C-6 to C-14), 32.9 (t, C-15), 34.9 (t, C-4), 57.0 (s, C-2), 66.1 (t, C-1, C-3).
Exact mass (ESI$^+$): C$_{17}$H$_{37}$NO$_2$+H$^+$: calcd. 288.2897. found 288.2900. C$_{17}$H$_{37}$NO$_2$+Na$^+$: calcd. 310.2717. found 310.2717.
Ref.: Reaction procedure is taken from S. Kim, H. Lee, M. Lee, T. Lee, *Synthesis* 2006, 5, 753-755.

8. Synthesis of the Unsaturated Derivatives 8.1 Tetradecanal

A solution of oxalylchloride (8.0 mL, 88.0 mmol, 2.2 eq.) in abs. dichloromethane (200 mL) was treated with DMSO (13.6 mL, 192 mmol, 4.8 eq.) at −60° C. After 3 min the reaction mixture was warmed to approx. 15° C. Then a solution of tetradecan-1-ol (8.56 g, 40.0 mmol) in dry dichloromethane (40 mL) and after further 3 min triethylamine (28 mL, 200 mmol, 5.0 eq.) were added. Then the reaction mixture was slowly warmed to 5° C. and quenched by addition of water (200 mL). The phases were separated and the aqueous phase was extracted with dichloromethane (3×100 mL). The combined organic phases were washed with brine (1×200 mL) and dried over MgSO$_4$. The solvent was removed under reduced pressure and the product was isolated as a white solid, which was used in the next reaction without purification. Yield: 10.4 g (100%), purity: 98% (GC).

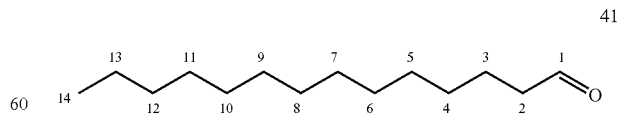

M.p.: 24° C.
$^1$H-NMR (CDCl$_3$, 300 MHz) δ [ppm]: 0.88 (t, $^3J_{H,H}$=6.7 Hz, 3H, 14-CH$_3$), 1.20-1.40 (m, 20H, 4-CH$_2$ to 13-CH$_2$), 1.63 (m, 2H, 3-CH$_2$), 2.43 (m, 2H, 2-CH$_2$), 9.76 (t, $^3J_{H,H}$=1.8 Hz, 1H, 1-CHO).

$^{13}$C-NMR (CDCl$_3$, 75 MHz) δ [ppm]: 14.0 (q, C-14), 22.0 (t, C-3), 22.6 (t, C-13), 29.2, 29.4, 29.5, 29.6, 29.7 (t, C-4 to C-11), 31.9 (t, C-12), 43.8 (t, C-2), 202.8 (d, C-1).

Ref.: Synthesis according to G. S, Nikolova, *Dissertation*, Universität Münster, 2005.

Spectroscopic data agree with those given in the literature.

8.2 Ethyl 2-(diethoxyphosphoryl)acetate

Ethyl 2-bromoacetate (11 mL, 100 mmol) and triethylphosphite (17 mL, 100 mmol) were heated to 80° C. and stirred overnight. Ethylbromide, formed during the reaction, was directly distilled off via a vigreux column. The product was obtained as colourless liquid and was used without purification. Yield: 20.2 g (90%), purity 98% (GC).

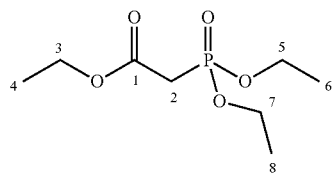

42

$^1$H-NMR (300 MHz, CDCl$_3$) δ [ppm]: 1.29 (t, $^3J_{H,H}$=7.1 Hz, 3H, 4-CH$_3$), 1.35 (td, $^4J_{H,P}$=0.6 Hz, $^3J_{H,H}$=7.1 Hz, 6H, 6-CH$_3$, 8-CH$_3$), 2.97 (d, $^2J_{H,P}$=21.6 Hz, 2H, 2-CH$_2$), 4.12-4.25 (m, 6H, 3-CH$_2$, 5-CH$_2$, 7-CH$_2$).

$^{13}$C-NMR (75 MHz, CDCl$_3$) δ [ppm]: 14.1 (q, C-4), 16.3 (dq, $^3J_{C,P}$=6.3 Hz, C-6, C-8), 34.4 (dt, $^1J_{C,P}$=134.2 Hz, C-2), 61.5 (t, C-3), 62.6 (dt, $^2J_{C,P}$=6.3 Hz, C-5, C-7), 165.8 (d, $^2J_{C,P}$=6.1 Hz, C-1).

$^{31}$P-NMR (121 MHz, CDCl$_3$) δ [ppm]: 19.7 (s, 1P, 2-CH$_2$P).

8.3 (E)-Ethyl hexadec-2-enoate

Phosphonic acid ethyl ester 42 (7.07 g, 31.5 mmol) was dissolved in dry THF (100 mL) and was cooled down to 0° C. Sodium hydride (60%, 1.39 g, 34.7 mmol, 1.1 eq.) was added and the mixture was stirred at this temperature for 30 min. The mixture was warmed to r.t and then a solution of tetradecal (41, 8.75 g, 31.5 mmol, 1.0 eq.), obtained as in example 8.1, in dry THF (60 mL) was dripped into the mixture. The mixture was stirred for 2 h and afterwards the reaction was quenched by addition of brine (150 mL). The phases were separated and the aqueous layer was extracted with ethyl acetate (3×50 mL). The organic phases were collected, dried over MgSO$_4$ and concentrated under reduced pressure. The product was used in the next reaction without purification. Yield: 9.76 g (81%), purity: 74% (GC).

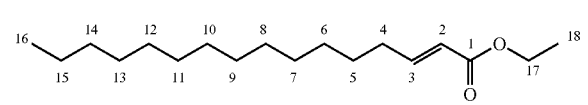

43

$^1$H-NMR (300 MHz, CDCl$_3$) δ [ppm]: 0.87 (m, 3H, 16-CH$_3$), 1.20-1.49 (m, 25H, 5-CH$_2$ to 15 CH$_2$, 18-CH$_3$), 2.19 (m, 2H, 4-CH$_2$), 4.17 (q, $^3J_{H,H}$=7.2 Hz, 2H, 17-CH$_2$), 5.81 (dt, $^4J_{H,H}$=1.6 Hz, $^3J_{H,H}$=15.6 Hz, 1H, 2-CH), 6.97 (dt, $^3J_{H,H}$=6.9 Hz, $^3J_{H,H}$=15.6 Hz, 1H, 3-CH).

8.4 (E)-Hexadec-2-en-1-ol

Ester 43 (9.67 g, 25.3 mmol, purity:74% (GC)) was dissolved in abs. THF (30 mL) and slowly treated with DIBAL-H (1 M solution in heptane, 79 mL, 79.0 mmol, 3.1 eq.) at 0° C. The reaction mixture was allowed to warm up to r.t. overnight and was quenched by addition of water (40 mL) and 2 M hydrochloric acid (10 mL). The phases were separated and the aqueous phase was extracted with ethyl acetate (3×20 mL). The organic layers were collected, dried over Na$_2$SO$_4$ and evaporated. The residue was purified by column chromatography (silica gel, 21×5 cm, cyclohexane/ethyl acetate, 10:1) and the product was isolated as waxy solid. Yield: 5.00 g (69%), purity: 84% (GC).

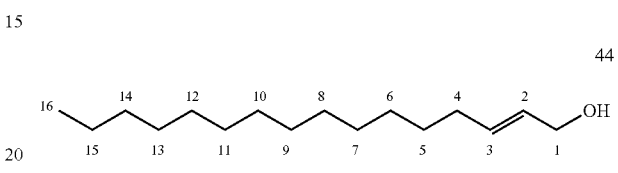

44

M.p.: 40° C.

$^1$H-NMR (300 MHz, CDCl$_3$) δ [ppm]: 0.87 (m, 3H, 16-CH$_3$), 1.19-1.42 (m, 22H, 5-CH$_2$ to 15-CH$_2$), 1.68 (m, 1H, 1-OH), 2.04 (q, $^3J_{H,H}$=6.8 Hz, 2H, 4-CH$_2$), 4.07 (d, $^3J_{H,H}$=4.8 Hz, 2H, 1-CH$_2$), 5.57-5.76 (m, 2H, 2-CH, 3-CH).

$^{13}$C-NMR (75 MHz, CDCl$_3$) δ [ppm]: 14.2 (q, C-16), 22.8 (t, C-15), 29.3, 29.5, 29.6, 29.8 (t, C-5 to C-13), 32.1, 32.4 (t, C-4, C-14), 63.9 (t, C-1), 128.9, 133.6 (d, C-2, C-3).

8.5 (E)-1-Bromohexadec-2-ene

Allylic alcohol 44 (7.22 g, 30.0 mmol) and triphenylphosphine (7.87 g, 30.0 mmol, 1.0 eq.) were dissolved in dichloromethane (60 mL) and cooled down to −20° C. NBS (6.41 g, 36.0 mmol, 1.2 eq.) was added in portions and the mixture was warmed to r.t. and stirred for additional 2 h. Then the volume of the mixture was halved and the remainder was diluted with pentane (200 mL). Triphenylphosphine oxide was filtered off and the organic layer was washed with water (80 mL) and dried over MgSO$_4$. The solvent was removed and the residue was adsorbed on silica gel for purification. After column chromatography (13×5 cm, cyclohexane→ethyl acetate) the bromide 45 was isolated as viscous oil. Yield: 6.14 g (68%).

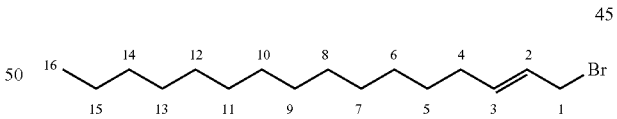

45

$^1$H-NMR (300 MHz, CDCl$_3$) δ [ppm]: 0.87 (m, 3H, 16-CH$_3$), 1.23-1.34 (m, 22H, 5-CH$_2$ to 15-CH$_2$), 2.05 (q, $^3J_{H,H}$=6.6 Hz, 2H, 4-CH$_2$), 3.95 (d, $^3J_{H,H}$=7.0 Hz, 2H, 1-CH$_2$), 5.62-5.83 (m, 2H, 2-CH, 3-CH).

$^{13}$C-NMR (75 MHz, CDCl$_3$) δ [ppm]: 14.3 (q, C-16), 22.9 (t, C-15), 29.0, 29.3, 29.5, 29.6, 29.7, 29.8 (t, C-5 to C-13), 32.1, 32.2 (t, C-4, C-14), 33.8 (t, C-1), 126.4, 136.9 (d, C-2, C-3).

8.6 (E)-Diethyl 2-acetamido-2-(hexadec-2-en-1-yl) malonate

Diethyl 2-acetamidomalonate 1 (4.06 g, 18.7 mmol, 1.0 eq.) obtained as in example 1.1, bromide 45 (5.67 g, 18.7 mmol) and caesium carbonate (7.21 g, 22.2 mmol, 1.2 eq.) were suspended in acetonitrile (100 mL) and refluxed for 8 h. After cooling to r.t. the precipitate was filtered off and the solvent was removed in vacuo. The product was crystallized from pentane and obtained as white solid. Yield: 6.24 g (76%).

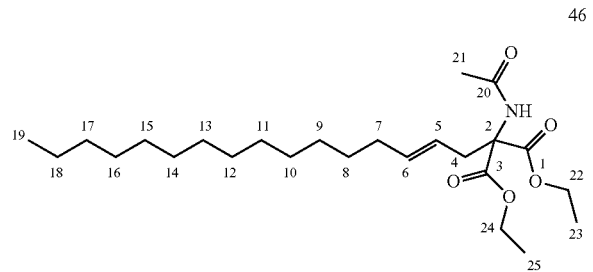 [SMILES: CCCCCCCCCCCCC/C=C/CC(NC(C)=O)(C(=O)OCC)C(=O)OCC]

M.p.: 56° C.

$^1$H-NMR (300 MHz, CDCl$_3$) δ [ppm]: 0.88 (t, $^3J_{H,H}$=6.7 Hz, 3H, 19-CH$_3$), 1.21-1.33 (m, 28H, 8-CH$_2$ to 18-CH$_2$, 23-CH$_3$, 25-CH$_3$), 1.95 (q, $^3J_{H,H}$=6.8 Hz, 2H, 7-CH$_2$), 2.03 (s, 3H, 21-CH$_3$), 3.00 (d, $^3J_{H,H}$=7.4 Hz, 2H, 4-CH$_2$), 4.23 (q, $^3J_{H,H}$=7.1 Hz, 4H, 22-CH$_2$, 24-CH$_2$), 5.15 (dt, $^3J_{H,H}$=7.4 Hz, $^3J_{H,H}$=15.1 Hz, 1H, 5-CH), 5.49 (dt, $^3J_{H,H}$=6.9 Hz, $^3J_{H,H}$=15.1 Hz, 1H, 6-CH), 6.74 (s, 1H, 2-NH).

$^{13}$C-NMR (75 MHz, CDCl$_3$) δ [ppm]: 14.1 (q, C-23, C-25), 14.2 (q, C-19), 22.8 (t, C-18), 23.1 (q, C-21), 29.2, 29.4, 29.5, 29.6, 29.7, 29.8 (t, C-8 to C-16), 32.0, 32.7 (t, C-7, C-17), 35.9 (t, C-4), 62.5 (t, C-22, C-24), 66.6 (s, C-2), 122.3, 136.4 (d, C-5, C-6), 167.8 (s, C-1, C-3), 168.9 (s, C-20).

Exact mass (ESI$^+$): C$_{25}$H$_{45}$NO$_5$+Na$^+$: calcd. 462.3190. found 462.3190. (C$_{25}$H$_{45}$NO$_5$)$_2$+Na$^+$: calcd. 901.6488. found 901.6476.

8.7 (E)-N-(1-Hydroxy-2-(hydroxymethyl)octadec-4-en-2-yl)acetamide

Ester 46 (2.86 g, 6.51 mmol) was dissolved in THF (40 mL) and lithium chloride (1.38 g, 32.6 mmol, 5.0 eq.) and sodium borohydride (1.23 g, 32.6 mmol, 5.0 eq.) were added. The mixture was cooled to 0° C. and treated with ethanol (80 mL). After 30 min the mixture was warmed to r.t. and stirred for 4 d. The reaction was quenched with 20% potassium sodium tartrate solution (20 mL). The aqueous phase was extracted with dichloromethane (3×20 mL) and the combined organic layers were dried over Na$_2$SO$_4$. The solvent was removed under reduced pressure and the residue was purified by column chromatography (silica gel, 11.5×4 cm, ethyl acetate). Product 47 was isolated as white solid. Yield: 1.58 g (68%).

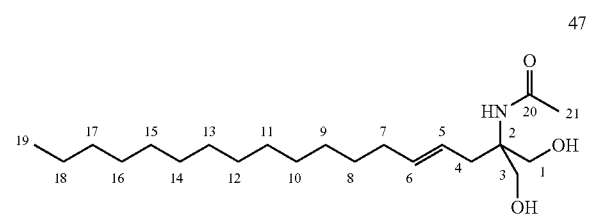 [SMILES: CCCCCCCCCCCCC/C=C/CC(CO)(CO)NC(C)=O]

M.p.: 84° C.

$^1$H-NMR (400 MHz, CDCl$_3$) δ [ppm]: 0.88 (t, $^3J_{H,H}$=6.9 Hz, 3H, 19-CH$_3$), 1.13-1.38 (m, 22H, 8-CH$_2$ to 18-CH$_2$), 1.99-2.06 (m, 5H, 7-CH$_2$, 21-CH$_3$), 2.30 (d, $^3J_{H,H}$=7.3 Hz, 2H, 4-CH$_2$), 3.55 (d, $^2J_{H,H}$=11.6 Hz, 2H, 1-CH$_2$, 3-CH$_2$), 3.76 (d, $^2J_{H,H}$=11.6 Hz, 2H, 1-CH$_2$, 3-CH$_2$), 4.47 (br s, 2H, 1-OH, 3-OH), 5.41 (dt, $^3J_{H,H}$=7.4 Hz, $^3J_{H,H}$=15.1 Hz, 1H, 5-CH), 5.57 (dt, $^3J_{H,H}$=6.7 Hz, $^3J_{H,H}$=15.2 Hz, 1H, 6-CH), 6.09 (s, 1H, 2-NH).

$^{13}$C-NMR (101 MHz, CDCl$_3$) δ [ppm]: 14.2 (q, C-19), 22.8 (t, C-18), 24.0 (q, C-21), 29.3, 29.5, 29.6, 29.7, 29.8 (t, C-8 to C-16), 32.0, 32.8 (t, C-7, C-17), 36.1 (t, C-4), 61.0 (s, C-2), 65.4 (t, C-1, C-3), 123.4, 136.7 (d, C-5, C-6), 171.9 (s, C-20).

Exact mass (ESI$^+$): C$_{21}$H$_{41}$NO$_3$+H$^+$: calcd. 356.3159. found 356.3161. C$_{21}$H$_{41}$NO$_3$+Na$^+$: calcd. 378.2979. found 378.2978. (C$_{21}$H$_{41}$NO$_3$)$_2$+Na$^+$: calcd. 733.6065. found 733.6049.

8.8 (E)-2-Amino-2-(hexadec-2-en-1-yl)propane-1,3-diol (SSS 822)

Protected aminodiol 47 (186 mg, 0.52 mmol) was dissolved in methanol (5 mL), treated with 1 M sodium hydroxide solution (1.0 mL, 1.0 mmol, 1.9 eq.) and heated to reflux for 5 h. After cooling to r.t. overnight the mixture was diluted with 1 M sodium hydroxide solution (5 mL) and the aqueous phase was extracted with dichloromethane (5×10 mL). The combined organic layers were dried over Na$_2$SO$_4$ and concentrated in vacuo. The product was crystallized from ethyl acetate and isolated as white solid. Yield: 158 mg (97%).

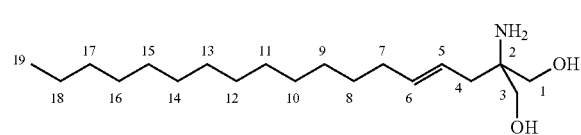

M.p.: 57° C.

$^1$H-NMR (300 MHz, CD$_3$OD) δ [ppm]: 0.90 (t, $^3J_{H,H}$=6.7 Hz, 3H, 19-CH$_3$), 1.29 (m, 22H, 8-CH$_2$ to 18-CH$_2$), 2.03 (q, $^3J_{H,H}$=6.6 Hz, 2H, 7-CH$_2$), 2.09 (d, $^3J_{H,H}$=6.7 Hz, 2H, 4-CH$_2$), 3.38 (d, $^2J_{H,H}$=10.8 Hz, 2H, 1-CH$_2$, 3-CH$_2$), 3.41 (d, $^2J_{H,H}$=10.8 Hz, 2H, 1-CH$_2$, 3-CH$_2$), 5.49 (m, 2H, 5-CH, 6-CH).

$^{13}$C-NMR (75 MHz, CD$_3$OD) δ [ppm]: 14.5 (q, C-19), 23.8 (t, C-18), 30.3, 30.5, 30.7, 30.8 (t, C-8 to C-16), 33.1, 33.8 (t, C-7, C-17), 38.2 (t, C-4), 56.8 (s, C-2), 66.5 (t, C-1, C-3), 125.5 136.0 (d, C-5, C-6).

Exact mass (ESI$^+$): C$_{19}$H$_{39}$NO$_2$+H$^+$: calcd. 314.3054. found 314.3071. C$_{19}$H$_{39}$NO$_2$+Na$^+$: calcd. 336.2873. found 336.2874. (C$_{19}$H$_{39}$NO$_2$)$_2$+Na$^+$: calcd. 649.5854. found 649.5850.

9. Synthesis of the Unsaturated 4-Fluoro Compounds

9.1 (Ethoxycarbonylfluoromethyl)triphenylphosphonium bromide

A solution of triphenylphosphine (7.08 g, 27.0 mmol) in dry dichloromethane (20 mL) was treated dropwise with ethyl 2-bromo-2-fluoroacetate (5.00 g, 27.0 mmol). The reaction mixture was stirred at r.t. for 6 days. Afterwards the solvent was removed and the highly viscous foam was dried in high vacuum and used in the next reaction without purification.

Yield: 11.43 g (94% crude).

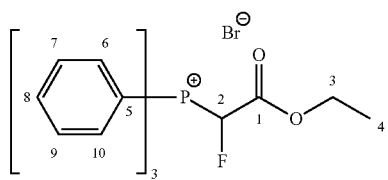

49

$^1$H-NMR (300 MHz, CDCl$_3$) δ [ppm]: 0.97 (t, $^3J_{H,H}$=7.1 Hz, 3H, 4-CH$_3$), 4.09 (qd, $^2J_{H,H}$=2.6 Hz, $^3J_{H,H}$=7.2 Hz, 2H, 3-CH$_2$), 7.66-7.78 (m, 6H, 6-CH, 10-CH), 7.80-7.90 (m, 3H, 8-CH), 7.91-8.00 (m, 6H, 7-CH, 9-CH), 9.24 (dd, $^3J_{H,P}$=5.8 Hz, $^2J_{H,F}$=42.0 Hz, 1H, 2-CH).

$^{13}$C-NMR (75 MHz, CDCl$_3$) δ [ppm]: 13.5 (q, C-4), 63.7 (t, C-3), 85.0 (ddd, $^1J_{C,P}$=59.9 Hz, $^1J_{C,F}$=212.4 Hz, C-2), 114.8 (d, $^1J_{C,P}$=86.3 Hz, C-5), 130.4 (dd, $^3J_{C,P}$=13.3 Hz, C-7, C-9), 134.5 (dd, $^3J_{C,P}$=10.5 Hz, C-6, C-10), 135.8 (dd, $^4J_{C,P}$=3.2 Hz, C-8), 163.1 (dd, $^3J_{C,P}$=2.4 Hz, $^2J_{C,F}$=21.5 Hz, C-1).

$^{19}$F-NMR (282 MHz, CDCl$_3$) δ [ppm]: −202.4 (dd, $^2J_{H,F}$=42.0 Hz, $^2J_{P,F}$=68.0 Hz, 1F, 2-CHF). $^{31}$P-NMR (121 MHz, CDCl$_3$)) δ [ppm]: 24.9 (d, $^2J_{P,F}$=67.9 Hz, 1P, 2-CFP).

Refs.: Synthesis according to G. S, Nikolova, *Dissertation*, Universität Münster, 2005.

Spectroscopic data agree with those given in the literature by a) A. Thenappan, D. J. Burton, *J. Org. Chem.* 1990, 55, 2311-2317; b) Z.-Q. Xu, Y.-L. Qui, S. Chokekjchai, H. Mitsuya, J. Zemlicka, *J. Med. Chem.* 1995, 38, 875-882.

9.2 Ethyl 2-fluorohexadec-2-enoate

Phosphonium bromide 49 (11.06 g, 25.8 mmol, 1.2 eq.) was suspended in dry THF (70 mL), cooled down to 0° C. and treated with n-butyl lithium (1.6 M solution in n-hexane, 14.8 mL, 23.6 mmol, 1.1 eq.). After 1 h tetradecanal 41 (4.56 g, 21.5 mmol) obtained as in example 8.1, dissolved in dry THF (42 mL), was added. The mixture was warmed to r.t. and stirred for an additional hour. The reaction was stopped by addition of saturated ammonium chloride solution (60 mL). The phases were separated and the aqueous phase was extracted with diethyl ether (2×80 mL). The organic layers were collected, dried over MgSO$_4$, and concentrated in vacuo. The residue was suspended in pentane and filtered to remove triphenylphosphine oxide. The filtrate was concentrated and the crude product was used in the next step without purification due to instability towards silica gel. Yield: 6.83 g (77%), purity: 73% (GC).

50

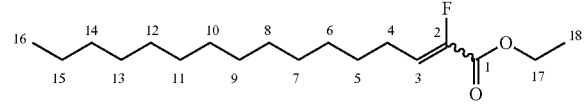

E/Z-ratio: 34:66 (GC)

$^1$H-NMR (300 MHz, CDCl$_3$) δ [ppm]: 0.88 (t, $^3J_{H,H}$=6.6 Hz, 3H, 16-CH$_3$), 1.03-1.65 (m, 25H, 5-CH$_2$ to 15-CH$_2$, 18-CH$_3$), 2.23 (dq, $^3J_{H,H}$=7.1 Hz, $^4J_{H,F}$=1.9 Hz, 2H, (Z)-4-CH$_2$), 2.50 (dq, $^3J_{H,H}$=8.0 Hz, $^4J_{H,F}$=1.7 Hz, 2H, (E)-4-CH$_2$), 4.27 (q, $^3J_{H,H}$=7.0 Hz, 2H, 17-CH$_2$), 5.92 (dt, $^3J_{H,H}$=8.3 Hz, $^3J_{H,F}$=21.9 Hz, 2H, (E)-3-CH), 6.12 (dt, $^3J_{H,H}$=7.9 Hz, $^3J_{H,F}$=33.3 Hz, 2H, (Z)-3-CH).

$^{13}$C-NMR (75 MHz, CDCl$_3$) δ [ppm]: 14.2 (q, C-16, C-18), 22.7 (t, C-15), 24.3 (dt, $^3J_{C,F}$=2.5 Hz, (Z)—C-4), 29.2, 29.3, 29.4, 29.6, 29.7, 29.8 (t, C-5 to C-13), 32.0 (t, C-14), 61.5 (t, C-17), 120.9 (dd, $^2J_{C,F}$=11.8 Hz, (Z)—C-3), 123.9 (dd, $^2J_{C,F}$=17.8 Hz, (E)-C-3), 147.0 (d, $^1J_{C,F}$=250.2 Hz, (E)-C-2), 148.0 (d, $^1J_{C,F}$=254.8 Hz, (Z)—C-2), 161.0 (d, $^2J_{C,F}$=35.5 Hz, C-1).

$^{19}$F-NMR (282 MHz, CDCl$_3$) δ [ppm]: −131.6 (dt, $^4J_{H,F}$=2.2 Hz, $^3J_{H,F}$=33.3 Hz, 1F, (Z)-2-CF), −123.2 (dt, $^4J_{H,F}$=1.7 Hz, $^3J_{H,F}$=21.8 Hz, 1F, (E)-2-CF).

Refs.: Synthesis according to G. S, Nikolova, *Dissertation*, Universität Münster, 2005.

Spectroscopic data agree with those given in the literature.

9.3 2-Fluorohexadec-2-en-1-ol

Ethyl 2-fluorohexadec-2-enoate mixture 50 (6.83 g, 16.6 mmol, purity: 73% (GC)) was dissolved in dry THF (23 mL). At 0° C. DIBAL-H (1 M solution in heptane, 56.8 mL, 56.8 mmol, 3.4 eq.) was added dropwise. The reaction mixture was allowed to warm up to r.t. overnight and was poured into water (50 mL). 2 M hydrochloric acid (50 mL) was added and the phases were separated. The aqueous layer was extracted with diethyl ether (3×50 mL) and the combined organic layers were dried over Na$_2$SO$_4$. The solvent was removed under reduced pressure and the residue was purified by column chromatography (silica gel, 27×4 cm, cyclohexane/ethyl acetate, 10:1→5:1). The diastereomeric mixture was isolated as a waxy, white solid. Yield: 2.67 g (61%), purity: 98% (GC).

51

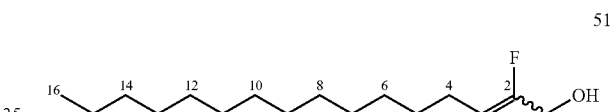

E/Z-ratio: 39:61 (GC) changed due to purification $^1$H-NMR (300 MHz, CDCl$_3$) δ [ppm]: 0.87 (t, $^3J_{H,H}$=6.7 Hz, 3H, 16-CH$_3$), 1.20-1.62 (m, 22H, 5-CH$_2$ to 15-CH$_2$), 2.00 (m, 2H, (E)-4-CH$_2$), 2.14 (m, 2H, (Z)-4-CH$_2$), 4.11 (d, $^3J_{H,F}$=16.1 Hz, 2H, (Z)-1-CH$_2$), 4.22 (d, $^3J_{H,F}$=21.3 Hz, 2H, (E)-1-CH$_2$), 4.82 (dt, $^3J_{H,H}$=7.6 Hz, $^3J_{H,F}$=37.1 Hz, 1H, (Z)-3-CH), 5.20 (dt, $^3J_{H,H}$=8.2 Hz, $^3J_{H,F}$=21.2 Hz, 1H, (E)-3-CH).

$^{19}$F-NMR (282 MHz, CDCl$_3$) δ [ppm]: −122.0 (dtt, $^4J_{H,F}$=1.6 Hz, $^3J_{H,F}$=16.2 Hz, $^3J_{H,F}$=36.9 Hz, 1F, (Z)-2-CF), −115.5 (ps q, $^3J_{H,F}$=21.2 Hz, 1F, (E)-2-CF).

Refs.: Synthesis according to G. S, Nikolova, *Dissertation*, Universität Münster, 2005.

Spectroscopic data agree with those given in the literature.

9.4 2-Fluorohexadec-2-en-1-yl 4-methylbenzenesulfonate

Alcohol 51 (2.36 g, 8.95 mmol, purity: 98% (GC)) was dissolved in dichloromethane (100 mL) and treated with potassium hydroxide (1.33 g, 23.7 mmol, 2.6 eq.). The mixture was cooled to 0° C. and tosyl chloride (3.83 g, 20.1 mmol, 2.2 eq.) was added. After 1 h the mixture was warmed to r.t. and stirred for 2 days. The reaction was stopped by addition of water (50 mL) and the phases were separated. The aqueous layer was extracted with dichloromethane (3×30 mL) and the combined organic layers were dried over MgSO$_4$. The solvent was removed under reduced pressure and the tosylate 52 was purified by column chromatography (silica gel, 35×4 cm, cyclohexane/ethyl acetate, 40:1) and isolated as colourless oil. Yield: 2.14 g (58%).

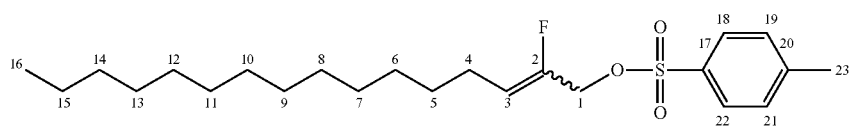

52

E/Z-ratio:15:85 (NMR) changed due to purification $^{1}$H-NMR (300 MHz, CDCl$_3$) δ [ppm]: 0.87 (m, 3H, 16-CH$_3$), 1.18-1.34 (m, 22H, 5-CH$_2$ to 15-CH$_2$), 1.91 (m, 2H, (E)-4-CH$_2$), 2.01 (m, 2H, (Z)-4-CH$_2$), 2.45 (s, 3H, (Z)-23-CH$_3$), 2.49 (s, 3H, (E)-23-CH$_3$), 4.52 (d, $^{3}J_{H,F}$=17.9 Hz, 2H, (Z)-1-CH$_2$), 4.64 (d, $^{3}J_{H,F}$=20.9 Hz, 2H, (E)-1-CH$_2$), 4.92 (dt, $^{3}J_{H,H}$=7.6 Hz, $^{3}J_{H,F}$=34.8 Hz, 1H, (Z)-3-CH), 5.33 (dt, $^{3}J_{H,H}$=8.2 Hz, $^{3}J_{H,F}$=19.6 Hz, 1H, (E)-3-CH), 7.34 (d, $^{3}J_{H,H}$=8.0 Hz, 2H, (Z)-19-CH, (Z)-21-CH), 7.41 (d, $^{3}J_{H,H}$=8.3 Hz, 2H, (E)-19-CH, (E)-21-CH), 7.80 (d, $^{3}J_{H,H}$=8.3 Hz, 2H, (Z)-18-CH, (Z)-22-CH), 7.92 (d, $^{3}J_{H,H}$=8.4 Hz, 2H, (E)-18-CH, (E)-22-CH).

$^{13}$C-NMR (75 MHz, CDCl$_3$) δ [ppm]: 14.3 (q, C-16), 21.8 (q, C-23), 22.8 (t, C-15), 23.8 (dt, $^{3}J_{C,F}$=3.3 Hz, (Z)—C-4), 25.5 (dt, $^{3}J_{C,F}$=7.1 Hz, (E)-C-4), 28.8 (dt, $^{4}J_{C,F}$=1.7 Hz, (Z)—C-5), 29.2, 29.5, 29.7, 29.8 (t, C-6 to C-13), 32.1 (t, C-14), 63.6 (dt, $^{2}J_{C,F}$=31.6 Hz, (E)-C-1), 68.0 (dt, $^{2}J_{C,F}$=31.8 Hz, (Z)—C-1), 114.4 (dd, $^{2}J_{C,F}$=13.5 Hz, (Z)—C-3), 114.7 (dd, $^{2}J_{C,F}$=17.8 Hz, (E)-C-3), 127.2 (d, (E)-C-18, (E)-C-22), 128.1 (d, (Z)—C-18, (Z)—C-22), 130.0 (d, (Z)—C-19, (Z)—C-21), 130.4 (d, (E)-C-19, (E)-C-21), 133.3 (s, C-17), 145.1 (s, C-20), 151.5 (d, $^{1}J_{C,F}$=253.4 Hz, (Z)—C-2).

$^{19}$F-NMR (282 MHz, CDCl$_3$) δ [ppm]: −120.22 (m, 1F, (Z)-2-CF), −112.74 (q, $^{3}J_{H,F}$=20.7 Hz, 1F, (E)-2-CF).

Exact mass (ESI$^{+}$): C$_{23}$H$_{37}$FO$_3$S+Na$^{+}$: calcd. 435.2340. found 435.2340. (C$_{23}$H$_{37}$FO$_3$S)$_2$+Na$^{+}$: calcd. 847.4787. found 847.4777.

9.5 Diethyl 2-acetamido-2-(2-fluorohexadec-2-en-1-yl)malonates

Tosylates 52 (1.90 g, 4.61 mmol), diethyl 2-acetamidomalonate 1 (1.00 g, 4.61 mmol, 1.0 eq.) obtained as in example 1.1 and caesium carbonate (1.78 g, 5.48 mmol, 1.2 eq.) were suspended in acetonitrile (30 mL) and heated to reflux for 6 h. After cooling to r.t. overnight the mixture was filtrated, concentrated in vacuo and purified by column chromatography (silica gel, 40×3 cm, cylohexane/ethyl acetate, 10:1). The diastereomers were separated and obtained as white solids. Yield: 1.40 g (66%, both isomers and a mixed fraction).

(E)-Diethyl 2-acetamido-2-(2-fluorohexadec-2-en-1-yl)malonate

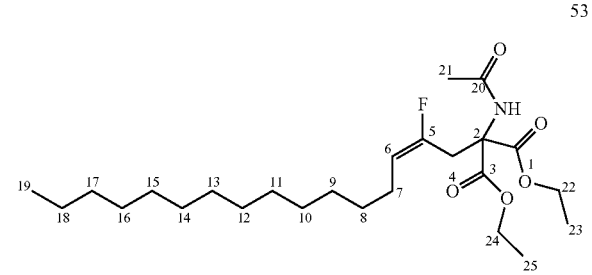 [SMILES: CCCCCCCCCCCCC/C=C(/F)CC(NC(C)=O)(C(=O)OCC)C(=O)OCC]

53

Yield: 148 mg
M.p.: 44° C.

$^{1}$H-NMR (300 MHz, CDCl$_3$) δ [ppm]: 0.88 (t, $^{3}J_{H,H}$=6.8 Hz, 3H, 19-CH$_3$), 1.21-1.30 (m, 28H, 8-CH$_2$ to 18-CH$_2$, 23-CH$_3$, 25-CH$_3$), 1.83 (m, 2H, 7-CH$_2$), 2.01 (s, 3H, 21-CH$_3$), 3.37 (d, $^{3}J_{H,F}$=23.2 Hz, 2H, 4-CH$_2$), 4.26 (q, $^{3}J_{H,H}$=7.1 Hz, 4H, 22-CH$_2$, 24-CH$_2$), 5.18 (dt, $^{3}J_{H,H}$=8.0 Hz, $^{3}J_{H,F}$=22.8 Hz, 1H, 6-CH), 6.87 (s, 1H, 2-NH).

$^{13}$C-NMR (75 MHz, CDCl$_3$) δ [ppm]: 14.0 (q, C-23, C-25), 14.2 (q, C-19), 22.8 (t, C-18), 23.0 (q, C-21), 25.4 (d, $^{3}J_{C,F}$=8.5 Hz, C-7), 29.2, 29.5, 29.6, 29.7, 29.8 (t, C-9 to C-16), 30.1 (dt, $^{4}J_{C,F}$=2.1 Hz, C-8), 32.0 (t, C-17), 32.1 (dt, $^{2}J_{C,F}$=26.0 Hz, C-4), 62.9 (t, C-22, C-24), 64.3 (d, $^{3}J_{C,F}$=3.5 Hz, C-2), 111.3 (dd, $^{2}J_{C,F}$=19.8 Hz, C-6), 154.6 (d, $^{1}J_{C,F}$=243.2 Hz, C-5), 167.6 (s, C-1, C-3), 169.2 (s, C-20).

$^{19}$F-NMR (282 MHz, CDCl$_3$) δ [ppm]: −104.3 (q, $^{3}J_{H,F}$=23.0 Hz, 1F, 5-CF).

Exact mass (ESI$^{+}$): C$_{25}$H$_{44}$FNO$_5$+Na$^{+}$: calcd. 480.3096. found 480.3088. (C$_{25}$H$_{44}$FNO$_5$)$_2$+Na$^{+}$: calcd. 937.6299. found 937.6317.

(Z)-Diethyl 2-acetamido-2-(2-fluorohexadec-2-en-1-yl)malonate

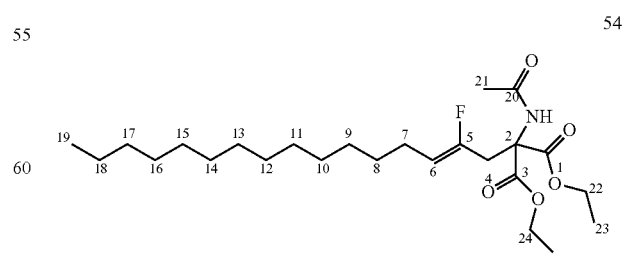

54

Yield: 1.11 g
M.p.: 80° C.

$^1$H-NMR (300 MHz, CDCl$_3$) δ [ppm]: 0.88 (t, $^3J_{H,H}$=6.7 Hz, 3H, 19-CH$_3$), 1.21-1.32 (m, 28H, 8-CH$_2$ to 18-CH$_2$, 23-CH$_3$, 25-CH$_3$), 2.00 (m, 2H, 7-CH$_2$), 2.03 (s, 3H, 21-CH$_3$), 3.26 (d, $^3J_{H,F}$=21.6 Hz, 2H, 4-CH$_2$), 4.26 (2 q, $^3J_{H,H}$=7.1 Hz, 4H, 22-CH$_2$, 24-CH$_2$), 4.57 (dt, $^3J_{H,H}$=7.6 Hz, $^3J_{H,F}$=37.5 Hz, 1H, 6-CH), 6.85 (s, 1H, 2-NH).

$^{13}$C-NMR (75 MHz, CDCl$_3$) δ [ppm]: 14.0 (q, C-23, C-25), 14.2 (q, C-19), 22.8 (t, C-18), 23.0 (q, C-21), 23.7 (dt, $^3J_{C,F}$=4.5 Hz, C-7), 29.2, 29.5, 29.8 (t, C-8 to C-16), 32.0 (t, C-17), 35.9 (dt, $^3J_{C,F}$=25.6 Hz, C-4), 62.9 (t, C-22, C-24), 64.7 (d, $^3J_{C,F}$=3.5 Hz, C-2), 110.7 (dd, $^2J_{C,F}$=15.0 Hz, C-6), 154.4 (d, $^1J_{C,F}$=251.4 Hz, C-5), 167.5 (s, C-1, C-3), 169.2 (s, C-20).

$^{19}$F-NMR (282 MHz, CDCl$_3$) δ [ppm]: −110.6 (dt, $^3J_{H,F}$=21.6 Hz, $^3J_{H,F}$=37.5 Hz, 1F, 5-CF).

Exact mass (ESI$^+$): C$_{25}$H$_{44}$FNO$_5$+Na$^+$: calcd. 480.3096. found 480.3095. (C$_{25}$H$_{44}$FNO$_5$)$_2$+Na$^+$: calcd. 937.6299. found 937.6321.

9.6 (Z)—N-(4-fluoro-1-hydroxy-2-(hydroxymethyl)octadec-4-en-2-yl)acetamide

To a solution of diester 54 (338 mg, 0.74 mmol) in THF (6 mL) lithium chloride (157 mg, 3.70 mmol, 5.0 eq.) and sodium borohydride (140 mg, 3.70 mg, 5.0 eq.) were added. The mixture was cooled to 0° C. and treated with ethanol (12 mL). After 50 min the reaction mixture was warmed to r.t. and stirred for 6 days. The reaction was stopped by addition of 20% potassium sodium tartrate solution (5 mL) and the aqueous phase was extracted with dichloromethane (6×10 mL). The combined organic phases were dried over Na$_2$SO$_4$ and concentrated in vacuo. The residue was purified by column chromatography (silica gel, 11×3 cm, ethyl acetate) and the product was obtained as white solid. Yield: 142 mg (51%). Side product 56 was also found.

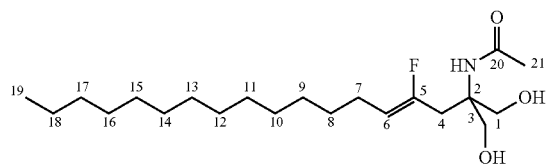

55

M.p.: 86° C.

$^1$H-NMR (300 MHz, CDCl$_3$) δ [ppm]: 0.87 (m, 3H, 19-CH$_3$), 1.24-1.30 (m, 22H, 8-CH$_2$ to 18-CH$_2$), 2.00-2.12 (s, 5H, 7-CH$_2$, 21-CH$_3$), 2.54 (d, $^3J_{H,F}$=23.9 Hz, 2H, 4-CH$_2$), 3.59 (d, $^2J_{H,H}$=11.7 Hz, 2H, 1-CH$_2$, 3-CH$_2$), 3.81 (d, $^2J_{H,H}$=11.7 Hz, 2H, 1-CH$_2$, 3-CH$_2$), 4.72 (dt, $^3J_{H,F}$=7.5, $^3J_{H,F}$=38.6 Hz, 1H, 6-CH), 6.20 (s, 1H, 2-NH).

$^{13}$C-NMR (75 MHz, CDCl$_3$) δ [ppm]: 14.2 (q, C-19), 22.8 (t, C-18), 23.8 (dt, $^3J_{C,F}$=4.6 Hz, C-7), 24.1 (q, C-21), 29.3, 29.4, 29.5, 29.7, 29.8 (t, C-8 to C-16), 32.0 (t, C-17), 35.3 (dt, $^2J_{C,F}$=26.1 Hz, C-4), 60.8 (d, $^3J_{C,F}$=3.8 Hz, C-2), 65.6 (dt, $^4J_{C,F}$=1.8 Hz, C-1, C-3), 111.1 (dd, $^2J_{C,F}$=15.6 Hz, C-6), 155.3 (d, $^1J_{C,F}$=250.4 Hz, C-5), 172.0 (s, C-20).

$^{19}$F-NMR (282 MHz, CDCl$_3$) δ [ppm]: −106.1 (dt, $^3J_{H,F}$=23.9 Hz, $^3J_{H,F}$=38.5 Hz, 1F, 5-CF).

Exact mass (ESI$^+$): C$_{21}$H$_{40}$FNO$_3$+H$^+$: calcd. 374.3065. found 374.3061. C$_{21}$H$_{40}$FNO$_3$+Na$^+$: calcd. 396.2884. found 396.2878. (C$_{21}$H$_{40}$FNO$_3$)$_2$+Na$^+$: calcd. 769.5877. found 769.5878.

Side product 56:

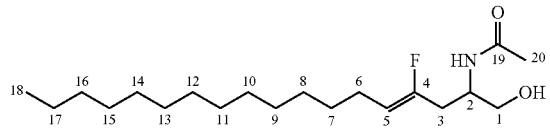

56

Exact mass (ESI+): C$_{20}$H$_{38}$FNO$_2$+Na$^+$: calcd. 366.2779. found 366.2772. (C$_{20}$H$_{38}$FNO$_2$)$_2$+Na$^+$: calcd. 709.5665. found 709.5658.

9.7 (E)-N-(4-fluoro-1-hydroxy-2-(hydroxymethyl)octadec-4-en-2-yl)acetamide

Diester 53 (75 mg, 0.16 mmol) was dissolved in THF (3 mL) and treated with lithium chloride (35 mg, 0.82 mmol, 5.0 eq.) and sodium borohydride (31 mg, 0.82 mmol, 5.0 eq.). The mixture was cooled to 0° C. and ethanol (6 mL) was added. After 35 min the mixture was warmed to r.t. and stirred for 6 days. The reaction was quenched with 20% potassium sodium tartrate solution (5 mL) and the aqueous layer was extracted with dichloromethane (6×10 mL). The combined organic layers were dried over Na$_2$SO$_4$ and concentrated under reduced pressure. Purification by column chromatography (silica gel, 11.5×2 cm, cyclohexane/ethyl acetate, 1:2) gave a mixture of the desired product 57 and the side product 58 which was used in the next reaction without further purification. Also starting material was reisolated. Yield: 30 mg (mixture).

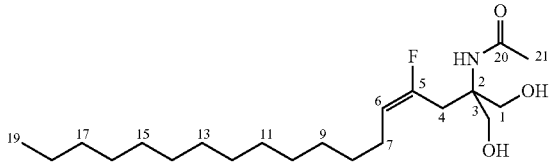

57

$^1$H-NMR (300 MHz, CDCl$_3$) δ [ppm]: 0.88 (t, $^3J_{H,H}$=6.4 Hz, 3H, 19-CH$_3$), 1.23-1.35 (m, 22H, 8-CH$_2$ to 18-CH$_3$), 1.98 (m, 2H, 7-CH$_2$), 2.03 (s, 3H, 21-CH$_3$), 2.63 (d, $^3J_{H,F}$=25.9 Hz, 2H, 4-CH$_2$), 3.56 (d, $^2J_{H,H}$=11.8 Hz, 2H, 1-CH$_2$, 3-CH$_2$), 3.81 (d, $^2J_{H,H}$=11.8 Hz, 2H, 1-CH$_2$, 3-CH$_2$), 5.28 (dt, $^3J_{H,H}$=7.9 Hz, $^3J_{H,F}$=23.7 Hz, 1H, 6-CH), 6.18 (br s, 1H, 2-NH).

$^{13}$C-NMR (75 MHz, CDCl$_3$) δ [ppm]: 14.3 (q, C-19), 22.8 (t, C-18), 24.2 (q, C-21), 25.6 (dt, $^3J_{C,F}$=8.8 Hz, C-7), 29.3, 29.4, 29.5, 29.6, 29.7, 29.8, 30.0, 30.1 (t, C-8 to C-16), 31.4 (dt, $^3J_{C,F}$=26.6 Hz, C-4), 32.1 (t, C-17), 61.1 (d, $^3J_{C,F}$=4.1 Hz, C-2), 65.7 (dt, $^4J_{H,F}$=1.2 Hz, C-1, C-3), 111.4 (dd, $^2J_{C,F}$=20.6 Hz, C-6), 155.7 (d, $^1J_{C,F}$=241.5 Hz, C-5), 172.1 (s, C-20).

$^{19}$F-NMR (282 MHz, CDCl$_3$) δ [ppm]: −99.4 (q, $^3J_{H,F}$=24.7 Hz, $^3J_{H,F}$=25.3 Hz, 1F, 5-CF).

Exact mass (ESI$^+$): C$_{21}$H$_{40}$FNO$_3$+Na$^+$: calcd. 396.2884. found 396.2882. (C$_{21}$H$_{40}$FNO$_3$)$_2$+Na$^+$: calcd. 769.5877. found: 769.5880.

Side product 58:

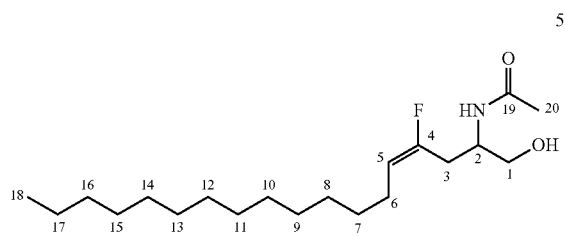

Exact mass (ESI⁺): $C_{20}H_{38}FNO_2+Na^+$: calcd. 366.2779. found 366.2776. $(C_{20}H_{38}FNO_2)_2+Na^+$: calcd. 709.5665. found 709.5667.

9.8 (Z)-2-Amino-2-(2-fluorohexadec-2-en-1-yl)propane-1,3-diol (SSS 862)

Protected aminodiol 55 (61 mg, 0.16 mmol) was dissolved in methanol (5 mL) and treated with 1 M sodium hydroxide solution (0.24 mL, 0.24 mmol, 1.5 eq.). The mixture was heated to reflux for 6 h. After cooling to r.t. the mixture was diluted with 1 M sodium hydroxide solution (10 mL) and the aqueous phase was extracted with dichloromethane (6×10 mL). The combined organic layers were dried over $Na_2SO_4$ and the solvent was removed in vacuo. The product was crystallized from ethyl acetate to give a white solid. Yield: 46 mg (87%).

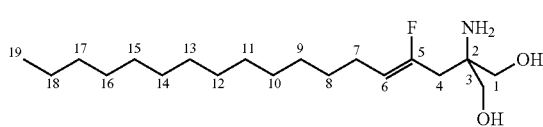

M.p.: 68-70° C.
¹H-NMR (300 MHz, CDCl₃) δ [ppm]: 0.87 (m, 3H, 19-CH₃), 1.20-1.37 (m, 22H, 8-CH₂ to 18-CH₂), 2.05 (m, 2H, 7-CH₂), 2.29 (d, $^3J_{H,F}$=23.9 Hz, 2H, 4-CH₂), 3.43-3.61 (m, 4H, 1-CH₂, 3-CH₂), 4.65 (dt, $^3J_{H,H}$=7.5 Hz, $^3J_{H,F}$=38.1 Hz, 1H, 6-CH).
¹³C-NMR (75 MHz, CD₃OD, CDCl₃) δ [ppm]: 14.3 (q, C-19), 23.2 (t, C-18), 24.1 (dt, $^3J_{C,F}$=4.9 Hz, C-7), 29.7, 29.9, 30.1, 30.2 (t, C-8 to C-16), 32.4 (t, C-17), 37.1 (dt, $^2J_{C,F}$=26.2 Hz, C-4), 56.1 (d, $^3J_{C,F}$=3.6 Hz, C-2), 65.9 (t, C-1, C-3), 110.5 (dd, $^2J_{C,F}$=15.6 Hz, C-6), 156.4 (d, $^1J_{C,F}$=252.2 Hz, C-5).
¹⁹F-NMR (282 MHz, CD₃OD, CDCl₃) δ [ppm]: -104.6 (dt, $^3J_{H,F}$=23.9 Hz, $^3J_{H,F}$=37.8 Hz, 1F, 5-CF).
Exact mass (ESI⁺): $C_{19}H_{38}FNO_2+H^+$: calcd. 332.2959. found 332.2955. $C_{19}H_{38}FNO_2+Na^+$: calcd. 354.2779. found 354.2776.

9.9 (E)-2-Amino-2-(2-fluorohexadec-2-en-1-yl)propane-1,3-diol (SSS 864)

The mixture of aminodiol 57 and aminoalcohol 58 (30 mg, max. 0.08 mmol) was dissolved in methanol (3 mL), treated with 1 M sodium hydroxide solution (0.12 mL, 0.12 mmol, max. 1.5 eq.) and heated to 100° C. for 7 h in a pressure vessel. After cooling to r.t. the mixture was diluted with 1 M sodium hydroxide solution (5 mL) and the aqueous phase was extracted with dichloromethane (6×10 mL). The combined organic layers were dried over $Na_2SO_4$ and concentrated in vacuo. Purification via column chromatography (silica gel, 20×3 cm, dichloromethane/methanol, 4:1) gave the product as pale yellow solid. Yield: 6 mg (23%).

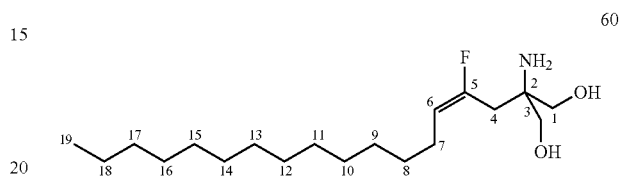

M.p.: 74° C.
¹H-NMR (600 MHz, CDCl₃) δ [ppm]: 0.88 (t, $^3J_{H,H}$=7.0 Hz, 3H, 19-CH₃), 1.24-1.39 (m, 22H, 8-CH₂ to 18-CH₂), 1.96 (q, $^3J_{H,H}$=7.5 Hz, 2H, 7-CH₂), 2.40 (d, $^3J_{H,F}$=26.0 Hz, 2H, 4-CH₂), 3.50 (d, $^2J_{H,H}$=11.1 Hz, 2H, 1-CH₂, 3-CH₂), 3.55 (d, $^2J_{H,H}$=10.9 Hz, 2H, 1-CH₂, 3-CH₂), 5.23 (dt, $^3J_{H,H}$=7.9 Hz, $^3J_{H,F}$=23.4 Hz, 1H, 6-CH).
¹³C-NMR (151 MHz, CDCl₃) δ [ppm]: 14.3 (q, C-19), 22.8 (t, C-18), 25.9 (dt, $^3J_{C,F}$=8.8 Hz, C-7), 29.3, 29.5, 29.6, 29.7, 29.8, 30.0 (t, C-8 to C-16), 32.1 (t, C-17), 33.9 (dt, $^2J_{C,F}$=27.0 Hz, C-4), 56.3 (d, $^3J_{C,F}$=3.8 Hz, C-2), 67.5 (t, C-1, C-3), 110.3 (dd, $^2J_{C,F}$=20.7 Hz, C-6), 156.5 (d, $^1J_{C,F}$=243.7 Hz, C-5).
¹⁹F-NMR (564 MHz, CDCl₃) δ [ppm]: -98.3 (q, $^3J_{H,F}$=25.7 Hz, 1F, 5-CF).
Exact mass (ESI⁺): $C_{19}H_{38}FNO_2+H^+$: calcd. 332.2959. found 332.2959. $C_{19}H_{38}FNO_2+Na^+$: calcd. 354.2779. found 354.2779.

10. Synthesis of the ω-Hydroxy Compound

10.1 2-Amino-2-(hydroxymethyl)octadecane-1,18-diol (SSS 516)

Diester 24 (453 mg, 1.00 mmol) obtained as in example 4.11 was dissolved in THF (13 mL) and treated with lithium chloride (212 mg, 5.00 mmol, 5.0 eq.) and sodium borohydride (189 mg, 5.00 mmol, 5.0 eq.). The mixture was cooled to 0° C. and ethanol (26 mL) was added. After 15 min the mixture was warmed to r.t. and stirred for 2 days. The reaction was quenched with 10% citric acid at 0° C. and adjusted to pH 4. THF was removed under reduced pressure and the residue was extracted with dichloromethane (4×25 mL). The combined organic layers were dried over $Na_2SO_4$ and concentrated in vacuo. The formation of aminodiol 61 was verified by mass spectrometry and the crude product was directly used in the next reaction.

1Protected aminodiol 61 (336 mg, 0.80 mmol) was dissolved in methanol (6.0 mL), treated with 1 M sodium hydroxide solution (1.4 mL, 1.40 mmol, 1.8 eq.) and was heated to reflux for 6 h. After cooling to r.t. overnight the mixture was diluted with 1 M sodium hydroxide solution (10 mL) and the aqueous phase was extracted with dichloromethane (5×10 mL). The combined organic layers were dried over $Na_2SO_4$ and concentrated in vacuo. The product was crystallized from ethyl acetate and isolated as white solid. Yield: 250 mg (75% over two steps).

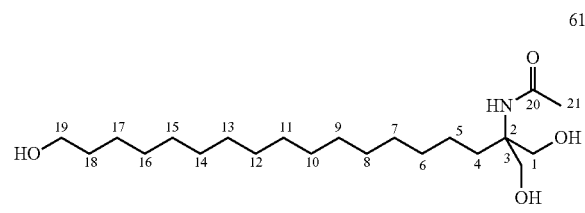 [SMILES: CC(=O)NC(CO)(CO)CCCCCCCCCCCCCCCCO]

Exact Mass (ESI$^+$): $C_{21}H_{43}NO_4$+Na$^+$: calcd. 396.3084. found 396.3091. $(C_{21}H_{43}NO_4)_2$+Na$^+$: calcd. 769.6276. found 769.6268.

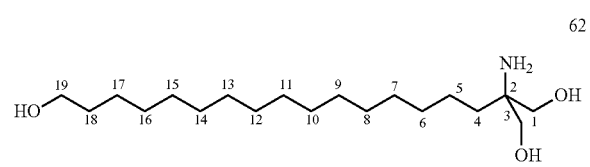 [SMILES: NC(CO)(CO)CCCCCCCCCCCCCCCCO]

M.p.: 103-105° C.

$^1$H-NMR (400 MHz, CD$_3$OD, CDCl$_3$) δ [ppm]: 1.18-1.42 (m, 28H, 4-CH$_2$ to 17-CH$_2$), 1.54 (m, 2H, 18-CH$_2$), 3.32-3.60 (m, 6H, 1-CH$_2$, 3-CH$_2$, 19-CH$_2$).

$^{13}$C-NMR (101 MHz, CD$_3$OD, CDCl$_3$) δ [ppm]: 23.3 (t, C-5), 26.2 (t, C-17), 29.9, 30.0, 30.8 (t, C-6 to C-16), 32.9 (t, C-18), 34.8 (t, C-4), 55.9 (s, C-2), 62.6 (t, C-19), 66.6 (t, C-1, C-3).

Exact Mass (ESI$^+$): $C_{19}H_{41}NO_3$+H$^+$: calcd. 332.3159. found 332.3161. $C_{19}H_{41}NO_3$+Na$^+$: calcd. 354.2979. found 354.2982.

11. Synthesis of the Precursor for Radiochemistry 11.1 Diethyl 2-[(tert-butoxycarbonyl)amino]-2-(16-hydroxyhexadecyl)malonate Diethyl 2-(tert-butoxycarbonyl)amidomalonate 2 (1.18 g, 3.80 mmol, purity: 89% (GC), 1.1 eq.) obtained as in example 1.2, bromide 15 (1.11 g, 3.40 mmol) obtained as in example 4.2 and caesium carbonate (2.35 g, 7.20 mmol, 2.1 eq.) were suspended in acetonitrile (20 mL) and heated to reflux for 6 h. After cooling to r.t. the mixture was adsorbed on silica gel (3 g) and the product was purified by column chromatography (21×3 cm, cyclohexane/ethyl acetate, 4:1→100% ethyl acetate) and isolated as white solid. Yield: 577 mg (33%).

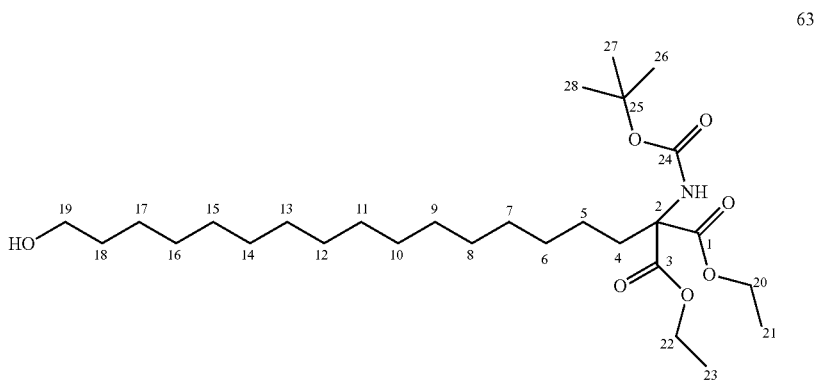 [SMILES: CCOC(=O)C(CCCCCCCCCCCCCCCCO)(NC(=O)OC(C)(C)C)C(=O)OCC]

M.p. 45° C.

$^1$H-NMR (300 MHz, CDCl$_3$) δ [ppm]: 1.22-1.32 (m, 30H, 6-CH$_2$ to 17-CH$_2$, 21-CH$_3$, 23-CH$_3$), 1.43 (s, 9H, 26-CH$_3$, 27-CH$_3$, 28-CH$_3$), 1.49-1.60 (m, 4H, 5-CH$_2$, 18-CH$_2$), 1.95 (br s, 1H, 19-OH), 2.25 (m, 2H, 4-CH$_2$), 3.63 (t, $^3J_{H,H}$=6.7 Hz, 2H, 19-CH$_2$), 4.23 (m, 4H, 20-CH$_2$, 22-CH$_2$), 5.95 (br s, 1H, 2-NH).

$^{13}$C-NMR (75 MHz, CDCl$_3$) δ [ppm]: 14.1 (q, C-21, C-23), 23.3 (t, C-5), 25.8 (t, C-17), 28.3 (q, C-26, C-27, C-28), 29.3, 29.5, 29.7 (t, C-6 to C-16, C-18), 32.8 (t, C-4), 62.3 (t, C-20, C-22), 63.0 (t, C-19), 66.6 (s, C-2), 80.1 (s, C-25), 153.8 (s, C-24), 168.4 (s, C-1, C-3).

Exact Mass (ESI$^+$): $C_{28}H_{53}NO_7$+H$^+$: calcd. 516.3895. found 516.3879. $C_{28}H_{53}NO_7$+Na$^+$: calcd. 538.3714. found 538.3713.

11.2 Diethyl 2-((tert-butoxycarbonyl)amino)-2-(16-(tosyloxy)hexadecyl)malonate Diester 63 (716 mg, 1.39 mmol) was dissolved in dry dichloromethane (30 mL) and treated with triethylamine (0.25 mL, 1.78 mmol, 1.3 eq.). The mixture was cooled to 0° C. and tosyl chloride (270 mg, 1.39 mmol, 1.0 eq.) was added. After 15 min the reaction was warmed to r.t., stirred overnight and then stopped by addition of water (20 mL). The phases were separated and the aqueous phase was extracted with dichloromethane (3×20 mL). The combined organic layers were dried over $MgSO_4$ and concentrated in vacuo. The residue was purified by column chromatography (silica gel, 11×4 cm, cyclohexane/ethyl acetate, 6:1) to give a colourless oil. Yield: 384 mg (41%).

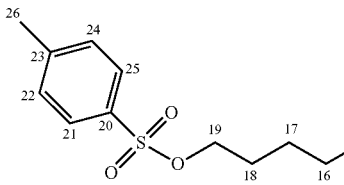
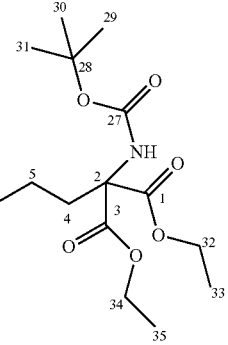

64

$^1$H-NMR (300 MHz, $CDCl_3$) δ [ppm]: 1.10-1.36 and 1.49-1.65 (m, 34H, 5-$CH_2$ to 18-$CH_2$, 33-$CH_3$, 35-$CH_3$), 1.43 (s, 9H, 29-$CH_3$ to 31-$CH_3$), 2.24 (m, 2H, 4-$CH_2$), 2.45 (s, 3H, 26-$CH_3$), 4.02 (t, $^3J_{H,H}$=6.5 Hz, 2H, 19-$CH_2$), 4.23 (m, 4H, 32-$CH_2$, 34-$CH_2$), 5.94 (s, 1H, 2-NH), 7.35 (d, $^3J_{H,H}$=8.0 Hz, 2H, 22-CH/24-CH or 21-CH/25-CH), 7.79 (d, $^3J_{H,H}$=8.3 Hz, 2H, 22-CH/24-CH or 21-CH/25-CH).

$^{13}$C-NMR (75 MHz, $CDCl_3$) δ [ppm]: 14.1 (q, C-33, C-35), 21.7 (q, C-26), 23.4 (t, C-5), 25.8 (t, C-17), 28.3 (q, C-29, C-30, C-31), 28.9, 29.0, 29.4, 29.5, 29.7 (t, C-6 to C-16, C-18), 32.9 (t, C-4), 62.4 (t, C-32, C-34), 66.6 (s, C-2), 70.8 (t, C-19), 80.1 (s, C-28), 128.0, 129.9 (d, C-21, C-22, C-24, C-25), 133.3, 144.7 (s, C-20, C-23), 153.9 (s, C-27), 168.5 (s, C-1, C-3).

Exact Mass (ESI$^+$): $C_{35}H_{59}NO_9S+H^+$: calcd. 670.3983. found 670.3969. $C_{35}H_{59}NO_9S+Na^+$: calcd. 692.3803. found 692.3796.

11.3 17-[(tert-Butoxycarbonyl)amino]-18-hydroxy-17-(hydroxymethyl)octadecyl 4-methylbenzenesulfonate A solution of ester 64 (101 mg, 0.15 mmol) in dry THF (10 mL) was cooled to 0° C. and treated with lithium borohydride (4 M solution in THF, 0.3 mL, 1.20 mmol, 8.0 eq.). After 1 h the mixture was warmed to r.t. and stirred overnight. The mixture was adjusted to pH 3 with 10% citric acid at 0° C. and THF was removed under reduced pressure. The residue was extracted with dichloromethane (4×15 mL) and the combined organic layers were dried over $Na_2SO_4$. The solvent was removed in vacuo and the product, a colourless oil, was used in the next reaction without purification. Yield: 72 mg (82% crude). Side Product 66 was also found.

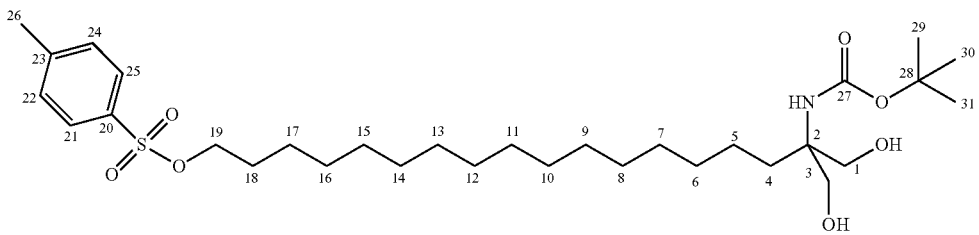

65

$^1$H-NMR (300 MHz, CDCl$_3$) δ [ppm]: 1.17-1.49 (m, 35H, 5-CH$_2$ to 17-CH$_2$, 29-CH$_3$ to 31-CH$_3$), 1.54-1.68 (m, 4H, 4-CH$_2$, 18-CH$_2$), 2.45 (s, 3H, 26-CH$_3$), 3.51-3.80 (m, 4H, 1-CH$_2$, 3-CH$_2$), 4.02 (t, $^3J_{H,H}$=6.5 Hz, 2H, 19-CH$_2$), 7.34 (d, $^3J_{H,H}$=8.0 Hz, 2H, 22-CH/24-CH or 21-CH/25-CH), 7.79 (d, $^3J_{H,H}$=8.2 Hz, 2H, 22-CH/24-CH or 21-CH/25-CH).

$^{13}$C-NMR (75 MHz, CDCl$_3$) δ [ppm]: 21.7 (q, C-26), 25.5 (t, C-5), 28.4, 28.5, 28.6, 29.0, 29.1, 29.5, 29.6, 29.8 (t, C-6 to C-18; q, C-29 to C-31), 32.1 (t, C-4), 62.4 (s, C-2), 66.7 (t, C-1, C-3), 70.8 (t, C-19), 93.0 (s, C-28), 128.0, 129.9 (d, C-21, C-22, C-24, C-25), 133.5, 144.7 (s, C-20, C-23).

Exact Mass (ESI$^+$): C$_{31}$H$_{55}$NO$_7$S+Na$^+$: calcd. 608.3591. found 608.3618.

Side product 66:

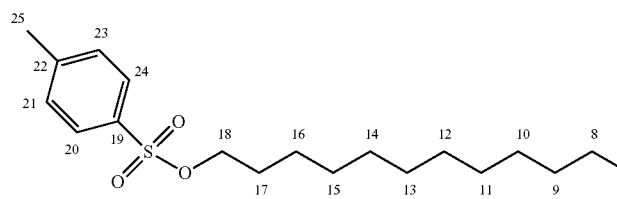

66

Exact Mass (ESI$^+$): C$_{30}$H$_{53}$NO$_6$S+Na$^+$: calcd. 578.3486. found 578.3515.

11.4 17-Amino-18-hydroxy-17-(hydroxymethyl)octadecyl 4-methylbenzenesulfonate (SSS 659)

Tosylate 65 (72 mg, max. 0.12 mmol) was dissolved in ethyl acetate (1.5 mL), treated with 2 M hydrochloric acid (1 mL) and stirred at r.t. for 5 days. The reaction was stopped by addition of water (15 mL) and the aqueous phase was extracted with dichloromethane (3×10 mL). The combined organic layers were dried over Na$_2$SO$_4$ and concentrated in vacuo. The product was crystallized from ethyl acetate to give a waxy, white solid. Yield: 21 mg (36%).

M.p.: 96-98° C.

$^1$H-NMR (300 MHz, CD$_3$OD, CDCl$_3$) δ [ppm]: 1.21-1.37 (m, 28H, 4-CH$_2$ to 17-CH$_2$), 1.65 (m, 2H, 18-CH$_2$), 2.48 (s, 3H, 26-CH$_3$), 3.61 (d, $^2J_{H,H}$=11.6 Hz, 2H, 1-CH$_2$, 3-CH$_2$), 3.65 (d, $^2J_{H,H}$=11.7 Hz, 2H, 1-CH$_2$, 3-CH$_2$), 4.03 (t, $^3J_{H,H}$=6.4 Hz, 2H, 19-CH$_2$), 7.41 (d, $^3J_{H,H}$=8.1 Hz, 2H, 22-CH/24-CH or 21-CH/25-CH), 7.79 (d, $^3J_{H,H}$=8.3 Hz, 2H, 22-CH/24-CH or 21-CH/25-CH).

$^{13}$C-NMR (75 MHz, CD$_3$OD, CDCl$_3$) δ [ppm]: 21.8 (q, C-26), 23.3 (t, C-5), 25.8 (t, C-17), 29.3, 29.4, 29.9, 30.0, 30.2, 30.6 (t, C-6 to C-16, C-18), 31.9 (t, C-4), 61.4 (s, C-2), 62.1 (t, C-1, C-3), 71.6 (t, C-19), 128.4, 130.5 (d, C-21, C-22, C-24, C-25), 133.5, 145.7 (s, C-20, C-23).

Exact Mass (ESI$^+$): C$_{35}$H$_{59}$NO$_9$S+H$^+$: calcd. 670.3983. found 670.3969.

12. Synthesis of FTY 720

12.1 2-Bromo-1-(4-octylphenyl)-1-ethanone

Aluminium chloride (4.80 g, 32.0 mmol, 1.0 eq.) and 1-phenyloctane (6.84 g, 32.0 mmol) were dissolved in dry dichloromethane (10 mL) and cooled to −10° C. A solution of bromoacetyl bromide (3.14 mL, 32.0 mmol, 1.0 eq.) in dichloromethane (12 mL) was added dropwise and the mixture was allowed to return to r.t. while stirring overnight. The mixture was slowly poured into ice water (100 mL) and the aqueous phase was extracted with dichloromethane (3×50 mL). The combined organic layers were dried over MgSO$_4$ and concentrated under reduced pressure. The product was obtained as brown, highly viscous oil and was used in the next reaction without purification. Yield: 8.90 g (62%), purity: 69% (GC).

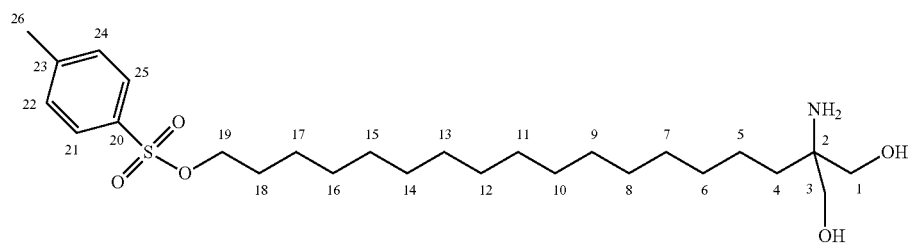

67

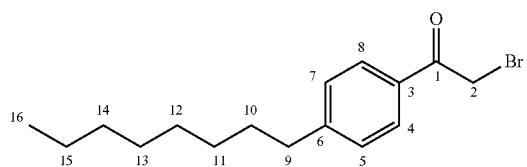

68

¹H-NMR (300 MHz, CDCl₃) δ [ppm]: 0.88 (m, 3H, 16-CH₃), 1.22-1.35 (m, 10H, 11-CH₂ to 15-CH₂), 1.63 (m, 2H, 10-CH₂), 2.67 (m, 2H, 9-CH₂), 4.44 (s, 2H, 2-CH₂), 7.29 (m, 2H, 4-CH, 8-CH), 7.90 (m, 2H, 5-CH, 7-CH).

¹³C-NMR (75 MHz, CDCl₃) δ [ppm]: 14.2 (q, C-16), 22.8 (t, C-15), 29.3, 29.4, 29.5, 31.1, 31.2 (t, C-10 to C-14), 32.0 (t, C-2), 36.2 (t, C-9), 129.0, 129.2 (d, C-4, C-5, C-7, C-8), 131.7, 150.1 (s, C-3, C-6), 191.1 (s, C-1).

Ref.: Synthesis according to P. Durand, P. Peralba, F. Sierra, P. Renaut, *Synthesis* 2000, 4, 505-506.

Spectroscopic data agree with those given in the literature.

12.2 Diethyl 2-acetamido-2-(2-(4-octylphenyl)-2-oxoethyl)malonate

Bromo derivative 68 (8.90 g, 19.7 mmol, purity: 69% (GC), 1.3 eq.), diethyl 2-acetamidomalonate 1 (3.21 g, 14.8 mmol), obtained as in example 1.1, and caesium carbonate (5.15 g, 15.8 mmol, 1.1 eq) were suspended in acetonitrile (125 mL) and heated to reflux for 4 h. After cooling to r.t. the mixture was adsorbed on silica gel (15 g) and purified by column chromatography (10.5×8 cm, cyclohexane/ethyl acetate, 4:1→2:1). The product was isolated as pale yellow oil. Yield: 5.87 g (94%).

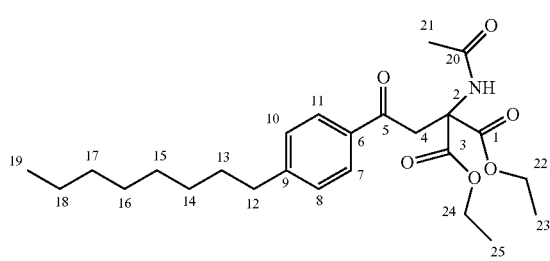

69

¹H-NMR (400 MHz, CDCl₃) δ [ppm]: 0.87 (t, ³J$_{H,H}$=6.7 Hz, 3H, 19-CH₃), 1.24 (t, ³J$_{H,H}$=7.1 Hz, 6H, 23-CH₃, 25-CH₃), 1.26-1.33 (m, 10H, 14-CH₂ to 18-CH₂), 1.61 (m, 2H, 13-CH₂), 1.97 (s, 3H, 21-CH₃), 2.66 (m, 2H, 12-CH₂), 4.25 (s, 2H, 4-CH₂), 4.27 (2 q, ³J$_{H,H}$=7.1 Hz, 4H, 22-CH₂, 24-CH₂), 7.15 (s, 1H, 2-NH), 7.26, 7.88 (m, 2H, 7-CH, 11-CH or 8-CH, 10-CH), 7.88 (m, 2H, 7-CH, 11-CH or 8-CH, 10-CH).

¹³C-NMR (101 MHz, CDCl₃) δ [ppm]: 13.9 (q, C-23, C-25), 14.1 (q, C-19), 22.7 (t, C-18), 22.9 (q, C-21), 29.2, 29.4, 31.1 (t, C-13 to C-16), 31.9 (t, C-17), 36.0 (t, C-12), 42.2 (t, C-4), 62.8 (t, C-22, C-24), 64.0 (s, C-2), 128.4, 128.7 (d, C-7, C-8, C-10, C-11), 133.8, 149.6 (s, C-9, C-6), 167.4 (s, C-1, C-3), 169.4 (s, C-20), 196.5 (s, C-5).

Exact mass (ESI⁺): C₂₅H₃₇NO₆+H⁺: calcd. 448.2694. found 448.2689. C₂₅H₃₇NO₆+Na⁺: calcd. 470.2513. found 470.2505. (C₂₅H₃₇NO₆)₂+Na⁺: calcd. 917.5134. found 917.5132.

12.3 Diethyl 2-acetamido-2-(4-octylphenethyl)malonate

To a solution of triethyl silane (3.0 mL, 27.1 mmol, 5.4 eq.) in dry dichloromethane (25 mL) a solution of ketone 69 (2.24 g, 5.0 mmol) in dry dichloromethane (6 mL) was added dropwise, followed by the addition of titanium tetrachloride (2.0 mL, 19.1 mmol, 2.6 eq.). The reaction mixture was stirred at r.t. overnight and was then slowly poured into ice water (150 mL). After phase separation the aqueous layer was extracted with dichloromethane (2×70 mL). The organic phases were collected, dried over MgSO₄ and concentrated in vacuo. The residue was purified by column chromatography (silica gel, 14×4 cm, cyclohexane/ethyl acetate, 4:1) and the product was obtained as white solid. Yield: 1.87 g (86%).

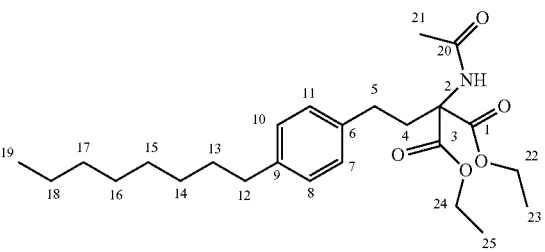

70

M.p.: 55-57° C.

¹H-NMR (300 MHz, CDCl₃) δ [ppm]: 0.86 (m, 3H, 19-CH₃), 1.24 (t, ³J$_{H,H}$=7.1 Hz, 6H, 23-CH₃, 25-CH₃), 1.23-1.33 (m, 10H, 14-CH₂ to 18-CH₂), 1.56 (m, 2H, 13-CH₂), 1.97 (s, 3H, 21-CH₃), 2.45 (m, 2H, 4-CH₂), 2.55 (m, 2H, 12-CH₂), 2.68 (m, 2H, 5-CH₂), 4.19 (m, 4H, 22-CH₂, 24-CH₂), 6.79 (s, 1H, 2-NH), 7.06 (m, 4H, 7-CH, 8-CH, 10-CH, 11-CH).

¹³C-NMR (75 MHz, CDCl₃) δ [ppm]: 14.0 (q, C-23, C-25), 14.1 (q, C-19), 22.t (t, C-18), 23.0 (q, C-21), 29.3, 29.5, 29.7, 29.8, 31.6, 31.9 (t, C-4, C-5, C-13 to C-16), 33.4 (t, C-17), 35.5 (t, C-12), 62.5 (t, C-22, C-24), 66.4 (s, C-2), 128.3, 128.4 (d, C-7, C-8, C-10, C-11), 137.7, 140.7 (s, C-6, C-9), 168.1 (s, C-1, C-3), 169.0 (s, C-20).

Exact mass (ESI⁺): C₂₅H₃₉NO₅+H⁺: calcd. 434.2901. found 434.2904. C₂₅H₃₉NO₅+Na⁺: calcd. 456.2720. found 456.2725. (C₂₅H₃₉NO₅)₂+Na⁺: calcd. 889.5549. found 889.5541.

Ref.: Reaction procedure taken from P. Durand, P. Peralba, F. Sierra, P. Renaut, *Synthesis* 2000, 4, 505-506.

Spectroscopic data agree with those given in the literature.

12.4 N-(1-Hydroxy-2-(hydroxymethyl)-4-(4-octylphenyl)butan-2-yl)acetamide

To a solution of diester 70 (1.27 g, 2.93 mmol) in THF (30 mL) lithium chloride (636 mg, 15.0 mmol, 5.1 eq.) and sodium borohydride (567 mg, 15.0 mmol, 5.1 eq.) were added. The mixture was cooled to 0° C. and treated with ethanol (60 mL). After 30 min at 0° C. the mixture was allowed to warm up to r.t. and was stirred for 3 days. The mixture was adjusted to pH 4 with 10% citric acid at 0° C. THF was removed in vacuo and the residue was extracted with dichloromethane (4×30 mL). The combined organic phases were washed with brine (1×80 mL), dried over Na₂SO₄ and concentrated under reduced pressure. The product was purified by column chromatography (silica gel, 10×4 cm, cyclohexane/ethyl acetate, 1:2) and was obtained as a white solid. Yield: 974 mg (95%).

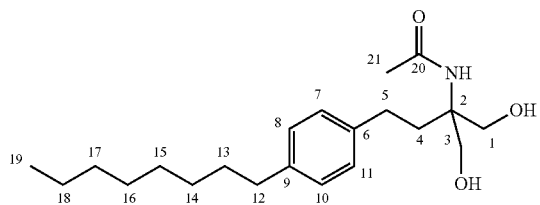

71

M.p.: 87-88° C.

$^1$H-NMR (400 MHz, CDCl$_3$) δ [ppm]: 0.87 (m, 3H, 19-CH$_3$), 1.20-1.33 (m, 10H, 14-CH$_2$ to 18-CH$_2$), 1.56 (m, 2H, 13-CH$_2$), 1.93 (s, 3H, 21-CH$_3$), 1.96 (m, 2H, 4-CH$_2$), 2.52-2.60 (m, 4H, 5-CH$_2$, 12-CH$_2$), 3.61 (d, $^2J_{H,H}$=11.5 Hz, 2H, 1-CH$_2$, 3-CH$_2$), 3.80 (d, $^2J_{H,H}$=11.5 Hz, 2H, 1-CH$_2$, 3-CH$_2$), 4.61 (br s, 2H, 1-OH, 3-OH), 6.23 (s, 1H, 2-NH), 7.09 (m, 4H, 7-CH, 8-CH, 10-CH, 11-CH).

$^{13}$C-NMR (101 MHz, CDCl$_3$) δ [ppm]: 14.1 (q, C-19), 22.7 (t, C-18), 23.9 (q, C-21), 29.2, 29.3, 29.4, 29.5, 31.6, 31.9 (t, C-4, C-5, C-13 to C-16), 34.3 (t, C-17), 35.5 (t, C-12), 61.4 (s, C-2), 65.5 (t, C-1, C-3), 128.2, 128.6 (d, C-7, C-8, C-10, C-11), 138.7, 140.7 (s, C-6, C-9), 172.0 (s, C-20).

Exact mass (ESI$^+$): C$_{21}$H$_{35}$NO$_3$+H$^+$: calcd. 350.2690. found 350.2693. C$_{21}$H$_{35}$NO$_3$+Na$^+$: calcd. 372.2509. found 372.2512. (C$_{21}$H$_{35}$NO$_3$)$_2$+Na$^+$: calcd. 721.5126. found 721.5127.

12.5 2-Amino-2-(4-octylphenethyl)propane-1,3-diol (FTY 720) (SSS 798)

Protected aminodiol 71 (349 mg, 1.0 mmol) was dissolved in methanol (20 mL) and treated with 1 M sodium hydroxide solution (1.2 mL, 1.2 mmol, 1.2 eq.). The reaction mixture was heated to reflux for 5 h. After cooling to r.t. the mixture was diluted with 1 M sodium hydroxide solution (15 mL) and the aqueous phase was extracted with dichloromethane (5×20 mL). The combined organic layers were dried over Na$_2$SO$_4$ and concentrated in vacuo. The product was crystallized from ethyl acetate to give a white solid. Yield: 252 mg (82%).

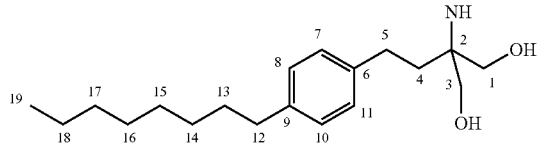

72

M.p.: 127° C. (lit. 121-124° C.)

$^1$H-NMR (300 MHz, CD$_3$OD, CDCl$_3$) δ [ppm]: 0.87 (m, 3H, 19-CH$_3$), 1.22-1.37 (m, 10H, 14-CH$_2$ to 18-CH$_2$), 1.57 (m, 2H, 13-CH$_2$), 1.69 (m, 2H, 4-CH$_2$), 2.51-2.65 (m, 4H, 5-CH$_2$, 12-CH$_2$), 3.48 (d, $^2J_{H,H}$=10.9 Hz, 2H, 1-CH$_2$, 3-CH$_2$), 3.54 (d, $^2J_{H,H}$=11.0 Hz, 2H, 1-CH$_2$, 3-CH$_2$), 7.09 (m, 4H, 7-CH, 8-CH, 10-CH, 11-CH).

$^{13}$C-NMR (75 MHz, CD$_3$OD, CDCl$_3$) δ [ppm]: 14.3 (q, C-19), 23.2 (t, C-18), 29.5, 29.9, 30.1 (t, C-13 to C-16), 32.2 (t, C-5), 32.5 (t, C-4), 36.1 (t, C-17), 37.0 (t, C-12), 56.4 (s, C-2), 66.2 (t, C-1, C-3), 128.7, 129.0 (d, C-7, C-8, C-10, C-11), 140.1, 140.9 (s, C-6, C-9).

Exact mass (ESI$^+$): C$_{19}$H$_{33}$NO$_2$+H$^+$: calcd. 308.2584. found 308.2585. C$_{19}$H$_{33}$NO$_2$+Na$^+$: calcd. 330.2404. found 330.2408. (C$_{19}$H$_{33}$NO$_2$)$_2$+Na$^+$: calcd. 637.4915. found 637.4917.

Ref.: Spectroscopic data agree with those given in S. Kim, H. Lee, M. Lee, T. Lee, *Synthesis* 2006, 5, 753-755.

13. Synthesis of the 2-Fluoromethyl Compound

2-Amino-2-(fluoromethyl)-4-(4-octylphenyl)butan-1-ol (SSS 461)

FTY 720 (310 mg, 1.00 mmol) was suspended in dry dichloromethane (10 mL) and cooled down to −78° C. Diethylaminosulfur trifluoride (DAST, 0.13 mL, 1.00 mmol, 1.0 eq.) was slowly added to this suspension and the mixture was allowed to warm up to r.t. overnight. The reaction was neutralized with saturated sodium bicarbonate solution (30 mL) at −10° C. The phases were separated and the aqueous phase was extracted with dichloromethane (3×20 mL). The combined organic layers were dried over MgSO$_4$ and the solvent was removed under reduced pressure. The residue was purified by column chromatography (silica gel, 20×3 cm, dichloromethane/methanol, 4:1) and subsequently by gradient HPLC (RP-HPLC Nucleodur 100-10 C$_{18ec}$ column (250× 16 mm), acetonitrile/water (0.1% TFA)) with a Knauer HPLC system. The obtained TFA salt was dissolved in methanol (1 mL) and 1 M sodium hydroxide solution (3 mL) and the mixture was extracted with dichloromethane (5×5 mL). The organic phases were dried over Na$_2$SO$_4$ and concentrated. The product was dried in high vacuum and obtained as highly viscous oil. Yield: 5 mg (2%).

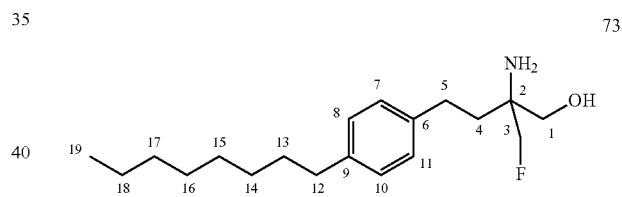

73

$^1$H-NMR (300 MHz, CDCl$_3$) δ [ppm]: 0.87 (t, $^3J_{H,H}$=6.7 Hz, 3H, 19-CH$_3$), 1.16-1.37 (m, 10H, 14-CH$_2$ to 18-CH$_2$), 1.56 (m, 2H, 13-CH$_2$), 1.81 (m, 2H, 4-CH$_2$), 2.47-2.68 (m, 4H, 5-CH$_2$, 12-CH$_2$), 3.52 (m, 2H, 1-CH$_2$), 4.38 (d, $^2J_{H,F}$=47.3 Hz, 2H, 3-CH$_2$), 7.01-7.11 (m, 4H, 7-CH, 8-CH, 10-CH, 11-CH).

$^{13}$C-NMR (75 MHz, CDCl$_3$) δ [ppm]: 14.2 (q, C-19), 23.5 (t, C-18), 29.3, 29.4, 29.5, 29.6, 31.7, 32.0, 34.8 (t, C-4, C-5, C-13 to C-17), 35.7 (t, C-12), 56.1 (d, $^2J_{C,F}$=17.2 Hz, C-2), 65.2 (dt, $^3J_{C,F}$=4.1 Hz, C-1), 86.1 (dt, $^1J_{C,F}$=173.3 Hz, C-3), 128.2, 128.7 (d, C-7, C-8, C-10, C-11), 138.7, 140.9 (s, C-6, C-9).

$^{19}$F-NMR (282 MHz, CDCl$_3$) δ [ppm]: −230.3 (t, $^2J_{H,F}$=47.3 Hz, 1F, 3-CH$_2$F).

Exact mass (ESI$^+$): C$_{19}$H$_{32}$FNO+H$^+$: calcd. 310.2541. found 310.2542. C$_{19}$H$_{32}$FNO+Na$^+$: calcd. 332.2360. found 332.2379.

14. Synthesis of the 4-hydroxy FTY 720 analogues

14.1 N-[1,4-Dihydroxy-2-(hydroxymethyl)-4-(4-octylphenyl)butan-2-yl]acetamide Lithium chloride (424 mg, 10.0 mmol, 5.0 eq.) and sodium borohydride (378 mg, 10.0 mmol, 5.0 eq.) were added to a solution of diester 69 (930 mg, 2.08 mmol), obtained as for example 12.2, in THF (8 mL). The mixture was cooled to 0° C. and treated with ethanol (16 mL). After 45 min the reaction was warmed to r.t. and stirred overnight. The mixture was adjusted to pH 4 with 10% citric acid at 0° C. and THF was removed in vacuo. The residue was extracted with dichloromethane (4×10 mL). The organic layers were washed with brine (1×15 mL), dried over $Na_2SO_4$ and evaporated. The product was purified by column chromatography (silica gel, 20×3 cm, dichloromethane/methanol, 20:1) and isolated as white solid. Yield: 586 mg (77%).

74

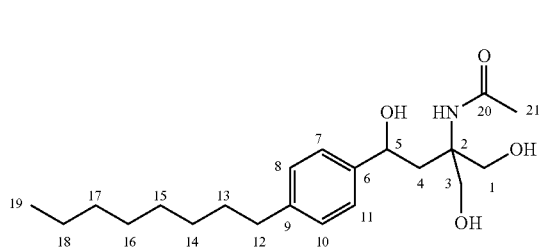

M.p.: 123° C.

$^1$H-NMR (300 MHz, $CDCl_3$) δ [ppm]: 0.87 (m, 3H, 19-$CH_3$), 1.21-1.36 (m, 10H, 14-$CH_2$ to 18-$CH_2$), 1.59 (m, 2H, 13-$CH_2$), 2.00 (s, 3H, 21-$CH_3$), 2.00 (m, 2H, 4-$CH_2$), 2.58 (m, 2H, 12-$CH_2$), 3.59-3.91 (m, 4H, 1-$CH_2$, 3-$CH_2$), 4.85 (m, 1H, 5-CH), 7.13 (d, $^3J_{H,H}$=8.1 Hz, 2H, 7-CH/11-CH or 8-CH/10-CH), 7.26 (d, $^3J_{H,H}$=8.1 Hz, 2H, 7-CH/11-CH or 8-CH/10-CH).

$^{13}$C-NMR (101 MHz, $CD_3OD$, $CDCl_3$) δ [ppm]: 13.7 (q, C-19), 22.4 (t, C-18), 23.0 (q, C-21), 29.0, 29.2, 31.3, 31.6 (t, C-13 to C-17), 35.3 (t, C-12), 41.2 (t, C-4), 61.1 (s, C-2), 63.7, 65.0 (t, C-1, C-3), 69.7 (d, C-5), 125.2, 128.1 (d, C-7, C-8, C-10, C-11), 141.8, 141.9 (s, C-6, C-9), 172.3 (s, C-20).

Exact mass (ESI$^+$): $C_{21}H_{35}NO_4$+Na$^+$: calcd. 388.2458. found 388.2463. $(C_{21}H_{35}NO_4)_2$+Na$^+$: calcd. 753.5024. found 753.5032.

14.2 3-Amino-3-(hydroxymethyl)-1-(4-octylphenyl)butane-1,4-diol (SSS 563)

Protected triol 74 (1.37 g, 2.00 mmol) was dissolved in methanol (30 mL) and treated with 1 M sodium hydroxide solution (2.4 mL, 2.40 mmol, 1.2 eq.). The reaction mixture was heated to reflux for 6 h and was then diluted with 1 M sodium hydroxide solution (20 mL) after cooling to r.t. The aqueous phase was extracted with dichloromethane (4×30 mL) and the organic layers were dried over $Na_2SO_4$. The solvent was evaporated and the product was purified by column chromatography (silica gel, dichloromethane/methanol, 4:1) to yield a waxy, white solid. Yield: 503 mg (78%).

75

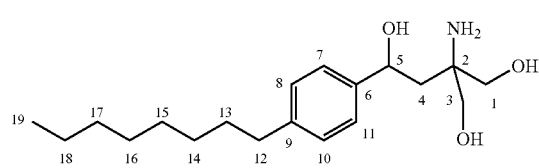

M.p.: 74-76° C.

$^1$H-NMR (400 MHz, $CDCl_3$) δ [ppm]: 0.87 (t, $^3J_{H,H}$=6.7 Hz, 3H, 19-$CH_3$), 1.16-1.34 (m, 10H, 14-$CH_2$ to 18-$CH_2$), 1.47-1.70 (m, 4H, 4-$CH_2$, 13-$CH_2$), 2.50 (m, 2H, 12-$CH_2$), 3.28-3.58 (m, 4H, 1-$CH_2$, 3-$CH_2$), 4.03 (br s, 5H, 1-OH, 3-OH, 5-OH, 2-$NH_2$), 4.83 (d, $^3J_{H,H}$=10.3 Hz, 1H, 5-CH), 7.04 (d, $^3J_{H,H}$=7.7 Hz, 2H, 7-CH/11-CH or 8-CH/10-CH), 7.15 (d, $^3J_{H,H}$=7.8 Hz, 2H, 7-CH/11-CH or 8-CH/10-CH).

$^{13}$C-NMR (101 MHz, $CDCl_3$) δ [ppm]: 14.2 (q, C-19), 22.8 (t, C-18), 29.5, 29.6, 31.7, 32.0 (t, C-13 to C-17), 35.8 (t, C-12), 43.8 (t, C-4), 56.5 (s, C-2), 65.8, 67.2 (t, C-1, C-3), 70.4 (d, C-5), 125.6, 128.5 (d, C-7, C-8, C-10, C-11), 142.1, 142.3 (s, C-6, C-9).

Exact mass (ESI$^+$): $C_{19}H_{33}NO_3$+H$^+$: calcd. 324.2533. found 324.2550. $C_{19}H_{33}NO_3$+Na$^+$: calcd. 346.2353. found 346.2355.

15. Synthesis of the ω-Fluoro Substituted FTY 720 Analogues

15.1 2-Bromo-1-[4-(8-hydroxyoctyl)phenyl]ethanone

Aluminium chloride (200 mg, 1.50 mmol, 3.0 eq.) was suspended in dry dichloromethane (8 mL) and cooled to 0° C. 8-phenyl-1-octanol (0.11 mL, 0.50 mmol) and bromo acetylbromide (53 μL, 0.60 mmol, 1.2 eq.) were added dropwise. After 20 min the mixture was warmed to r.t. and stirred overnight. The reaction was stopped by pouring the solution into a mixture of ice water (25 mL) and concentrated hydrochloric acid (10 mL). The phases were separated and the aqueous layer was extracted with dichloromethane (2×10 mL). The combined organic phases were washed with saturated sodium bicarbonate solution (1×10 mL) and brine (1×10 mL) and dried over $MgSO_4$. The solvent was evaporated and the residue was purified by column chromatography (silica gel, 12×4 cm, cyclohexane/ethyl acetate, 8:1). The product was isolated as colourless oil. Yield: 120 mg (73%).

76

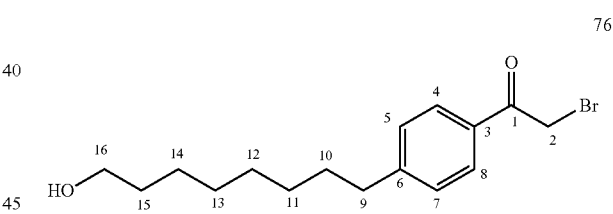

$^1$H-NMR (300 MHz, $CDCl_3$) δ [ppm]: 1.29-1.39 (m, 8H, 11-$CH_2$ bis 14-$CH_2$), 1.50-1.66 (m, 4H, 10-$CH_2$, 15-$CH_2$), 2.67 (t, $^3J_{H,H}$=7.7 Hz, 2H, 9-$CH_2$), 3.63 (t, $^3J_{H,H}$=6.6 Hz, 2H, 16-$CH_2$), 4.45 (s, 2H, 2-$CH_2$), 7.29 (d, $^3J_{H,H}$=8.4 Hz, 2H, 4-CH/8-CH or 5-CH/7-CH), 7.90 (d, $^3J_{H,H}$=8.3 Hz, 2H, 4-CH/8-CH or 5-CH/7-CH).

$^{13}$C-NMR (75 MHz, $CDCl_3$) δ [ppm]: 25.8 (t, C-14), 29.2, 29.4, 29.5 (t, C-11 bis C-13), 31.1, 31.2 (t, C-10, C-15), 32.8 (t, C-2), 36.1 (t, C-9), 63.0 (t, C-16), 129.0, 129.2 (d, C-4, C-5, C-7, C-8), 131.7, 150.0 (s, C-3, C-6), 191.1 (s, C-1).

Exact mass (ESI$^+$): $C_{16}H_{23}BrO_2$+Na$^+$: calcd. 349.0774. found 349.0775. $(C_{16}H_{23}BrO_2)_2$+Na$^+$: calcd. 677.1637. found 677.1624.

15.2 Diethyl 2-acetamido-2-(2-(4-(8-hydroxyoctyl)phenyl)-2-oxoethyl)malonate Bromide 76 (327 mg, 1.0 mmol), diethyl 2-acetamidomalonate 1 (217 mg, 1.0 mmol), obtained as for example 1.1, and caesium carbonate (350 mg, 1.08 mmol, 1.0 eq.) were suspended in acetonitrile (15 mL) and heated to reflux for 5 h. After cooling to r.t the precipitate was filtered and the solvent was removed. The residue was purified by column chromatography (silica gel, cyclohexane/ethyl acetate, 1:2) and the product was obtained as a colourless oil. Yield: 221 mg (48%).

77

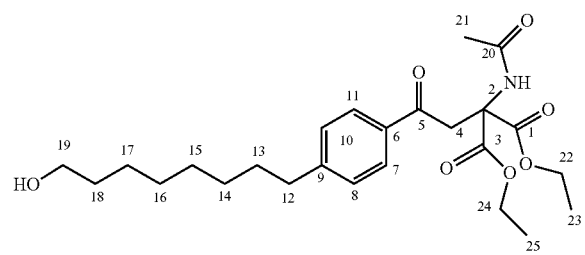

$^1$H-NMR (300 MHz, CDCl$_3$) δ [ppm]: 1.24 (t, $^3J_{H,H}$=7.1 Hz, 6H, 23-CH$_3$, 25-CH$_3$), 1.28-1.36 (m, 8H, 14-CH$_2$ to 17-CH$_2$), 1.51-1.67 (m, 4H, CH$_2$, 13-CH$_2$, 18-CH$_2$), 1.97 (s, 3H, 21-CH$_3$), 2.65 (t, $^3J_{H,H}$=7.7 Hz, 2H, 12-CH$_2$), 3.63 (t, $^3J_{H,H}$=6.6 Hz, 2H, 19-CH$_2$), 4.22-4.32 (m, 6H, 4-CH$_2$, 22-CH$_2$, 24-CH$_2$), 7.15 (s, 1H, 2-NH), 7.26 (d, $^3J_{H,H}$=8.5 Hz, 2H, 7-CH, 11-CH or 8-CH, 10-CH), 7.88 (d, $^3J_{H,H}$=8.3 Hz, 2H, 7-CH, 11-CH or 8-CH, 10-CH).

$^{13}$C-NMR (75 MHz, CDCl$_3$) δ [ppm]: 14.0 (q, C-23, C-25), 23.1 (q, C-21), 25.8 (t, C-17), 29.2, 29.4, 29.5, 31.1 (t, C-13 to C-16), 32.8 (t, C-18), 36.1 (t, C-12), 42.3 (t, C-4), 63.0, 63.1 (t, C-19, C-22, C-24), 64.1 (s, C-2), 128.5, 128.8 (d, C-7, C-8, C-10, C-11), 133.9, 149.7 (s, C-6, C-9), 167.4 (s, C-1, C-3), 169.6 (s, C-20), 196.6 (s, C-5).

Exact mass (ESI$^+$): C$_{25}$H$_{37}$NO$_7$+H$^+$: calcd. 464.2643. found 464.2639. C$_{25}$H$_{37}$NO$_7$+Na$^+$: calcd. 486.2462. found 486.2447.

15.3 Diethyl 2-acetamido-2-{2-[4-(8-fluorooctyl)phenyl]-2-oxoethyl}malonate

Ketone 77 (166 mg, 0.35 mmol) was dissolved in dry THF (3 mL) in a PTFE-vessel. Perfluoro-1-butanesulfonyl fluoride (PBSF, 0.19 mL, 1.06 mmol, 3.0 eq.), triethyl amine trishydrofluoride (0.18 mL, 1.10 mmol, 3.1 eq.) and diisopropyl ethyl amine (0.56 mL, 3.24 mmol, 9.0 eq.) were added and the mixture was stirred at r.t. for 2 days. The reaction was stopped by addition of saturated sodium bicarbonate solution (5 mL) and the aqueous phase was extracted with dichloromethane (3×15 mL). The combined organic layers were dried over MgSO$_4$ and concentrated under reduced pressure. The residue was purified by column chromatography (silica gel, cyclohexane/ethyl acetate, 2:1) and the product was isolated as colourless oil. Yield: 132 mg (80%).

78

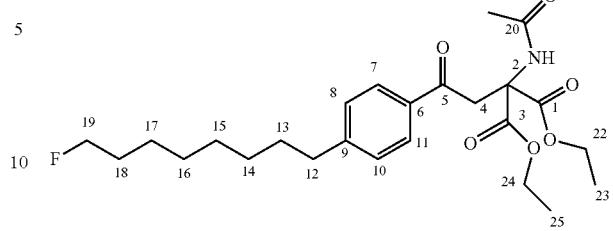

$^1$H-NMR (300 MHz, CDCl$_3$) δ [ppm]: 1.25 (t, $^3J_{H,H}$=7.1 Hz, 6H, 23-CH$_3$, 25-CH$_3$), 1.30-1.41 (m, 8H, 14-CH$_2$ bis 17-CH$_2$), 1.59-1.79 (m, 4H, 13-CH$_2$, 18-CH$_2$), 1.98 (s, 3H, 21-CH$_3$), 2.66 (t, $^3J_{H,H}$=7.7 Hz, 2H, 12-CH$_2$), 4.25 (s, 2H, 4-CH$_2$), 4.27 (q, $^3J_{H,H}$=7.2 Hz, 4H, 22-CH$_2$, 24-CH$_2$), 4.43 (dt, $^3J_{H,H}$=6.1 Hz, $^2J_{H,F}$=47.4 Hz, 2H, 19-CH$_2$), 7.13 (br s, 1H, 2-NH), 7.27 (d, $^3J_{H,H}$=8.2 Hz, 2H, 7-CH, 11-CH or 8-CH, 10-CH), 7.88 (d, $^3J_{H,H}$=8.3 Hz, 2H, 7-CH, 11-CH or 8-CH, 10-CH).

$^{13}$C-NMR (75 MHz, CDCl$_3$) δ [ppm]: 14.0 (q, C-23, C-25), 23.1 (q, C-21), 25.3 (dt, $^3J_{C,F}$=5.5 Hz, C-17), 29.2, 29.4 (t, C-14 bis C-16), 30.5 (dt, $^2J_{C,F}$=19.4 Hz, C-18), 31.2 (t, C-13), 36.1 (t, C-12), 42.3 (t, C-4), 63.0 (t, C-22, C-24), 64.1 (s, C-2), 84.3 (dt, $^1J_{C,F}$=164.1 Hz, C-19), 128.5, 128.9 (d, C-7, C-8, C-10, C-11), 133.9, 149.6 (s, C-6, C-9), 167.5 (s, C-1, C-3), 169.6 (s, C-20), 196.6 (s, C-5).

$^{19}$F-NMR (282 MHz, CDCl$_3$) δ [ppm]: −218.6 (tt, $^3J_{H,F}$=25.0 Hz, $^2J_{H,F}$=47.4 Hz, 1F, 19-CH$_2$F).

Exact mass (ESI$^+$): C$_{25}$H$_{36}$FNO$_6$+H$^+$: calcd. 466.2599. found 466.2605. C$_{25}$H$_{36}$FNO$_6$+Na$^+$: calcd. 488.2419. found 488.2422.

Ref.: Synthesis in analogy to J. Yin, D. S. Zarkowsky, D. W. Thomas, M. M. Zhao, M. A. Huffman, *Org. Lett.* 2004, 6, 1465-1468.

15.4 Diethyl 2-acetamido-2-[4-(8-fluorooctyl)phenethyl]malonate

A solution of ketone 78 (63 mg, 136 µmol) in Ethanol (4 mL) was treated with triethyl silane (89 µL, 544 µmol, 4.0 eq.) and a catalytic amount of palladium chloride under an argon atmosphere. The reaction mixture was stirred at r.t. overnight and was subsequently heated to 98° C. for 3 h until completion of the reaction. After cooling to r.t. water (3 mL) was added and the mixture was extracted with dichloromethane (5×6 mL). The organic layers were dried over Na$_2$SO$_4$ and concentrated in vacuo. The residue was purified by column chromatography (silica gel, 16×3 cm, cyclohexane/ethyl acetate, 2:1) and the product was isolated as colourless oil. Yield: 35 mg (57%).

79

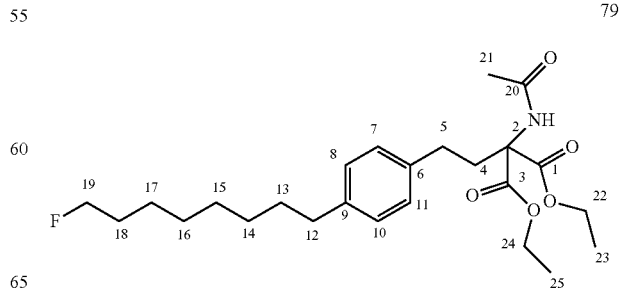

$^1$H-NMR (300 MHz, CDCl$_3$) δ [ppm]: 1.24 (t, $^3J_{H,H}$=7.1 Hz, 6H, 23-CH$_3$, 25-CH$_2$), 1.29-1.35 (m, 8H, 14-CH$_2$ to 17-CH$_2$), 1.51-1.75 (m, 4H, 13-CH$_2$, 18-CH$_2$), 1.98 (s, 3H, 21-CH$_3$), 2.41-2.72 (m, 4H, 4-CH$_2$, 5-CH$_2$), 2.55 (m, 2H, 12-CH$_2$), 4.20 (m, 4H, 22-CH$_2$, 24-CH$_2$), 4.43 (dt, $^3J_{H,H}$=6.2 Hz, $^2J_{H,F}$=47.4 Hz, 2H, 19-CH$_2$), 6.76 (s, 1H, 2-NH), 7.04-7.09 (m, 4H, 7-CH, 8-CH, 10-CH, 11-CH).

$^{13}$C-NMR (75 MHz, CDCl$_3$) δ [ppm]: 14.1 (q, C-23, C-25), 23.1 (q, C-21), 25.3 (dt, $^3J_{C,F}$=5.5 Hz, C-17), 29.3, 29.5, 29.8 (t, C-13 to C-16), 30.5 (dt, $^2J_{C,F}$=19.5 Hz, C-18), 31.7 (t, C-5), 33.5 (t, C-4), 35.6 (t, C-12), 62.7 (t, C-22, C-24), 66.5 (s, C-2), 84.3 (dt, $^1J_{C,F}$=164.0 Hz, C-19), 128.4, 128.5 (d, C-7, C-8, C-10, C-11), 137.8, 140.7 (s, C-6, C-9), 168.2 (s, C-1, C-3), 169.1 (s, C-20).

$^{19}$F-NMR (282 MHz, CDCl$_3$) δ [ppm]: −218.5 (tt, $^3J_{H,F}$=24.9 Hz, $^2J_{H,F}$=47.4 Hz, 1F, 19-CH$_2$F).

Exact mass (ESI$^+$): C$_{25}$H$_{38}$FNO$_5$+Na$^+$: calcd. 474.2626. found 474.2621. (C$_{25}$H$_{38}$FNO$_5$)$_2$+Na$^+$: calcd. 925.5360. found 925.5354.

15.5 N-{4-[4-(8-fluorooctyl)phenyl]-1-hydroxy-2-(hydroxymethyl)butan-2-yl}acetamide Diester 79 (48 mg, 106 μmol) was dissolved in THF (3 mL) and cooled to 0° C. Lithium borohydride (4 M solution in THF, 0.11 mL, 0.44 mmol, 4.2 eq.) was added to the solution followed by ethanol (6 mL). The mixture was warmed to r.t. after 30 min and stirred overnight. The reaction was diluted with 20% potassium sodium tartrate solution (4 mL) and the aqueous phase was extracted with dichloromethane (4×6 mL). The combined organic layers were dried over Na$_2$SO$_4$ and the solvent was removed under reduced pressure. Column chromatography (silica gel, 8×3 cm, dichloromethane/methanol, 20:1) gave a mixture of the desired product 80 and the aminoalcohol 81. This mixture was used in the next reaction. Yield: 13 mg (max. 33%).

Side product 81:

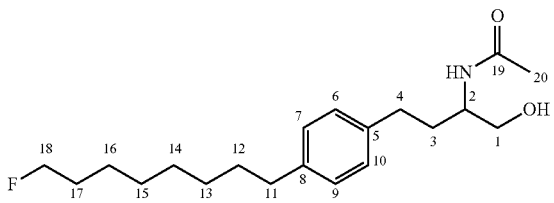

Exact mass (ESI$^+$): C$_{20}$H$_{32}$FNO$_2$+Na$^+$: calcd. 360.2309. found 360.2310.

15.6 2-Amino-2-(4-(8-fluorooctyl)phenethyl)propane-1,3-diol (SSS 969)

The mixture of aminodiol 80 and aminoalcohol 81 (13 mg, max. 0.035 mmol) was dissolved in methanol (1.5 mL), treated with 1 M sodium hydroxide solution (39 μL, 0.039 mmol, 1.1 eq.) and heated to 120° C. for 7 h in a pressure vessel. After cooling to r.t. overnight the mixture was diluted with 1 M sodium hydroxide solution (3 mL). The aqueous phase was extracted with dichloromethane (5×5 mL) and the combined organic layers were dried over MgSO$_4$. The solvent was removed and the residue was purified by gradient HPLC (RP-HPLC Nucleodur 100-10 C$_{18ec}$ column (250×16 mm), acetonitrile/water (0.1% TFA)) with a Knauer HPLC system. The obtained TFA salt was dissolved in methanol (1 mL) and 1 M sodium hydroxide solution (3 mL) and the mixture was extracted with dichloromethane (5×5 mL). The organic phases were dried over MgSO$_4$ and concentrated. The product was dried in high vacuum and obtained as highly viscous oil. Yield: 5 mg (44%).

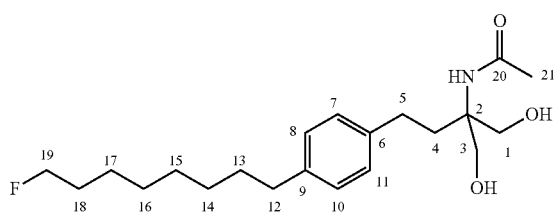

$^1$H-NMR (400 MHz, CD$_3$OD, CDCl$_3$) δ [ppm]: 1.26-1.44 (m, 8H, 14-CH$_2$ to 17-CH$_2$), 1.54-1.76 (m, 4H, 13-CH$_2$, 18-CH$_2$), 1.99 (s, 3H, 21-CH$_3$), 2.51-2.68 (m, 6H, 4-CH$_2$, 5-CH$_2$, 12-CH$_2$), 3.64 (d, $^2J_{H,H}$=11.5 Hz, 2H, 1-CH$_2$, 3-CH$_2$), 3.76 (d, $^2J_{H,H}$=11.5 Hz, 2H, 1-CH$_2$, 3-CH$_2$), 4.44 (dt, $^3J_{H,H}$=6.2 Hz, $^2J_{H,F}$=47.4 Hz, 2H, 19-CH$_2$), 5.35 (s, 1H, 2-NH), 7.02-7.18 (m, 4H, 7-CH, 8-CH, 10-CH, 11-CH).

$^{13}$C-NMR (101 MHz, CD$_3$OD, CDCl$_3$) δ [ppm]: 23.0 (q, C-21), 24.9 (dt, $^3J_{C,F}$=5.4 Hz, C-17), 29.0, 29.2 (t, C-13 to C-16), 30.2 (dt, $^2J_{C,F}$=19.3 Hz, C-18), 31.3 (t, C-5), 33.7 (t, C-4), 35.3 (t, C-12), 61.2 (s, C-2), 64.4 (t, C-1, C-3), 84.1 (dt, $^1J_{C,F}$=163.5 Hz, C-19), 128.0, 128.2 (d, C-7, C-8, C-10, C-11), 138.9, 140.2 (s, C-6, C-9), 172.4 (s, C-20).

$^{19}$F-NMR (282 MHz, CDCl$_3$) δ [ppm]: −218.4 (tt, $^3J_{H,F}$=25.0 Hz, $^2J_{H,F}$=47.4 Hz, 1F, 19-CH$_2$F).

Exact mass (ESI$^+$): C$_{21}$H$_{34}$FNO$_3$+Na$^+$: calcd. 390.2415. found 390.2415.

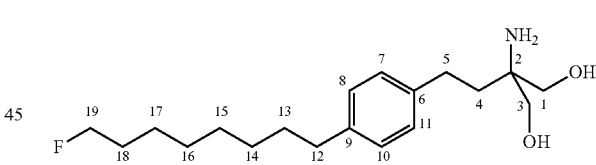

$^1$H-NMR (400 MHz, CD$_3$OD) δ [ppm]: 1.32 (m, 8H, 14-CH$_2$ to 17-CH$_2$), 1.53-1.74 (m, 6H, 4-CH$_2$, 13-CH$_2$, 18-CH$_2$), 2.52-2.65 (m, 4H, 5-CH$_2$, 12-CH$_2$), 3.47 (d, $^2J_{H,H}$=10.9 Hz, 2H, 1-CH$_2$, 3-CH$_2$), 3.54 (d, $^2J_{H,H}$=11.0 Hz, 2H, 1-CH$_2$, 3-CH$_2$), 4.40 (dt, $^3J_{H,H}$=6.2 Hz, $^2J_{H,F}$=47.5 Hz, 2H, 19-CH$_2$), 7.03-7.16 (m, 4H, 7-CH, 8-CH, 10-CH, 11-CH).

$^{13}$C-NMR (101 MHz, CD$_3$OD) δ [ppm]: 26.0 (dt, $^3J_{C,F}$=5.4 Hz, C-17), 29.8, 30.0, 30.0, 30.2 (t, C-13 to C-16), 31.3 (dt, $^2J_{C,F}$=19.4 Hz, C-18), 32.5 (t, C-5), 36.3 (t, C-4), 37.4 (t, C-12), 56.7 (s, C-2), 66.3 (t, C-1, C-3), 84.8 (dt, $^1J_{C,F}$=163.4 Hz, C-19), 128.9, 129.2 (d, C-7, C-8, C-10, C-11), 140.7, 141.1 (s, C-6, C-9).

$^{19}$F-NMR (282 MHz, CDCl$_3$) δ [ppm]: −218.5 (tt, $^3J_{H,F}$=25.0 Hz, $^2J_{H,F}$=47.3 Hz, 1F, 19-CH$_2$F).

Exact mass (ESI$^+$): C$_{19}$H$_{32}$FNO$_2$+H$^+$: calcd. 326.2490. found 326.2489. C$_{19}$H$_{32}$FNO$_2$+Na$^+$: calcd. 348.2309. found 348.2308.

15.7 N-{4-[4-(8-Fluorooctyl)phenyl]-1,4-dihydroxy-2-(hydroxymethyl)butan-2-yl}-acetamide Diester 78 (53 mg, 0.11 mmol), obtained as for example 15.3, was dissolved in THF (3 mL). Lithium chloride (29 mg, 0.68 mmol, 6.0 eq.) and sodium borohydride (26 mg, 0.68 mmol, 6.0 eq.) were added and the mixture was cooled to 0° C. Ethanol (6 mL) was added dropwise to the mixture which was warmed to r.t. after 40 min and stirred overnight. The reaction was stopped with 20% potassium sodium tartrate solution (5 mL) and the aqueous phase was extracted with dichloromethane (5×15 mL). The combined organic phases were dried over $Na_2SO_4$ and concentrated under reduced pressure. The product was purified by column chromatography (silica gel, 8×2 cm, dichloromethane/methanol, 20:1) and obtained as colourless oil. Yield: 21 mg (48%).

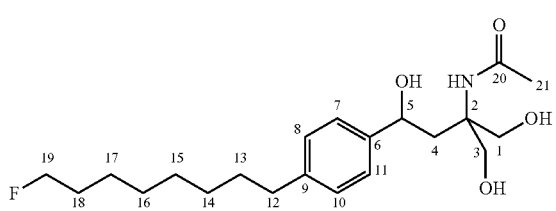

$^1$H-NMR (300 MHz, $CDCl_3$) δ [ppm]: 1.24-1.43 and 1.53-1.85 (m, 12H, 13-$CH_2$ to 18-$CH_2$), 2.02 (s, 3H, 21-$CH_3$), 2.31 (m, 2H, 4-$CH_2$), 2.58 (m, 2H, 12-$CH_2$), 3.42-3.80 (m, 4H, 1-$CH_2$, 3-$CH_2$), 4.43 (dt, $^3J_{H,H}$=6.2 Hz, $^2J_{H,F}$=47.4 Hz, 2H, 19-$CH_2$), 4.86 (d, $^3J_{H,H}$=10.5 Hz, 1H, 5-CH), 5.30 (s, 1H, 2-NH), 7.09-7.27 (m, 4H, 7-CH, 8-CH, 10-CH, 11-CH).

$^{13}$C-NMR (75 MHz, $CDCl_3$) δ [ppm]: 24.0 (q, C-21), 25.3 (dt, $^3J_{C,F}$=5.4 Hz, C-17), 29.3, 29.5, 31.6 (t, C-13 to C-16), 30.5 (dt, $^2J_{C,F}$=19.3 Hz, C-18), 35.7 (t, C-12), 41.4 (t, C-4), 61.5 (s, C-2), 65.1, 66.4 (t, C-1, C-3), 71.2 (d, C-5), 84.4 (dt, $^1J_{C,F}$=163.9 Hz, C-19), 125.6, 128.8 (d, C-7, C-8, C-10, C-11), 141.6, 142.9 (s, C-6, C-9), 172.0 (s, C-20).

$^{19}$F-NMR (282 MHz, $CDCl_3$) δ [ppm]: −218.5 (tt, $^3J_{H,F}$=25.0 Hz, $^2J_{H,F}$=47.4 Hz, 1F, 19-$CH_2F$).

Exact mass (ESI$^+$): $C_{21}H_{34}FNO_4$+Na$^+$: calcd. 406.2364. found 406.2358.

15.8 3-Amino-1-[4-(8-fluorooctyl)phenyl]-3-(hydroxymethyl)butane-1,4-diol (SSS 1003)

Protected triol 83 (20 mg, 0.05 mmol) was dissolved in methanol (3 mL), treated with 1 M sodium hydroxide solution (0.09 mL, 0.09 mmol, 1.7 eq.) and heated to 120° C. for 6 h in a pressure vessel. After cooling to r.t. overnight the mixture was diluted with 1 M sodium hydroxide solution (5 mL) and the aqueous phase was extracted with dichloromethane (5×8 mL). The combined organic layers were dried over $Na_2SO_4$ and concentrated. The residue was purified by gradient HPLC (RP-HPLC Nucleodur 100-10 $C_{18ec}$ column (250×16 mm), acetonitrile/water (0.1% TFA)) with a Knauer HPLC system. Afterwards the obtained TFA salt was dissolved in methanol (1 mL) and 1 M sodium hydroxide solution (3 mL). The mixture was extracted with dichloromethane (5×5 mL) and the organic phases were dried over $Na_2SO_4$ and concentrated. The product was dried in high vacuum and obtained as highly viscous oil. Yield: 12 mg (68%).

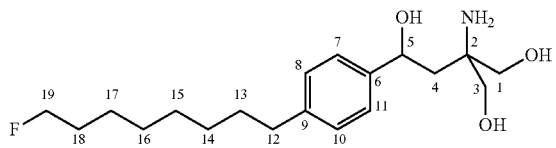

$^1$H-NMR (300 MHz, $CDCl_3$) δ [ppm]: 1.21-1.46 and 1.49-1.82 (m, 14H, 4-$CH_2$, 13-$CH_2$ to 18-$CH_2$), 2.55 (t, $^3J_{H,H}$=7.8 Hz, 2H, 12-$CH_2$), 3.42-3.79 (m, 4H, 1-$CH_2$, 3-$CH_2$), 4.43 (dt, $^3J_{H,H}$=6.2 Hz, $^2J_{H,F}$=47.4 Hz, 2H, 19-$CH_2$), 4.94 (d, $^3J_{H,H}$=10.2 Hz, 1H, 5-CH), 7.11 (d, $^3J_{H,H}$=7.7 Hz, 2H, 7-CH/11-CH or 8-CH/10-CH), 7.23 (d, $^3J_{H,H}$=7.8 Hz, 2H, 7-CH/11-CH or 8-CH/10-CH).

$^{13}$C-NMR (101 MHz, $CDCl_3$) δ [ppm]: 25.3 (dt, $^3J_{C,F}$=5.6 Hz, C-17), 29.3, 29.5, 29.8, 31.6 (t, C-13 to C-16), 30.5 (dt, $^2J_{C,F}$=19.4 Hz, C-18), 35.7 (t, C-12), 43.8 (t, C-4), 56.6 (s, C-2), 66.4, 68.1 (t, C-1, C-3), 70.7 (d, C-5), 84.4 (dt, $^1J_{C,F}$=163.9 Hz, C-19), 125.6, 128.6 (d, C-7, C-8, C-10, C-11), 142.2, 142.3 (s, C-6, C-9).

$^{19}$F-NMR (282 MHz, $CDCl_3$) δ [ppm]: −218.5 (tt, $^3J_{H,F}$=24.9 Hz, $^2J_{H,F}$=47.4 Hz, 1F, 19-$CH_2F$).

Exact mass (ESI$^+$): $C_{19}H_{32}FNO_3$+H$^+$: calcd. 342.2439. found 342.2437. $C_{19}H_{32}FNO_3$+Na$^+$: calcd. 364.2258. found 364.2255.

15.9 tert-Butyl [5-(4-iodostyryl)-2,2-dimethyl-1,3-dioxan-5-yl]carbamate

Aldehyde 37 (519 mg, 2.00 mmol) obtained as for example 7.2 was dissolved in 1,4,-dioxane (10 mL). 4-Iodobenzyl triphenylphosphoniumbromide (1.05 g, 2.20 mmol, 1.1 eq) and potassium carbonate (580 mg, 4.20 mmol, 2.1 eq.) were added and the mixture was heated to 110° C. for 5 h. After cooling to r.t. overnight the mixture was adsorbed on silica gel (3 g) and triphenylphosphinoxide was removed by column filtration (5×3 cm, pentane). The solvent was evaporated and the residue was subsequently purified by column chromatography (12×3 cm, cyclohexane/ethyl acetate, 10:1) to give a viscous oil. Yield: 220 mg (24%).

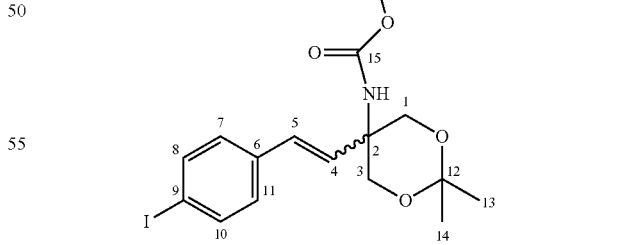

$^1$H-NMR (400 MHz, $CDCl_3$) δ [ppm]: 1.30-1.50 (m, 15H, 13-$CH_3$, 14-$CH_3$, 17-$CH_3$ to 19-$CH_3$), 3.74 (d, $^2J_{H,H}$=11.6 Hz, 2H, 1-$CH_2$, 3-$CH_2$), 3.87 (d, $^2J_{H,H}$=11.6 Hz, 2H, 1-$CH_2$, 3-$CH_2$), 5.15 (br s, 1H, 2-NH), 5.58 (d, $^3J_{H,H}$=12.7 Hz, 1H, 4-CH), 6.58 (d, $^3J_{H,H}$=12.6 Hz, 1H, 5-CH), 7.00 (d, $^3J_{H,H}$=8.3 Hz, 2H, 7-CH, 11-CH), 7.61 (d, $^3J_{H,H}$=8.4 Hz, 2H, 8-CH, 10-CH).

$^{13}$C-NMR (101 MHz, CDCl$_3$) δ [ppm]: 18.9 (q, 13-C, 14-C), 28.4 (q, 17-C to 19-C), 52.5 (s, 2-C), 66.0 (t, 1-C, 3-C), 79.5 (s, 16-C), 92.6 (s, 9-C), 98.2 (s, 12-C), 130.6, 131.3, 137.0, 137.6 (d, 4-C, 5-C, 7-C, 8-C, 10-C, 11-C), 136.1 (s, 6-C), 154.4 (s, 15-C).

Exact mass (ESI$^+$): C$_{19}$H$_{26}$INO$_4$+Na$^+$: calcd. 482.0799. found 482.0784. (C$_{19}$H$_{26}$INO$_4$)$_2$+Na$^+$: calcd. 941.1705. found 941.1680.

15.10 tert-Butyl {5-[4-(6-hydroxyhex-1-yn-1-yl)styryl]-2,2-dimethyl-1,3-dioxan-5-yl}-carbamate Iodide 85 (110 mg, 0.24 mmol) was dissolved in acetonitrile (2.0 mL) and treated with triphenylphosphine (8 mg, 12 mol %), palladium on activated carbon (8 mg, 3 mol %), copper iodide (3 mg, 5 mol %) and triethyl amine (0.1 mL, 0.72 mmol, 3.0 eq.). The mixture was stirred at r.t. for 20 min and then hex-5-yn-1-ol (41.4 μL, 0.36 mmol, 1.5 eq.) was added. Afterwards the reaction was stirred at r.t. for 1 h and finally heated to 80° C. for 90 min under microwave irradiation. After cooling to r.t. overnight the mixture was diluted with ethyl acetate (5 mL) and was filtered over celite. The solvent was removed and the residue was purified by column chromatography (silica gel, 13.5×3 cm, cyclohexane/ethyl acetate, 3:2). The product was obtained as colourless oil. Yield: 99 mg (96%).

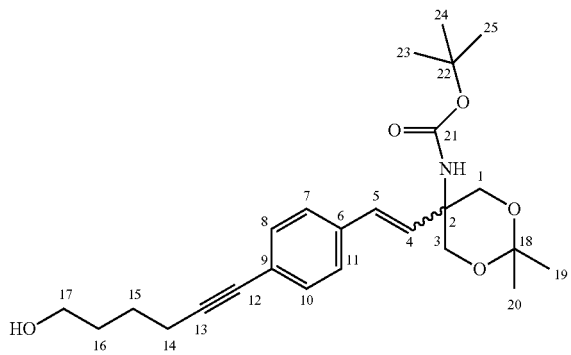

86

$^1$H-NMR (300 MHz, CDCl$_3$) δ [ppm]: 1.21-1.39 (m, 15H, 19-CH$_3$, 20-CH$_3$, 23-CH$_3$ to 25-CH$_3$), 1.45 (m, 2H, 16-CH$_2$), 1.67 (m, 2H, 15-CH$_2$), 2.45 (t, $^3J_{H,H}$=6.1 Hz, 1H, 14-CH$_2$), 3.65 (m, 2H, 17-CH$_2$), 3.74 (d, $^2J_{H,H}$=12.0 Hz, 2H, 1-CH$_2$, 3-CH$_2$), 3.87 (d, $^2J_{H,H}$=11.7 Hz, 2H, 1-CH$_2$, 3-CH$_2$), 5.25 (s, 1H, 2-NH), 5.58 (d, $^3J_{H,H}$=12.8 Hz, 1H, 4-CH), 6.63 (d, $^3J_{H,H}$=12.6 Hz, 1H, 5-CH), 7.15-7.20 and 7.28-7.34 (m, 4H, 7-CH, 8-CH, 10-CH, 11-CH).

$^{13}$C-NMR (75 MHz, CDCl$_3$) δ [ppm]: 18.9 (q, 19-C, 20-C), 19.2 (t, 14-C), 25.0 (t, 15-C), 28.3 (q, 23-C to 25-C), 31.8 (t, 16-C), 52.5 (s, 2-C), 62.1 (t, 17-C), 65.8 (t, 1-C, 3-C), 80.6 (s, 22-C), 84.3, 90.3 (s, 12-C, 13-C), 98.1 (s, 18-C), 122.7 (s, 9-C), 126.2, 128.5, 131.0, 131.8 (d, 4-C, 5-C, 7-C, 8-C, 10-C, 11-C), 136.7 (s, 6-C), 154.4 (s, 21-C).

Exact mass (ESI$^+$): C$_{25}$H$_{35}$NO$_5$+Na$^+$: calcd. 452.2407. found 452.2398. (C$_{25}$H$_{35}$NO$_5$)$_2$+Na$^+$: calcd. 881.4923. found 881.4897.

Ref.: Reaction procedure taken from R. Bera, N. K. Swamy, G. Dhananjaya, J. M. Babu, P. Rajender Kumar, K. Mukkanti, M. Pal, *Tetrahedron* 2007, 63, 13018-13023.

15.11 tert-Butyl N-{5-[4-(6-hydroxyhexyl)phenethyl]-2,2-dimethyl-1,3-dioxan-5-yl}-carbamate Ultrapure hydrogen gas was generated with a Nitrox UHP-40H hydrogen generator (DOMNICK HUNTER, England).
Alkyne 86 (208 mg, 0.48 mmol) was dissolved in benzene (8 mL) and the catalyst (10% palladium on activated carbon, 104 mg, 50 wt %) was added. The flask was flushed with hydrogen and the mixture was vigorously stirred at r.t. overnight under a hydrogen pressure of 1.5 bar. The reaction was stopped by releasing the hydrogen gas and the catalyst was filtered over celite. The solvent was removed under reduced pressure and the product was purified by column chromatography (silica gel, 4.5×3 cm, cyclohexane/ethyl acetate, 4:1) to give a white solid. Yield: 161 mg (77%).

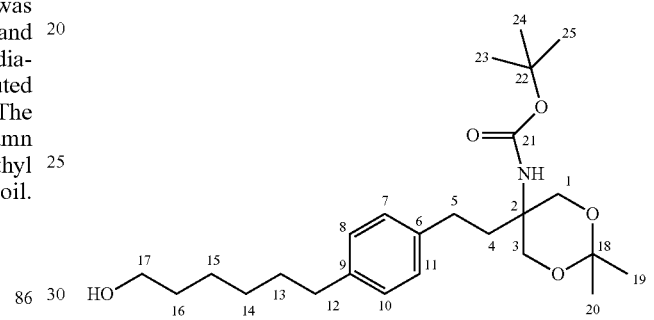

87

M.p.: 56-57° C.

$^1$H-NMR (300 MHz, CDCl$_3$) δ [ppm]: 1.30-1.40 (m, 4H, 14-CH$_2$, 15-CH$_2$), 1.40-1.50 (m, 15H, 19-CH$_3$, 20-CH$_3$, 23-CH$_3$ to 25-CH$_3$), 1.50-1.68 (m, 4H, 13-CH$_2$, 16-CH$_2$), 1.97 (m, 2H, 4-CH$_2$), 2.48-2.62 (m, 4H, 5-CH$_2$, 12-CH$_2$), 3.61 (t, $^3J_{H,H}$=6.7, 2H, 17-CH$_2$), 3.67 (d, $^2J_{H,H}$=11.8, 2H, 1-CH$_2$, 3-CH$_2$), 3.89 (d, $^2J_{H,H}$=11.8, 2H, 1-CH$_2$, 3-CH$_2$), 7.08 (m, 4H, 7-CH, 8-CH, 10-CH, 11-CH).

$^{13}$C-NMR (75 MHz, CDCl$_3$) δ [ppm]: 19.8 (q, C-19, C-20), 25.7 (t, C-15), 28.5 (q, C-23 to C-25), 28.7, 29.1, 29.2 (t, C-4, C-5, C-14), 31.6 (t, C-13), 32.7 (t, C-16), 35.5 (t, C-12), 51.8 (s, C-2), 62.9 (t, C-17), 66.4 (t, C-1, C-3), 79.4 (s, C-22), 98.4 (s, C-18), 128.3, 128.5 (d, C-7, C-8, C-10, C-11), 139.2, 140.3 (s, C-6, C-9), 155.0 (s, C-21).

Exact mass (ESI$^+$): C$_{25}$H$_{41}$NO$_5$+H$^+$: calcd. 436.3057. found 436.3055. C$_{25}$H$_{41}$NO$_5$+Na$^+$: calcd. 458.2877. found 458.2873.

Ref.: Reaction procedure is taken from S. Kim, H. Lee, M. Lee, T. Lee, *Synthesis* 2006, 5, 753-755.

15.12 tert-Butyl N-{5-[4-(6-fluorohexyl)phenethyl]-2,2-dimethyl-1,3-dioxan-5-yl}-carbamate Alcohol 87 (161 mg, 0.37 mmol) was dissolved in dry THF (5 mL) and treated with PBSF (0.14 mL, 0.78 mmol, 2.1 eq.), triethylamine trishydrofluoride (0.12 mL, 0.73 mmol, 2.0 eq.) and di-isopropyl ethyl amine (0.39 mL, 2.22 mmol, 6.0 eq.). The reaction mixture was stirred at r.t. for 2 days and quenched by addition of saturated sodium bicarbonate solution (5 mL). The aqueous phase was extracted with dichloromethane (3×15 mL) and the organic layer was dried over MgSO$_4$. The solvent was removed under reduced pressure and the residue was purified by column chromatography (silica gel, 9.5×3 cm, cyclohexane/ethyl acetate, 2:1). The product was obtained as white solid. Yield: 72 mg (45%).

88

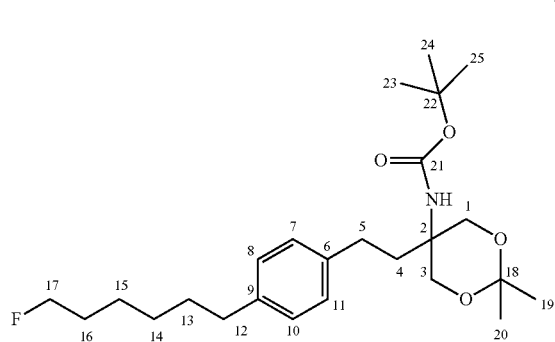

M.p.: 88-90° C.

¹H-NMR (300 MHz, CDCl₃) δ [ppm]: 1.35-1.44 and 1.56-1.76 (m, 14H, 13-CH$_2$ to 16-CH$_2$, 19-CH$_3$, 20-CH$_3$), 1.47 (s, 9H, 23-CH$_3$ to 25-CH$_3$), 1.97 (m, 2H, 4-CH$_2$), 2.49-2.60 (m, 4H, 5-CH$_2$, 12-CH$_2$), 3.68 (d, $^2J_{H,H}$=11.7 Hz, 2H, 1-CH$_2$, 3-CH$_2$), 3.89 (d, $^2J_{H,H}$=11.7 Hz, 2H, 1-CH$_2$, 3-CH$_2$), 4.42 (dt, $^3J_{H,H}$=6.1 Hz, $^2J_{H,F}$=47.4 Hz, 2H, 17-CH$_2$), 4.99 (br s, 1H, 2-NH), 7.08 (s, 4H, 7-CH, 8-CH, 10-CH, 11-CH).

¹³C-NMR (75 MHz, CDCl₃) δ [ppm]: 19.8 (q, C-19, C-20), 25.2 (dt, $^3J_{C,F}$=5.4 Hz, C-15), 28.6 (q, C-23 to C-25), 28.8, 29.0 (t, C-4, C-5, C-14), 30.4 (dt, $^2J_{C,F}$=19.4 Hz, C-16), 31.5 (t, C-13), 35.5 (t, C-12), 51.8 (s, C-2), 66.4 (t, C-1, C-3), 79.4 (s, C-22), 84.2 (dt, $^1J_{C,F}$=164.1 Hz, C-17), 98.5 (s, C-18), 128.3, 128.5 (d, C-7, C-8, C-10, C-11), 139.3, 140.3 (s, C-6, C-9), 155.0 (s, C-21).

¹⁹F-NMR (282 MHz, CDCl₃) δ [ppm]: −218.6 (tt, $^3J_{H,F}$=23.7 Hz, $^2J_{H,F}$=47.6 Hz, 1F, 17-CH$_2$F).

Exact mass (ESI⁺): C$_{25}$H$_{40}$FNO$_4$+H⁺: calcd. 438.3014. found 438.3014. C$_{25}$H$_{40}$FNO$_4$+Na⁺: calcd. 460.2834. found 460.2832.

15.13 2-Amino-2-(4-(6-fluorohexyl)phenethyl)propane-1,3-diol (SSS 944)

Protected aminodiol 88 (72 mg, 0.16 mmol) was dissolved in a mixture of dichloromethane, TFA and water (v/v, 2:2:1, 2.5 mL) and stirred at r.t. overnight. All volatile compounds were removed in vacuo and the residue was diluted with saturated sodium bicarbonate solution (5 mL). The aqueous phase was extracted with dichloromethane (4×8 mL) and the combined organic layers were washed with brine (1×8 mL), dried over Na$_2$SO$_4$ and concentrated under reduced pressure. The product was crystallized from ethyl acetate to give a white solid. Yield: 38 mg (81%).

89

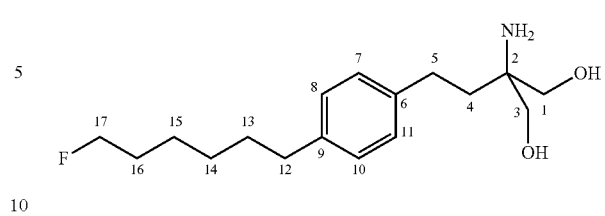

M.p.: 108° C.

¹H-NMR (300 MHz, CDCl₃, CD₃OD) δ [ppm]: 1.12-1.40 and 1.46-1.70 (m, 10H, 4-CH$_2$, 13-CH$_2$ to 16-CH$_2$), 2.43-2.60 (m, 4H, 5-CH$_2$, 12-CH$_2$), 3.40 (d, $^2J_{H,H}$=11.1 Hz, 2H, 1-CH$_2$, 3-CH$_2$), 3.48 (d, $^2J_{H,H}$=10.9 Hz, 2H, 1-CH$_2$, 3-CH$_2$), 4.34 (dt, $^3J_{H,H}$=6.1 Hz, $^2J_{H,F}$=47.4 Hz, 2H, 17-CH$_2$), 6.97-7.10 (m, 4H, 7-CH, 8-CH, 10-CH, 11-CH).

¹³C-NMR (75 MHz, CDCl₃, CD₃OD) δ [ppm]: 24.9 (dt, $^3J_{C,F}$=5.4 Hz, C-15), 28.7 (t, C-4, C-5, C-14), 30.2 (d, $^2J_{C,F}$=19.3 Hz, C-16), 31.2 (t, C-13), 35.2 (s, C-12), 56.1 (s, C-2), 65.5 (t, C-1, C-3), 84.1 (dt, $^1J_{C,F}$=163.5 Hz, C-17), 128.0, 128.3 (d, C-7, C-8, C-10, C-11), 139.0, 140.1 (s, C-6, C-9).

¹⁹F-NMR (282 MHz, CDCl₃, CD₃OD) δ [ppm]: −142.3 (tt, $^3J_{H,F}$=25.1 Hz, $^2J_{H,F}$=47.4 Hz, 1F, 17-CH$_2$F).

Exact mass (ESI⁺): C$_{17}$H$_{28}$FNO$_2$+H⁺: calcd. 298.2177. found 298.2182. C$_{17}$H$_{28}$FNO$_2$+Na⁺: calcd. 320.1996. found 320.2001.

Ref.: Reaction conditions are taken from S. Kim, H. Lee, M. Lee, T. Lee, *Synthesis* 2006, 5, 753-755.

16. Experimental Procedure for Testing the Compounds of the Invention

The compounds of the invention were tested for immunosuppressive biological activity in vivo based on the known ability of S1P analogues to induce peripheral blood lymphopenia due to lymphocyte trapping in secondary lymph organs. The immunosuppressive activity of compound 21 (555558) and of compound 27 (555890) was compared with the corresponding activity a non-fluorinated analogue compound 7 (5551091), and non-ω (or close to ω)-fluorinated compounds (compounds 8 (555535) and 12 (555517)) as well as with FTY720 as a standard. The compounds were injected intraperitoneally at 1.25 microgramm/kg body weight in a total volume of 200 microliter. 24 hours later, blood was drawn from the retroorbital plexus in 17.8 mM EDTA as an anti-coagulant. Lymphocytes (T- and B-cells) were analyzed by flow cytometry as following: After lysis of red blood cells by BD Pharm Lyse (Becton Dickinson) in 50 microliter blood, cells were washed, resuspended in 100 microliter FACS buffer (1% BSA in PBS), and antibodies to CD4, CD8 and B220 (Becton Dickinson) were added (1 microliter antibody per sample each) for 30 minutes at room temperature. After 3 washes, cells were then analyzed by flow cytometry in a Gallios Beckman Coulter flow cytometer.

The results are reported in table 1

TABLE 1

| | Immunosuppressive activity. | | | | | | |
|---|---|---|---|---|---|---|---|
| Compound | WBC [10⁶/mL] | CD4+ [10⁶/mL] | CD4+ [%] | CD8+ [10⁶/mL] | CD8+ [%] | B cells [10⁶/mL] | B cells [%] |
| Control* | 6.32 ± 0.61 | 0.6 ± 0.1 | 5.60 ± 1.1 | 0.54 ± 0.1 | 5.8 ± 1.1 | 1.74 ± 0.23 | 27.4 ± 2.8 |
| FTY 720 | 3.69 (mean) | 0.02 | 1.10 | 0.04 | 0.30 | 0.61 | 20.08 |
| | 0.63 (SEM) | 0 | 0.14 | 0.01 | 0.45 | 0.12 | 4.18 |

TABLE 1-continued

| | Immunosuppressive activity. | | | | | | | |
|---|---|---|---|---|---|---|---|---|
| Compound | | WBC [10⁶/mL] | CD4+ [10⁶/mL] | CD4+ [%] | CD8+ [10⁶/mL] | CD8+ [%] | B cells [10⁶/mL] | B cells [%] |
| SSS182 | CH$_3$-(CH$_2$)$_{11}$-CH=CH-CH$_2$-CH(NH$_2$)-CH$_2$OH | 6.90 | 0.43 | 6.30 | 0.48 | 7.00 | 2.91 | 42.20 |
| B1088 | CH$_3$-(CH$_2$)$_{11}$-CH=CH-CH$_2$-CH(NH$_2$)-CH$_2$-O-P(O)(OH)$_2$ | 7.15 | 0.34 | 4.80 | 0.49 | 6.90 | 2.76 | 38.60 |
| B1087 | CH$_3$-(CH$_2$)$_{11}$-C(F)=CH-CH$_2$-CH(NH$_2$)-CH$_2$-O-P(O)(OH)$_2$ | 7.06 | 0.42 | 5.90 | 0.59 | 8.40 | 2.49 | 35.20 |
| SSS822 | CH$_3$-(CH$_2$)$_{11}$-CH=CH-CH$_2$-C(NH$_2$)(CH$_2$OH)$_2$ | 5.02 (mean) 1.04 (SEM) | 0.10 0.01 | 2.30 0.53 | 0.12 0.05 | 2.67 1.14 | 1.17 0.33 | 26.87 8.54 |
| SSS1091 | CH$_3$-(CH$_2$)$_{11}$-(CH$_2$)$_2$-C(NH$_2$)(CH$_2$OH)$_2$ | 4.14 (mean) 0.60 (SEM)?? | 0.09 0.02 | 2.20 0.63 | 0.08 0.01 | 2.07 0.30 | 1.27 0.26 | 34.20 10.44 |
| SSS535 | CH$_3$-(CH$_2$)$_{11}$-(CH$_2$)$_2$-C(NH$_2$)(CH$_2$OH)(CH$_2$F) | 7.05 | 0.42 | 6.00 | 0.39 | 5.50 | 3.54 | 50.20 |
| SSSS517 | CH$_3$-(CH$_2$)$_{11}$-(CH$_2$)$_2$-CHF-C(NH$_2$)(CH$_2$OH)$_2$ | 11.35 | 0.54 | 4.80 | 0.60 | 5.30 | 4.81 | 42.40 |
| SSS564 | CH$_3$-(CH$_2$)$_{11}$-(CH$_2$)$_2$-CHF-C(NH$_2$·HCl)(CH$_2$OH)$_2$ | 13.07 | 0.65 | 5.00 | 0.98 | 7.50 | 5.52 | 42.20 |
| SSS558 | F-CH$_2$-(CH$_2$)$_{11}$-(CH$_2$)$_3$-C(NH$_2$)(CH$_2$OH)$_2$ | 3.74 (mean) 0.70 (SEM) | 0.15 0.08 | 0.60 3.22 | 0.13 0.04 | 1.50 1.91 | 1.52 0.04 | 43.20 7.07 |
| SSS379 | CH$_3$-(CH$_2$)$_{11}$-(CH$_2$)$_3$-C(NHAc)(CH$_2$OH)$_2$ | 7.43 | 0.49 | 6.60 | 0.62 | 8.40 | 4.25 | 57.20 |

TABLE 1-continued

Immunosuppressive activity.

| Compound | WBC [10⁶/mL] | CD4+ [10⁶/mL] | CD4+ [%] | CD8+ [10⁶/mL] | CD8+ [%] | B cells [10⁶/mL] | B cells [%] |
|---|---|---|---|---|---|---|---|
| SSS846 | 9.28 | 0.98 | 10.60 | 0.52 | 5.60 | 5.32 | 57.30 |
| SSS943 | 1.73 | 0.04 | 2.25 | 0.04 | 2.35 | 0.60 | 35.21 |
| SSS862 | 5.31 | 0.27 | 5.00 | 0.41 | 7.80 | 3.23 | 60.90 |
| SSS864 | 5.27 | 0.28 | 5.40 | 0.37 | 7.00 | 3.41 | 64.70 |

*control: untreated mice; SEM: standard error of the mean

Excellent immunosuppressive effect was observed in respect to the reduction of CD4+ and CD8+ T-cells, respectively, and B-lymphocytes in the peripheral blood (see table 1). CD4 cells have molecules called CD4 on their surface. They start the immune response that protects the body from infectious invaders such as bacteria and viruses. CD8 cells, with molecules on their surface called CD8, destroy other infected cells and produce antiviral substances that fight off infectious organisms.

Additionally, a longer biological effectiveness (biological half-life) has been observed. Interestingly, the fluorination of compound 8 (SSS535) diminishes effectiveness. The other comparative fluorinated compound 12 (SSS517) also shows a very moderate immunosuppressive action demonstrating the relevance of the terminal positions (omega and close to omega) for immunosuppressive activity.

Compound 21 (SSS558), compound 27 (SSS890) and the other compounds of the invention are extremely attractive not only for therapeutic but also e.g. for imaging applications (when labelled or bearing a dye) as they can be applied for diagnostic imaging in a much lower dose that will not have a biological effect and will also not interfere with any simultaneous treatments with other drugs targeting the same receptors. It is possible to administrate the compounds of the invention for imaging purposes to patients treated simultaneously with other S1P receptor drugs as only trace amounts of the compounds of the invention will be necessary. Furthermore, the compounds of the invention will not compete for biological activity with such drugs and hence will not require any adjustment of their therapeutic dosage.

The invention claimed is:

1. A compound of formula (II):

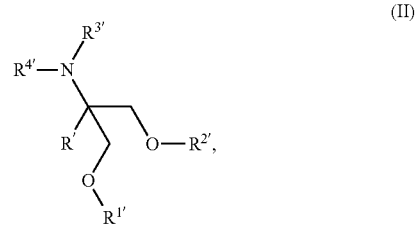

or a pharmaceutically acceptable salt thereof, wherein:

R' is selected from the group consisting of —(CH$_2$)$_n$CH$_2$—X', —(CH$_2$)$_{n'}$—Y'—(CH$_2$)$_m$—X', —(CH$_2$)$_{n'}$—(CF$_2$)$_p$—(CH$_2$)$_m$—X', —(CH$_2$)$_{n'}$—CX'H—CH$_3$, —(CH$_2$)$_{n'}$—CX'H—CH$_2$—CH$_3$, and —(CH$_2$)$_q$(CHOH)$_t$(CH$_2$)$_r$-Aryl-(CH$_2$)$_s$—X';

X' is selected from the group consisting of —$^{123}$I, —$^{124}$I, —$^{131}$I, —O—Z', —S—Z', —NH—Z', —NZ'Alkyl, —CO—Z', —CH(O-Alkyl)$_2$, —CO$_2$—Z', —CONH—Z', —CONZ'Alkyl, —CH=CH—Z' and —C≡C—Z';

Z' is selected from the group consisting of dansyl, —NH-Cy3, Cy5, Cy5.5, and Cy7, or Z' is

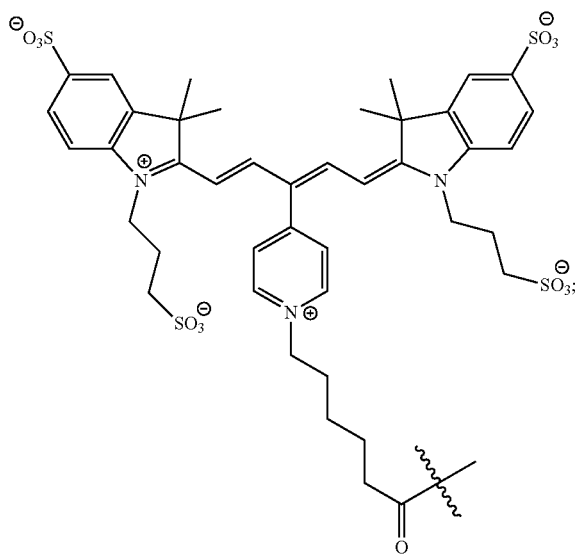

Y' is selected from the group consisting of O, S, SO, SO₂, C(O), CH(OH), CH(O-Alkyl), CH(O-Aryl), CH(O-Heteroaryl), C(O-Alkyl)₂, epoxide, vic-diol, vic-acetal, CH=CH and C≡C;

n' is selected from the group consisting of 8, 9, 10, 11, 12, 13, 14, 15, 16, 17, 18, 19, and 20;

m' is selected from the group consisting of 2, 3, 4, 5, 6, 7, 8, 9 and 10;

p' is selected from the group consisting of 1, 2, 3, 4, and 5;

q' is selected from the group consisting of 1, 2, 3, 4, and 5;

r' is selected from the group consisting of 0, 1, 2, 3, 4, and 5;

s' is selected from the group consisting of 6, 7, 8, 9, and 10;

t' is selected from the group consisting of 0 and 1;

each of $R^{1'}$ and $R^{2'}$ is independently selected from the group consisting of —H, —C(O)Alkyl, —C(O)Aryl, —C(O)Heteroaryl, —PO₃²⁻, and —P(OH)(O)₂⁻;

each of $R^{3'}$ and $R^{4'}$ is independently selected from the group consisting of —H, —C(O)Alkyl, —C(O)Aryl, and —C(O)Heteroaryl;

with the proviso that:
when R' is —(CH₂)$_{n'}$—(CF₂)$_{p'}$—(CH₂)$_{m'}$—X', wherein X' is as defined above, the sum n'+m'+p' is 12-24; and
when R' is —(CH₂)$_{n'}$—Y'—(CH₂)$_{m'}$—X', wherein Y' and X' are as defined above, the sum n'+m' is 12-24.

2. The compound of claim 1, wherein:
R' is selected from the group consisting of —(CH₂)$_{n'}$CH₂—X', —(CH₂)$_{n'}$—Y'—(CH₂)$_{m'}$—X', —(CH₂)$_{n'}$—(CF₂)$_{p'}$—(CH₂)$_{m'}$—X', —(CH₂)$_{n'}$—CX'H—CH₃, and —(CH₂)$_{n'}$—CX'H—CH₂—CH₃;

X' is selected from the group consisting of —¹²³I, —¹²⁴I, —¹³¹I, —O—Z', —S—Z', —NH—Z', —NZ'Alkyl, —CO—Z', —CH(OAlkyl)₂, —CO₂—Z', —CONH—Z', —CONZ'Alkyl, —CH=CH—Z', and —C≡C—Z';

Z' is selected from the group consisting of dansyl, Cy3, Cy5, Cy5.5, and Cy7;

Y' is selected from the group consisting of O, S, SO, SO₂, C(O), CH(OH), CH(O-Alkyl), CH(O-Aryl), CH(O-Heteroaryl), C(O-Alkyl)₂, epoxide, vic-diol, vic-acetal, CH=CH, and C≡C;

n' is selected from the group consisting of 8, 9, 10, 11, 12, 13, 14, 15, 16, 17, 18, 19, and 20;

m' is selected from the group consisting of 2, 3, 4, 5, 6, 7, 8, 9, and 10;

p' is selected from the group consisting of 1, 2, 3, 4, and 5;

each of $R^{1'}$ and $R^{2'}$ is independently selected from the group consisting of —H, —C(O)Alkyl, —C(O)Aryl, —C(O)Heteroaryl, —PO₃²⁻, and —P(OH)(O)₂⁻;

each of $R^{3'}$ and $R^{4'}$ is independently selected from the group consisting of —H, —C(O)Alkyl, —C(O)Aryl, and —C(O)Heteroaryl;

with the proviso that:
when R' is —(CH₂)$_{n'}$—(CF₂)$_{p'}$—(CH₂)$_{m'}$—X', wherein X' is as defined above, the sum n'+m'+p' is 12-24; and
when R' is —(CH₂)$_{n'}$—Y'—(CH₂)$_{m'}$—X', wherein Y' and X' are as defined above, the sum n'+m' is 12-24.

3. The compound of claim 2, wherein X' is selected from the group consisting of —O—Z', —S—Z', —NH—Z', —NZ'Alkyl, —CO—Z', —CO₂—Z', —CONH—Z', —CONZ'Alkyl, —CH=CH—Z', and —C≡C—Z'.

4. The compound of claim 2, wherein X' is selected from the group consisting of —O—Z', —S—Z', —NH—Z', —NZ'Alkyl, —CO—Z', —CO₂—Z', —CONH—Z', —CONZ'Alkyl, —CH=CH—Z', and —C≡C—Z'.

5. The compound of claim 1, wherein R' is —(CH₂)$_{q'}$(CHOH)$_{t'}$(CH₂)$_{r'}$—C₆H₄—(CH₂)$_{s'}$—X'.

6. The compound of claim 1, wherein n' is 14, 15 or 16.

7. The compound of claim 1, wherein n' is 14.

8. The compound of claim 1, wherein n' is 15.

9. The compound of claim 1, wherein n' is 16.

10. The compound of claim 2, wherein n' is 14, 15 or 16.

* * * * *